(12) United States Patent
Helman et al.

(10) Patent No.: US 9,574,003 B2
(45) Date of Patent: Feb. 21, 2017

(54) LOW FUCOSE CELL LINES AND USES THEREOF

(75) Inventors: Daniel Helman, Kiryat Ono (IL); Meirav Barshimon, Gedera (IL); Mira Toister-Achituv, Rehovot (IL)

(73) Assignee: Merck Serono S.A., Coinsins (CH)

( * ) Notice: Subject to any disclaimer, the term of this patent is extended or adjusted under 35 U.S.C. 154(b) by 0 days.

(21) Appl. No.: 14/003,767

(22) PCT Filed: Mar. 5, 2012

(86) PCT No.: PCT/IL2012/000109
§ 371 (c)(1),
(2), (4) Date: Sep. 6, 2013

(87) PCT Pub. No.: WO2012/120500
PCT Pub. Date: Sep. 13, 2012

(65) Prior Publication Data
US 2014/0005368 A1   Jan. 2, 2014

(30) Foreign Application Priority Data

Mar. 6, 2011   (IL) .......................... 211583
Dec. 27, 2011  (IL) .......................... 217216

(51) Int. Cl.
| | |
|---|---|
| *A01N 63/00* | (2006.01) |
| *A61K 48/00* | (2006.01) |
| *C07K 16/28* | (2006.01) |
| *C07K 16/00* | (2006.01) |
| *C12N 9/04* | (2006.01) |
| *C12N 9/10* | (2006.01) |
| *C12N 9/88* | (2006.01) |
| *C12N 15/01* | (2006.01) |
| *C12N 15/85* | (2006.01) |

(52) U.S. Cl.
CPC .......... *C07K 16/2863* (2013.01); *C07K 16/00* (2013.01); *C12N 9/0006* (2013.01); *C12N 9/1051* (2013.01); *C12N 9/88* (2013.01); *C12N 15/01* (2013.01); *C12N 15/85* (2013.01); *C12Y 101/01271* (2013.01); *C12Y 204/01068* (2013.01); *C12Y 402/01047* (2013.01); *C07K 2317/41* (2013.01); *C07K 2319/30* (2013.01)

(58) Field of Classification Search
None
See application file for complete search history.

(56) References Cited

U.S. PATENT DOCUMENTS 6,852,533 B1 * 2/2005 Rafii et al. .................... 435/372

FOREIGN PATENT DOCUMENTS

| JP | WO 02/33140 A1 * | 4/2002 |
|---|---|---|
| JP | 2004-344031 A | 12/2004 |
| WO | WO-2010/010674 A1 | 1/2010 |
| WO | WO-2010/036443 A1 | 4/2010 |
| WO | WO-2011/007764 A1 | 1/2011 |

OTHER PUBLICATIONS

Kanda et al. English Translation of WO 02/33140A1, 2002.*
Ohyama et al. J Biol Chem 1998;273:14582-7.*
Anolik et al., The relationship of FcγRIIIa genotype to degree of B cell depletion by rituximab in the treatment of systempic lupus erythematosus, *Arthritis & Rheum.*, 48(2):455-9 (2003).
Carter, Potent antibody therapeutics by design, *Nat. Rev. Immunol.*, 6:343 (2006).
Cartron et al., Therapeutic activity of humanized anti-CD20 monoclonal antibody and polymorphism in IgG Fc receptor Fc γRIIIa gene, *Blood*, 99:754-8 (2002).
Chow et al., Random population-wide genetic damage induced in replicating cells treated with methotrexate, *Mutation Research*, 413:251-64 (1998).
Clark, IgG effector mechanisms, *Antibody Engineering*, 65:88-110 (1997).
Coquelle et al., Expression of fragile sites triggers intrachromosomal mammalian gene amplification and sets boundaries to early amplicons, *Cell*, 89:215-25 (1997).
Cox et al., Glycan optimization of a human monoclonal antibody in the aquatic plant Lemna minor, *Nat. Biotechnol.*, 24(12):1591 (2006).
Crowe et al., Humanized monoclonal antibody CAMPATH-1H: myeloma cell expression of genomic constructs, nucleotide sequence of cDNA constructs and comparison of effector mechanisms of myeloma and Chinese hamster ovary cell-derived material, *Clin. Exp. Immunol.*, 87:105-10 (1992).
Dall'Ozzo et al., Rituximab-dependant cytotoxicity by natural killer cells: Influence of FCGR3A polymorphism on the concentration-effect relationship, *Can. Res.*, 64:4664-9 (2004).
Gennari et al., Pilot study of the mechanism of action of preoperative trastuzumab in patients with primary operable breast tumors over expressing HER2, *Clin. Can. Res.*, 10:5650-5 (2004).
Hamilton et al., Humanization of yeast to produce complex terminally sialylated glycoproteins, *Sci.*, 313:1441 (2006).
Hoffmann et al., Rapid isolation of choriocapillar endothelial cells by Lycopersicon esculentum-coated Dynabeads, *Graefe's Arch. Clin. Exp. Opthalmol*, 236:779-84 (1998).

(Continued)

*Primary Examiner* — Janice Li
(74) *Attorney, Agent, or Firm* — Marshall, Gerstein & Borun LLP

(57) ABSTRACT

A method of selecting cells having zero fucose level useful as host cells for expressing recombinant proteins is disclosed. The method comprises: (d) introducing genetic mutations into a population of CHO cells by contacting the cells with a methotrexate (MTX), (e) contacting the population of CHO cells comprising mutated cells with a non-toxic fucose binding agent for an amount of time that allows binding of the fucose binding agent to a fucose moiety on a cell membrane of the population of cells, wherein the amount of time does not allow killing of the cells; and (f) depleting from the population of cells comprising mutated cells, a subpopulation of cells which bind the fucose binding agent, thereby selecting cells useful as host cells for expressing recombinant proteins, the selected cells having zero fucose content. There are also disclosed cells and cell lines useful as host cells for expressing recombinant proteins.

32 Claims, 31 Drawing Sheets

(56) References Cited

OTHER PUBLICATIONS

Idusogie et al., Engineered antibodies with increased activity to recruit complement, *J. Immunol.*, 166:2571-5 (2001).

Idusogie et al., Mapping of the C1q binding site on Rituxan a chimeric antibody with a human IgG1 Fc, *J. Immunol.*, 164:4178-84 (2000).

Iida et al., Two mechanisms of the enhanced antibody-dependent cellular cytotoxicity (ADCC) efficacy of non-fucosylated therapeutic antibodies in human blood, *BMC Cancer*, 9:58 (2009).

Imai-Nishiya et al., Double knockdown of α1,6-fucosyltransferase (FUT8) and GDP-mannose 4,6-dehydratase (GMD) in antibody-producing cells: a new strategy for generating fully non-fucosylated therapeutic antibodies with enhanced ADCC, *BMC Biotechnol.*, 7:84 (2007).

Jackson et al., Binding of human endothelium to Ulex europaeus I-coated Dynabeads: application to the isolation of microvascular endothelium, *J. Cell Sci.*, 96:257-62 (1990).

Jefferis et al., Glycosylation of recombinant antibody therapeutics, *Biotechnol. Prog.*, 21:11-6 (2005).

Jefferis, Antibody therapeutics: isotype and glycoform selection, *Exp. Opin. Biol. Ther.*, 7(9)1401-13 (2007).

Jefferis, Recombinant antibody therapeutics: the impact of glycosylation on mechanisms of activation, *Cell*, 356 (2009).

Kanda et al., Comparison of cell lines for stable production of fucose-negative antibodies with enhanced ADCC, *Biotech. Bioeng.*, 94(4):680 (2006).

Kanda et al., Establishment of a GDP-mannose 4,6-dehydratase (GMD0 knockout host cell line: A new strategy for generating completely non-fucosylated recombinant therapeutics, *J. Biotechnol.*, 130:300-10 (2007).

Lazar et al., Engineered antibody Fc variants with enhanced effector function, *Prot. Natl. Acad. Sci. USA*, 103(11):4005-10 (2006).

Louis et al., Association between polymorphism in IgG Fc receptor IIIa coding gene and biological response to infliximab in Chron's disease, *Aliment Pharmocol. Ther.*, 19:511-9 (2004).

Masuda et al., Enhanced binding affinity for FcγRIIIa of fructose-negative antibody is sufficient to induce maximal antibody-dependant cellular cytotoxicity, *Molec. Immunol.*, 44:3122-31 (2007).

Miescher et al., A single recombinant anti-RhD IgG prevents RhD immunization: association of RhD-positive red blood cell clearance rate with polymorphisms in the FcγRIIA and FcγIIIA genes, *Blood*, 103(11):4028 (2004).

Morgan et al., The N-terminal end of the CH2 domain of chimeric human IgG1 anti-HLA-DR is necessary for C1q, FcγRI and FcγRIII binding, *Immunol.*, 86:319-24 (1995).

Moutel et al., Meeting report: "Antibodies-Europe. Engineering the next generation of antibodies", *Biotechnol. J.*, 3:298-300 (2008).

Natsume et al., Fucose removal from complex-type oligo saccharide enhances the antibody-dependent cellular cytotoxicity of single-gene-encoded antibody comprising a single-chain antibody linked the antibody constant region. *J. Immunol. Methods*, 306:93-103 (2005).

Nechansky et al., Compensation of endogenous IgG mediated inhibition of antibody-dependant cellular cytotoxicity by glycol-engineering of therapeutic antibodies, *Molec. Immunol.*, 44:1815-7 (2007).

Nezlin et al., Interactions of immunoglobulins outside the antigen-combining site, *Adv. Immunol.*, 82:155 (2004).

Oganezyan et al., Structural characterization of a mutated, ADCC-enhanced human Fc fragment, *Molec. Immunol.*, 45:1872-82 (2008).

Ohyama et al., Molecular cloning and expression of GDP-D-mannose-4,6-dehydratase, a key enzyme for fructose metabolism defective in Lec13 cells, *J. Biol. Chem.*, 273(23):14582-7 (1998).

Presta, Molecular engineering and design of therapeutic antibodies, *Curr. Opin. Immunol.*, 20:460-70 (2008).

Raju et al., Terminal sugars of Fc glycans influence antibody effector functions of IgGs, *Curr. Opin. Immunol.*, 20:471-8 (2008).

Reichert et al., Development trends for monoclonal antibody cancer therapeutics. *Nat. Rev. Drug. Disc.*, 6:349 (2007).

Ripka et al., Lectin-Resistant CHO-Cells: Selection of Four ne pea lectin-resistant phenotypes, *Somatic Cell Molec. Genet.*, 12(1):51-62 (1986).

Ripka et al., Two Chinese hamster ovary glycosylation mutants affected in the conversion of GDP-Manose to GDP-Fructose, *Arch. Biochem. Biophys.*, 249(2):533-45 (1986).

Roopenian et al., FcRn: the neonatal Fc receptor comes of age, *Nat. Rev. Immunol.*, 7:715 (2007).

Saifeld, Isotype selection in antibody engineering, *Nature Biotechnol.*, 25(12):1369 (2007).

Schimke, Gene amplification in cultured cells, *J. Biol. Chem.*, 263(13):5989-92 (1988).

Sheilds et al., Lack of fucose on human IgG1 N-linked oligosaccharide improves binding to human FcγRIII and antibody-dependent cellular toxicity, *J. Biol. Chem.*, 277:26733-40 (2002).

Shinkawa et al., The absence of fucose but not the presence of galactose or bisecting N-acetylglucosamime of human IgG1 complex-type oligosaccarides shows the critical role in enhancing antibody-dependent cellular cytotoxicity, *J. Biol. Chem.*, 278:3466-73 (2003).

Singer et al., Amplification of the human dihydrofolate reductase gene via double minutes is initiated by chromosome breaks, *Prot. Natl. Acad. Sci. USA*, 97(14):7921-6 (2000).

Somoza et al., Structural and kinetic analysis of *Escherichia coli*GDP-mannose-4,6 dehydratase provides insights into the enzyme's catalytic mechanism and regulation by GDP-fucose, *Structure*, 8:123-35 (2000).

Strohl, Optimization of Fc-mediated effector functions of monoclonal antibodies, *Curr. Opin. Biotechnol.*, 20:685-91 (2009).

Strohl, Therapeutic monoclonal antibodies: Past, present and future, Chapter 1, John Wiley & Sons, Inc. (2009).

Sullivan et al., Molecular cloning of human GDP-mannose 4,6-Dehydratase and recnstitution of GDP-fucose biosynthesis in vitro, *J. Biol. Chem.*, 273:8193-202 (1998).

Treon et al., Polymorphisms in FcγRIIIA (CD16) receptor expression are associated with clinical response to Rituximab in Waldenstrom's Macroglobulinemia, *J. Clin. Oncol.*, 23:474-81 (2005).

Umaña et al., Engineered glycoforms of an antineuroblastoma IgG1 with optimized antibody-dependant cellular cytotoxic activity, *Nat. Biotechnol.*, 17:176 (1999).

Von Horsten et al., Production of non-fucosylated antibodies by co-expression of heterologous GDP-6-deoxy-D-lyxo-4-hexulose reductase, *Glycobiol.*, 20(12)1607-18 (2010).

Webb et al., Crystal structure of a tetrameric GDP-D-mannose 4,6-dehydratase from a bacterial GDP-D-rhamnose biosynthetic pathway, *Protein Sci.*, 13:529-39 (2004).

Weng et al., Two immunoglobulin G fragment C receptor polymorphisms independently predict response to rituximab in patients with follicular lymphoma, *J. Clin. Oncol.*, 21:3940-7 (2003).

Yamane-Ohnuki et al., Establishment of FUT8 knockout Chinese hamster ovary cells: An ideal host cell line for producing completely defucosylated antibodies with enhanced antibody-dependent cellular cytotoxicity, *Biotech. Bioeng.*, 87(5):614 (2004).

* cited by examiner

```
GMD (Full)    1  mahapascpssrnsgdgdkgkprkvalitgitgqdgsylaefllekgyevhgivrrsssfntgriehlyknpqahiegnm
GMD SV1       1  mahapascpssrnsgdgdkgkprkvalitgitgqdgsylaefllekgyevhgivrrsssfntgriehlyknpqahiegnm GMD (Full)   81  klhygdltdstclvkiinevkpteiynlgaqshvkisfdlaeytadvdgvgtlrlldaiktcglinsvkfyqastselyg
GMD SV1     241  klhygdltdstclvkiinevkpteiynlgaqshvkisfdlaeytadvdgvgtlrlldaiktcglinsvkfyqastselyg GMD (Full)  161  kvqeipqkettpfyprspygaaklyaywivvnfreaynlfavngilfnhesprrganfvtrkisrsvakiylgqlecfsl
GMD SV1     481  kvqeipqkettpfyprspygaaklyaywivvnfreaynlfavngilfnhesprrganfvtrkisrsvakiylgqlecfsl GMD (Full)  241  gnldakrdwghakdyveamwlmlqndepedfviatgevhsvrefveksfmhigktivwegknenevgrcketgkihvtvd
GMD SV1     721  gnldakrdwghakdyve-----------------------------------------------------------------
                                          Deletion of Exon 9 in SV1
GMD (Full)  321  lkyyrptevdflqgdcskaqqklnwkprvafdelvremvqadvelmrtnpna
GMD SV1     772  ---------dflqgdcskaqqklnwkprvafdelvremvqadvelmrtnpna
```

B

```
GMD (Full)    1  mahapascpssrnsgdgdkgkprkvalitgitgqdgsylaefllekgyevhgivrrsssfntgriehlyknpqahiegnm
GMD SV2       1  mahapascpssrnsgdgdkgkprkvalitgitgqdgsylaefllekgye-------------------------------
                                                                 Deletion of Exon 3 and Exon 4 in SV2
GMD (Full)   81  klhygdltdstclvkiinevkpteiynlgaqshvkisfdlaeytadvdgvgtlrlldaiktcglinsvkfyqastselyg
GMD SV2     148  ------------------------------------isfdlaeytadvdgvgtlrlldaiktcglinsvkfyqastselyg GMD (Full)  161  kvqeipqkettpfyprspygaaklyaywivvnfreaynlfavngilfnhesprrganfvtrkisrsvakiylgqlecfsl
GMD SV2     283  kvqeipqkettpfyprspygaaklyaywivvnfreaynlfavngilfnhesprrganfvtrkisrsvakiylgqlecfsl GMD (Full)  241  gnldakrdwghakdyveamwlmlqndepedfviatgevhsvrefveksfmhigktivwegknenevgrcketgkihvtvd
GMD SV2     523  gnldakrdwghakdyveamwlmlqndepedfviatgevhsvrefveksfmhigktivwegknenevgrcketgkihvtvd GMD (Full)  321  lkyyrptevdflqgdcskaqqklnwkprvafdelvremvqadvelmrtnpna
GMD SV2     763  lkyyrptevdflqgdcskaqqklnwkprvafdelvremvqadvelmrtnpna
```

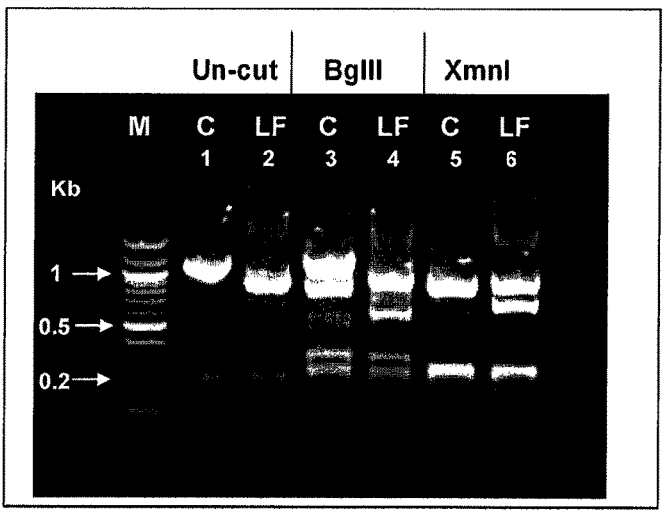

FIG. 30
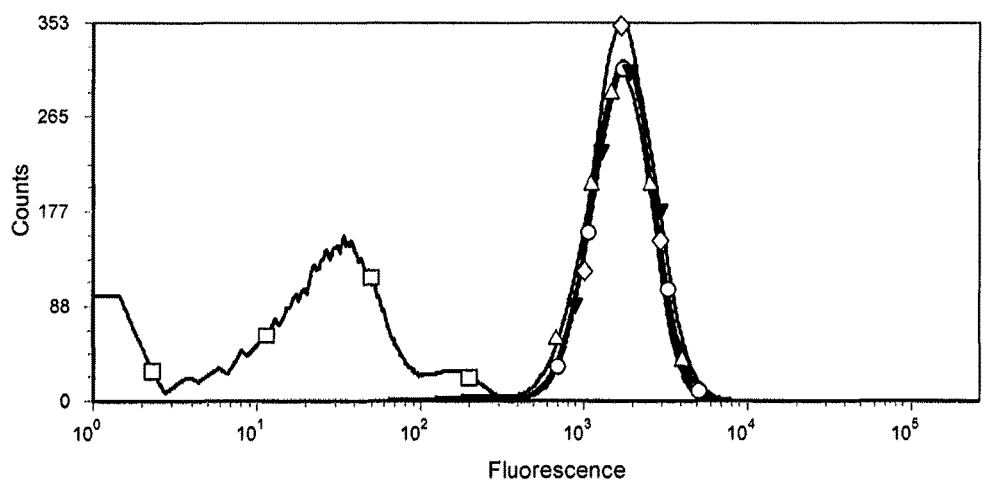
FIGs. 31A-B
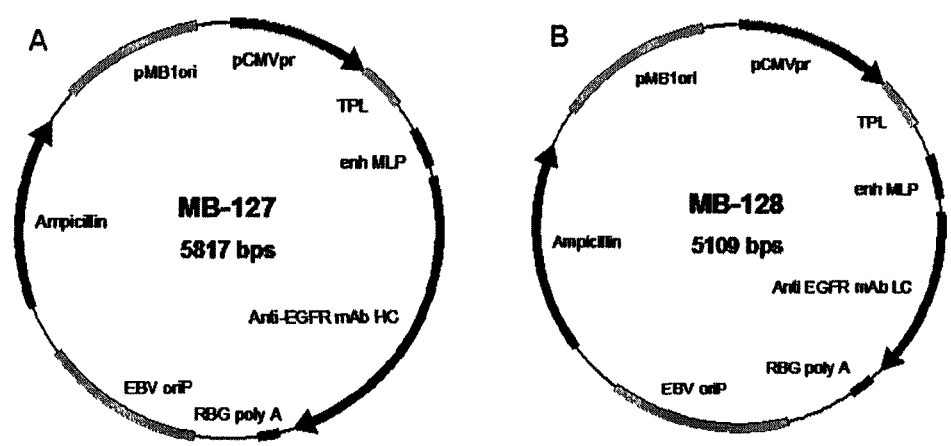

| Sample | Glycan Structure | | Relative abundance | Fucosylation Percentage |
|---|---|---|---|---|
| Normal Fucose CHO-S WT | | G0-F | 25.5 % | 100 % |
| | | G1-F | 56.8 % | |
| | | G2-F | 17.8 % | |
| Low Fucose ITL-LF2 | | G0-F | 45.9 % | 0% |
| | | G1-F | 49.0 % | |
| | | G2-F | 5.1 % | |

LOW FUCOSE CELL LINES AND USES THEREOF

FIELD AND BACKGROUND OF THE INVENTION

The present invention, in some embodiments thereof, relates to CHO cell lines, methods of generating same and uses thereof.

Recombinant therapeutic antibodies play an important role in treatment of a large variety of diseases. It is estimated that about 30% of the new coming drugs are likely to be based on antibodies in the next decade. Thirty recombinant antibodies and Fc fusion were approved for marketing with sales in 2008 that reached $35 billion.

Antibodies contain a target antigen-specific region which is composed of the variable regions of both the heavy and the light chains. This part of the antibody may bind and neutralize a soluble antigen or a membrane bound target.

The Fc portion is responsible for effector functions through antibody dependant cellular cytotoxicity (ADCC) mechanism, complement dependant complex (CDC) and the neonatal receptor FcRn. Those effector functions are mediated through interaction of the effector molecules with the hinge and CH2 regions of the Fc. The CH2 domain contains an oligosaccharide located on the N glycosylation site at position 297 of the antibody which is known to play an important role in binding to effector cells. The oligosaccharide is usually composed of a complex diantennary type with considerable heterogeneity, such as a core heptasaccharide together with additional variable outer sugar residues.

ADCC is one of the critical killing mechanisms for antibodies that bind ligands on target cells' membrane. FcγR expressed on leucocytes bind the CH2 domain of the antibodies and upon binding and creation of immune complexes with antigens on the target cells activation of the leucocytes is initiated. The activation may include phagocytosis and release of cell mediators that lead to cell permeabilization and death. The ADCC activity is dependent on the IgG isotype on the one hand, and on a specific FcγR, on the other hand. Whereas IgG1 and IgG3 may induce this activity, IgG4 does not. The FcγR that binds the IgG and is important for ADCC mechanism activation is known as the FcγRIIIa and is expressed on NK cells and macprophages. In many cases the ADCC activity obtained upon binding of the NK cell to the target cell is not efficient enough to perform killing of the target cell. The reason is that the affinity of the FcγRIIIa to the IgGI is low.

Increased ADCC activity was found in patients expressing the high affinity allotype FcγRIIIa—158Val found in 10-15% of the population in comparison to patients expressing the FcγRIIIa—158Phe. Elevated ADCC was obtained also by manipulations done on the IgG Fc. Computational design algorithms were used in order to engineer antibodies and select for high affinity by high-throughput screening. This work yielded antibodies which display >2 orders of magnitude enhancement of in vitro effector function (Lazar, Dang et al. 2006), although decrease thermostability of mutated IgG1 (IgG1 with mutations S239D, A330L and I332E) was detected. Another approach for obtaining antibodies with enhanced ADCC is to produce them with low fucose levels on their oligosaccharide at position 297. Previously it was found that fucose residues on the oligosaccharide interfere with Fc binding to FcγRIIIa (Shinkawa, Nakamura et al. 2003). One way for obtaining antibodies with low fucose levels is to harness cells with such natural capabilities, such as Rat hybridoma YB2/0 cells (Shinkawa, Nakamura et al. 2003), although recombinant proteins produced in these cells have variable levels of fucose content. Several other possibilities of non-mammalian cells include avian cells from Vivalis, engineered aquatic plant Lemna from Biolex (Cox, Sterling et al. 2006) and variant of the moss Physocmirtella patens from Igeneon (Nechansky, Schuster et al. 2007). In addition, GlycoFi generated various lines of *Pichia Pastoris* cells with capabilities for several glycosylation solutions including enhanced ADCC (Hamilton, Davidson et al. 2006). Also several mammalian cells are used for production of antibodies with various glycosylation solutions in general and enhanced ADCC in particular. Glycotope created various human glycoengineered cell lines to glyco-optimize bio-therapeutics glycosylation. Glycart, acquired by Roche, engineered a cell line producing recombinant antibodies with reduced fucose level by introducing beta(1,4)—N-acetylglucosaminyltransferase III (GnTIII), a glycosyltransferase catalyzing formation of bisected oligosaccharides that have been implicated in antibody-dependent cellular cytotoxicity (ADCC) (Umana, Jean-Mairet et al. 1999). Biowa generated a knockout in the fucosyl transference 8 (Fut8) gene of CHO DG44 in order to diminish the fucose levels (Yamane-Ohnuki, Kinoshita et al. 2004).

A recent research demonstrated that heterologous expression of the prokaryotic enzyme GDP-6-deoxy-D-lyxo-4-hexylose reductase within the cytosol can block the conversion of the intermediate GDP-4-keto-6-deoxymannose into a dead-end product that typically does not occur in vertebrate cells. Therefore CHO cells that were modified in this way secreted antibodies lacking core fucose (von Horsten, Ogorek et al.). Another approach was to create lectin resistant mutants that survive in the presence of toxic fucose specific lectin. LEC13 is a CHO based cell line that was developed by incubation of CHO cells in the presence of toxic pea fucose specific lectin (Ripka and Stanley 1986). LEC13 is deficient in GDP-mannose 4,6-dehydratase activity which results in expression of human IgG1 that are deficient of fucose (Shields, Lai et al. 2002).

U.S. Patent Application No. 2010/0081150 teaches mutation of CHO cells by treatment with chemicals and selecting cells which exhibit a variant glycosylation pattern including a decrease in fucosylation by killing cells with high fucose, in order to generate cells useful for expressing antibodies.

U.S. Patent Application No. 2010/0304436 teaches fucosylation reduced CHO cell lines by mutation in the Fx protein and controlling the availability of an external source of fucose in order to direct the ability of the cells to fucosylate polypeptides.

Kanda et al, (Kanda, Imai-Nishiya et al. 2007) discloses GMD and FUT8 knockout host cell lines. The GMD knockout cells have a genomic deletion corresponding to GMD exon 5, 6 and 7 regions.

Ripka et al. (Ripka and Stanley 1986) discloses four lectin resistant CHO mutant cells. The mutations were effected by incubation with N-methyl-N-nitrosoguanidine.

Shields et al, (Shields, Lai et al. 2002) discloses that IgG1 produced by the Lec13 (fucose deficient CHO) cell line increased binding to FcγRIIIA up to 50 fold and also increased ADCC.

Kanda et al., (Kanda, Yamane-Ohnuki et al. 2006) discloses that Lec13 produces 50-70% fucosylated antibody; however this known cell line could not stably produce antibody. Thus the Lec13 cell line is not suitable as a production cell line.

SUMMARY OF THE INVENTION

According to an aspect of some embodiments of the present invention there is provided a method of selecting CHO cells useful as host cells for expressing recombinant proteins, the method comprising:

(a) introducing genetic mutations into a population of CHO cells by contacting the cells with a methotrexate (MTX), (b) contacting the population of CHO cells comprising mutated cells with a non-toxic fucose binding agent for an amount of time that allows binding of the fucose binding agent to a fucose moiety on a cell membrane of the population of cells, wherein the amount of time does not allow killing of the cells; and (c) depleting from the population of cells comprising mutated cells, a subpopulation of cells which bind the fucose binding agent, thereby selecting cells useful as host cells for expressing recombinant proteins, the selected cells having zero fucose content.

According to an aspect of some embodiments of the present invention there is provided an isolated CHO cell generated according to the method of the present invention.

According to an aspect of some embodiments of the present invention there is provided an isolated CHO cell being genetically modified to express a imitated GDP-mannose 4,6-dehydratase (GMD) having an amino acid sequence as set forth in SEQ ID NOs: 23 and/or 24.

According to an aspect of some embodiments of the present invention there is provided a CHO cell line comprising the isolated cell of the present invention.

According to an aspect of some embodiments of the present invention there is provided a cell culture which comprises the isolated CHO cell of the present invention and a cell culture medium being devoid of xeno contaminants.

According to an aspect of some embodiments of the present invention there is provided a method for the production of a recombinant protein comprising transfecting the isolated CHO cell of the present invention with a polynucleotide comprising a nucleic acid sequence which encodes the recombinant protein, culturing the transfected CHO cell under conditions suitable for expression of the recombinant protein, and isolating the protein.

According to an aspect of some embodiments of the present invention there is provided an isolated CHO cell being genetically modified such that an amount of fucosylation of a protein expressed therein is linearly dependent on a concentration of external fucose.

According to some embodiments of the invention, the fucose binding agent is non-toxic to the mutated population of CHO cells.

According to some embodiments of the invention, the fucose binding agent is attached to a detectable moiety or an affinity moiety.

According to some embodiments of the invention, the introducing genetic mutations into the population of CHO cells is effected by contacting the cells with a mutagen that causes a mutation in GDP-mannose 4,6-dehydratase, a gene of the fucose synthesis pathway.

According to some embodiments of the invention, the amount of time during which the mutated cell population is contacted with a fucose binding agent is no longer than 60 minutes.

According to some embodiments of the invention, when the fucose binding agent is attached to an affinity moiety, the method further comprises contacting the mutated population of CHO cells with an additional agent, such additional agent comprising a cognate binding moiety for the affinity moiety.

According to some embodiments of the invention, the affinity moiety comprises biotin.

According to some embodiments of the invention, the cognate binding moiety is attached to a detectable moiety.

According to some embodiments of the invention, the detectable moiety comprises a fluorescent moiety or a magnetic moiety.

According to some embodiments of the invention, the depleting is effected by FACS sorting.

According to some embodiments of the invention, the depleting is effected by magnetic separation.

According to some embodiments of the invention, the depleting is effected by at least three rounds of sequential depleting.

According to some embodiments of the invention, the CHO cells are selected from CHO-S, CHO-K1, DUXB11, CHO/DG44 and Pro-5.

According to some embodiments of the invention, the fucose binding agent is aleuria aurantia lectin (AAL) or *Aspergillus oryzae* 1-fucose-specific lectin (AOL).

According to some embodiments of the invention, the isolated CHO cell expresses a wild-type fucosyl transferase-8 (Fut8).

According to some embodiments of the invention, the isolated CHO cell expresses a wild-type GDP-keo-6-deoxymannose 3,5-epimerase, 4-reductase (FX).

According to some embodiments of the invention, the mutated GMD has an amino acid sequence as set forth in SEQ ID NOs: 23 and/or 24.

According to some embodiments of the invention, the isolated CHO cell expresses a mutated GDP-mannose 4,6-dehydratase (GMD).

According to some embodiments of the invention, the isolated cells have a stable fucose phenotype for at least 370 population doublings.

According to some embodiments of the invention, the isolated CHO cell expresses a recombinant protein of interest.

According to some embodiments of the invention, the cell culture medium comprises fucose.

According to some embodiments of the invention, the cell culture medium is devoid of fucose.

According to some embodiments of the invention, the transfecting is effected in the presence of exogenous fucose.

According to some embodiments of the invention, the method further comprises culturing the isolated CHO cell of the present invention in a culture medium comprising fucose following the transfecting.

According to some embodiments the recombinant protein is an antibody.

According to some embodiments the recombinant protein is a Fc fusion protein.

According to some embodiments the antibodies have enhanced ADCC.

According to some embodiments the isolated CHO cell is genetically modified to express a mutated GDP-mannose 4,6-dehydratase (GMD).

According to some embodiments, at least one allele of the GMD carries at least one loss of function mutation.

According to some embodiments, each allele of the GMD carries at least one loss of function mutation.

According to some embodiments, when the concentration of external fucose is zero, the amount of fucosylation of the protein is zero.

According to some embodiments the isolated CHO cell has a 20% higher integral viable cell concentration (IVCC) than non-mutated CHO cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 19D is a graph illustrating lactate concentration of ITL-LF2 and CHO-S in a batch process.

FIGS. 22A-B are protein sequence comparisons between full length GMD and splice variants. cDNAs prepared by RT PCR from RNA extracted from CHO-S and ITL-LF2 cells were run on gels, isolated and sequenced. The DNA sequence was then translated to protein by the CloneManager™ software. The protein sequence of splice variant 1 (SV1; FIG. 22A; SEQ ID NO: 23) and splice variant 2 (SV2; FIG. 22B, SEQ ID NO: 24) were compared to the full length GMD gene (SEQ ID NO: 25). Dashed lines denote areas of deletion. Text indicates which exons are deleted in each splice variant.

FIGS. 23A-B illustrate restriction enzyme analysis of the two GMD splice variants (SEQ ID NOs: 26 and 27, respectively). FIG. 23A—Location of unique restriction enzyme sites within GMD splice variants; FIG. 23B—Agarose gel showing the bands after restriction. Sizes and their explanations are detailed in the Table 7 of the Examples section below.

FIG. 30 is a graph illustrating FACS analysis of sialic acid levels on ITL-LF2 anti EGFR mAb transfected cells. Analysis of sialic acid levels on the membrane of anti EGFR mAb transfected cells propagated in ProCHO5 medium. The cells were labeled with FITC conjugated sialic acid binding lectin (MAA) and analyzed by FACS. CHO-S, not labeled (□), CHO-S(○), ITL-LF2 (◇), CHO-S anti-EGFR mAb transfected (▼), ITL-LF2 anti-EGFR mAb transfected (Δ).

FIGS. 31A-B are illustrations of vectors constructed for transient transfection into ITL-LF2 cells. Vectors MB-127 and MB-128 were constructed on the backbone of vector pTT5. anti EGFR mAb-LC—Light chain of EGFR mAb; anti EGFR mAbANTI EGFR MAB-HC—heavy chain of EGFR mAb.

DESCRIPTION OF SPECIFIC EMBODIMENTS OF THE INVENTION

The present invention, in some embodiments thereof, relates to zero fucose CHO cells and cell lines, methods of generating same and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In order to reduce the fucosylation levels of recombinant proteins, e.g. antibodies for obtaining enhanced ADCC, the present inventors developed cell lines from CHO-S cells which were modified to express variant glycosylation patterns on their cell surface. This was effected by incubation of cells in the presence of a MTX followed by an efficient selection of cells with the lowest fucose levels on the cells' membrane.

The selection was performed either by isolation on magnetic beads and FACS sorting (FIGS. 7A-B) or by FACS sorting only (FIG. 12) using fucose specific lectins which have high affinity towards the αFuc1-6GlcNA residue present on the Fc glycosylation site of an antibody (e.g. aleuria aurantia lectin (AAL) or *Aspergillus oryzae* 1-fucose-specific lectin (AOL)).

Although the selection of the zero fucose expressing cells was performed according to the fucose levels on the cells' membrane, the same fucose levels were found on the recombinant antibody (anti EGFR mAb) expressed in these cells, as analyzed by a variety of methods (FIGS. 33-41).

Figure 49:
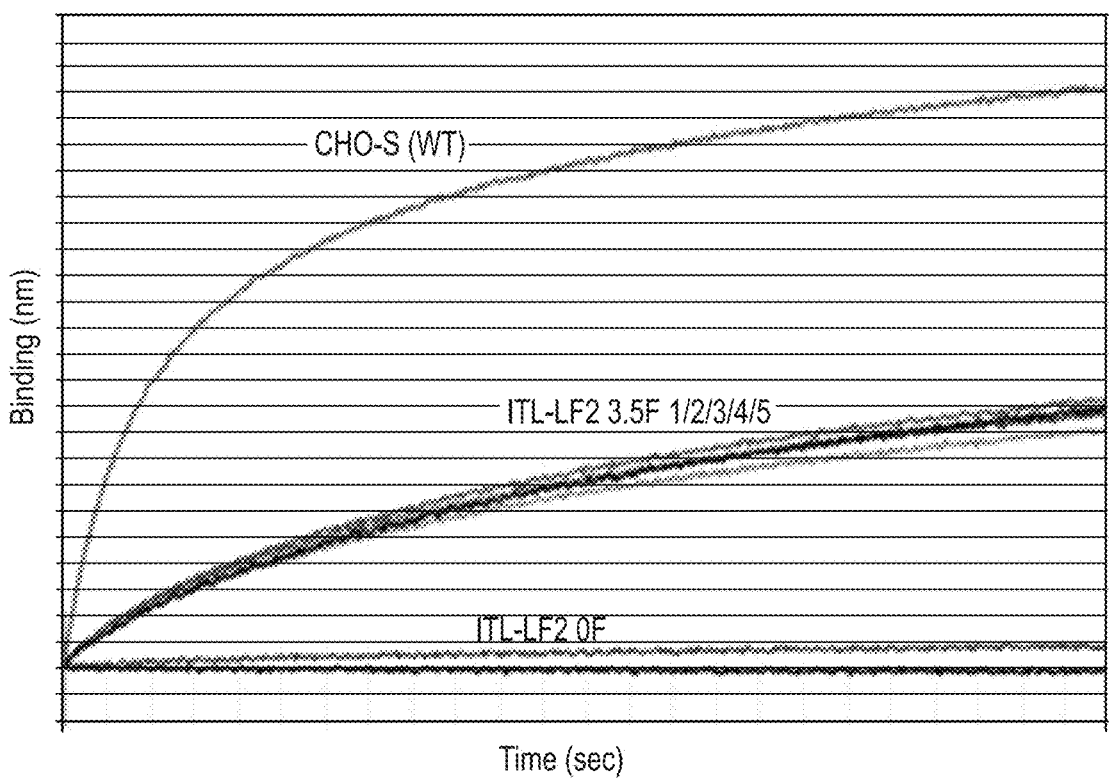
FIG. 49 is an analysis of partly fucosylated anti-EGFR Fc monomer fractions by Octet. The Fc monomer fraction of anti-EGFR mAb from CHO-S cells and from ITL-LF2 cells 40 µg/ml by O.D. 280 were bound to Biotinylated AAL (1 µg/ml) that was previously attached to Streptavidin pre-coated biosensors. The graph represents the association step of the kinetic analysis by the Octet QK system. Each curve corresponds to a specific sample.

By incubating the cells in medium comprising fucose, the present inventors showed that the level of fucosylation on the recombinant protein expressed therein is regulatable. This result was shown to be reproducible (FIG. 49).

Figure 15:
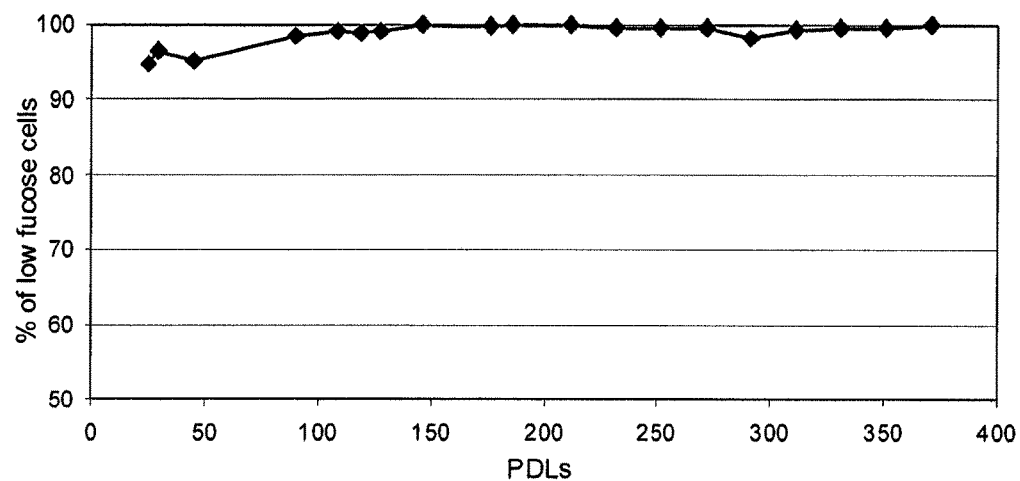
FIG. 15 is a graph illustrating FACS analysis on ITL-LF2 cells to analyze the level of fucose on cell surface at different times points after completion of the separation process, in order to evaluate the stability of low fucose expression. For analysis, the cells were labeled with of biotinylated AAL and fluorescent streptavidin.

In addition, the phenotype of the cells of the present invention was found to be stable for 370 PDLs tested (FIG. 15). Thus such cells lend themselves as production cells for recombinant proteins, where more than 100 PDLs are required.

Figure 11:
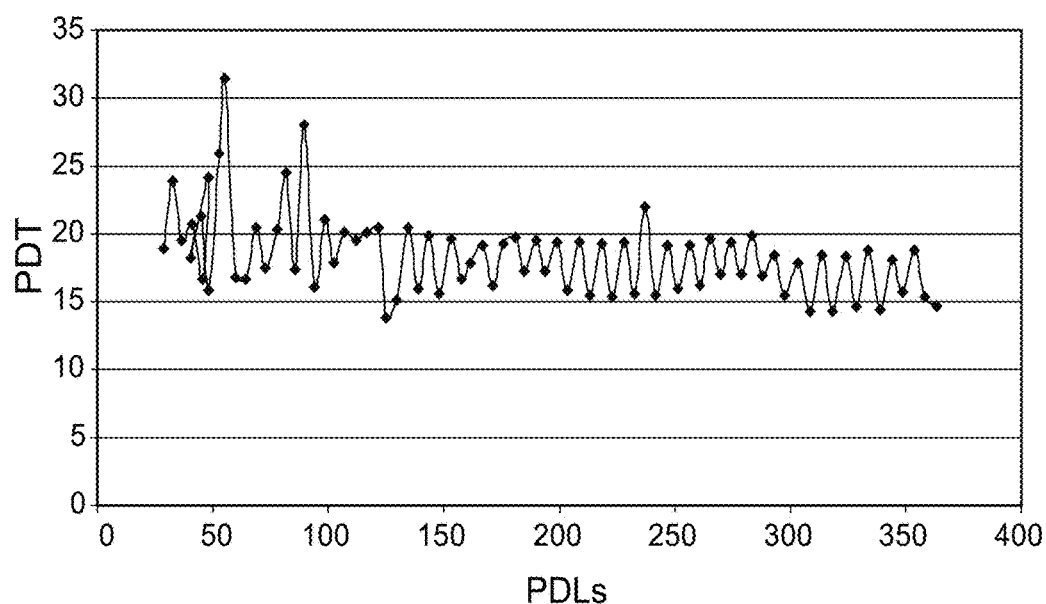
FIG. 11 is a graph illustrating the evaluation of growth rate of ITL-LF1 cells. ITL-LF1 cells were propagated along 363 population doublings (PDLs) and the growth rate was determined after every passage.

The growth rate of the zero fucose expressing cells (designated ITL-LF2 cells) was determined during the fucose stability test and was found to result in a population doubling time (PDT) of about 15-20 hours (FIG. 11), similar to CHO-S, from which the ITL-LF2 was derived.

Analysis of the key proteins known to be involved in fucosylation revealed that the mRNA size of GDP-mannose 4,6-dehydratase (GMD) in the selected cells of the present invention was shorter than in their wild-type counterparts (FIG. 20) and the sequence revealed two splice variants. The mRNA molecules extracted from the cells lacked either the third and fourth, or the eighth and ninth exons (FIGS. 21A-B and FIGS. 22A-B).

The present inventors propose that the method disclosed herein for generating and identifying cell types of particular attributes may be exploited for selecting additional useful cell types.

Thus, according to one aspect of the present invention there is provided a method of selecting CHO cells useful as host cells for expressing recombinant proteins, the method comprising:

(a) introducing genetic mutations into a population of CHO cells by contacting the cells with MTX, (b) contacting the population of CHO cells comprising mutated cells with a fucose binding agent for an amount of time that allows binding of the fucose binding agent to a fucose moiety on a cell membrane of the population of cells, wherein the amount of time does not allow killing of the cells; and (c) depleting from the population of cells, a subpopulation of cells which bind the fucose binding agent, thereby selecting cells useful as host cells for expressing recombinant proteins, the selected cells having a zero fucose content.

A Chinese hamster ovary tissue-derived CHO cell or cell line suitable in accordance with the present invention is any cell which is a cell line established from an ovary tissue of Chinese hamster (*Cricetulus griseus*). Examples include CHO cells described in documents such as Journal of Experimental Medicine, 108, 945 (1958); Proc. Nat. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Nat. Acad. Sci. USA, 77, 4216 (1980); Proc. Nat. Acad. Sci., 60, 1275 (1968); Cell, 6, 121 (1975); Molecular Cell Genetics, Appendix I, II (pp. 883-900); and the like. In addition, CHO-K1 (ATCC CCL-61), DUXB11 (ATCC CCL-9096) and Pro-5 (ATCC CCL-1781) registered in ATCC (The American Type Culture Collection) as well as CHO-S (Life Technologies, Cat #11619) or sub-cell lines obtained by adapting the cell lines using various media can also be employed in the present invention.

In some embodiments, the host cell is a CHO-1E5, CHO-S, CHO/DG44, CHO-3F, or CHO-2.6 clone.

The mutagen MTX causes a mutation in a gene or polypeptide involved in the fucose synthesis pathway.

As mentioned, the method of an aspect of the present invention is effected by contacting a mutated population of CHO cells with a fucose binding agent so as to allow binding thereof to the cell membranes of the mutated cells.

As used herein, the phrase "fucose binding agent" refers to any agent (e.g. lectin) that is capable of binding to fucose moieties on the cell surface with a Kd of at least $1 \times 10^{-5}$. According to one embodiment, the fucose binding agent binds to αFuc1-6GlcNA residues with a Kd of at least $1\times10^{-3}$ (Matsumura, Higashida et al. 2009), e.g. a Kd of at least $1\times10^{-4}$, a Kd of at least $1\times10^{-5}$, a Kd of at least $1\times10^{-6}$ or a Kd of at least $1\times10^{-7}$.

According to one embodiment, the fucose binding agent is a polypeptide, e.g. a lectin.

Exemplary lectins contemplated by the present invention include, but are not limited to aleuria aurantia lectin (AAL) or *Aspergillus oryzae* 1-fucose-specific lectin (AOL) and *Ulex europaeus* agglutinin (UEA) and those disclosed in (Oda, Senaha et al. 2003; Tateno, Nakamura-Tsuruta et al. 2009), the contents of which are incorporated herein by reference.

As mentioned, the contacting is effected under conditions that allow the binding of the fucose binding agents to the fucose on the cell membranes. According to one embodiment, the binding is affected under conditions that do not allow the lectin to cause death to the cells (i.e. cell depletion) to which it binds.

According to a specific embodiment, the binding is affected under conditions that do no allow the lectin to cause death to more than 50% of the cells to which it binds.

According to a specific embodiment, the binding is affected under conditions that do no allow the lectin to cause death to more than 40% of the cells to which it binds.

According to a specific embodiment, the binding is affected under conditions that do no allow the lectin to cause death to more than 30% of the cells to which it binds.

According to a specific embodiment, the binding is affected under conditions that do no allow the lectin to cause death to more than 20% of the cells to which it binds.

According to one embodiment, the binding is effected for no more than 3 hours, preferably no more than 2 hours and even more preferably no more than one hour.

According to one embodiment, the fucose-binding agent of this aspect of the present invention is attached to a functional moiety that allows depletion (either directly or indirectly) of the cell population that is bound to the agent.

Thus, the fucose binding agent may be attached to a detectable moiety, including but not limited to a fluorescent moiety or a magnetic moiety.

Exemplary fluorescent moieties may include fluorescein or its derivatives, such as fluorescein isothiocyanate (FITC), Oregon Green, Tokyo Green, SNAFL, carboxynaphthofluorescein (CFSE), Carboxyfluorescein diacetate succinimidyl ester (CFDA-SE), DyLight 488, Alexa Fluor 488, green fluorescent protein (GFP), phycoerythrin (PE), Peridinin Chlorophyll protein (PerCP), PE-Alexa Fluor 700, PE-Cy5 (TRI-COLOR), PE-Cy5.5, PE-Alexa Fluor 750, PE-Cy7, allophycocyanin (APC), APC-Cy7, and derivatives thereof.

Alternatively, the fucose binding agent may be attached to an affinity moiety.

As used herein, the term "affinity moiety" refers to a molecule capable of selective interaction with a cognate binding moiety, such as for example biotin/avidin, ligand/receptor, and the like.

Detailed protocols for attaching fucose binding agents to affinity or detectable moieties may be found in the Examples section herein below.

It will be appreciated that if the fucose binding agent is attached to a fluorescent moiety (either directly, or indirectly through a cognate binding molecule), the mutated cell population may be depleted of unwanted cells using known cell sorting procedures such as by using a fluorescence-activated cell sorter (FACS).

A multitude of flow cytometers are commercially available including for e.g. Becton Dickinson FACScan and FACScaliber (BD Biosciences, Mountain View, Calif.). Antibodies that may be used for FACS analysis are taught in Schlossman S, Boumell L, et al, [Leucocyte Typing V. New York: Oxford University Press; 1995] and are widely commercially available.

If the fucose binding agent is attached to a magnetic moiety (either directly, or indirectly through a cognate binding molecule), the mutated cell population may be depleted of unwanted cells by magnetic activated cell separation.

If the fucose binding agent is attached to an affinity moiety, the mutated cell population may be depleted of unwanted cells by affinity purification with the cognate binding molecule. Thus, for example, if the fucose binding agent is attached to biotin, the mutated cell population may be depleted of unwanted cells by purification with strepavidin beads or column. If, for example the fucose binding agent is attached to an antibody or an Fc of an antibody, the mutated cell population may be depleted of unwanted cells by purification with protein A beads or column.

As mentioned herein above, the cognate binding molecule may itself be attached to a detectable moiety and the depletion may be effected, following addition of the cognate binding molecule, via FACS or MACS.

It will be appreciated that depletion of the unwanted cell populations may be effected in a number of rounds (e.g. two, three or more rounds) of sequential depleting. Further, the depletion steps may comprise a number of rounds of sequential depleting using the same method (e.g. solely FACS based separation) or may combine a number of different methods (e.g. magnetic based separation, followed by fluorescence based separation).

According to one embodiment, the number of rounds of depletion and the specific method is selected such that cells which bind the fucose-binding agent are substantially removed.

The term "substantially removed" is intended to mean removal of at least 50% or more of the particular cell type, such as at least about 75%, about 80%, about 90%, about 95%, or about 97%, including at least 99%, 99.5%, 99.9% or more of the particular cell type.

According to a particular embodiment, cells which bind the fucose-binding agent are substantially removed and only cells which have zero fucose on the cell membrane are retained.

If external fucose is added to the cells after the above removal, various cells which have a certain amount of fucose content, depending on the amount of fucose added, can be obtained.

Thus according to another embodiment, CHO cells which have less than 50% fucose on their cell membrane are obtained as compared with the wild-type cells (i.e. prior to methotrexate treatment).

According to another embodiment, CHO cells which have less than 40% fucose on their cell membrane are obtained as compared with the wild-type cells (i.e. prior to methotrexate treatment).

According to another embodiment, CHO cells which have less than 30% fucose on their cell membrane are obtained as compared with the wild-type cells (i.e. prior to methotrexate treatment).

According to another embodiment, CHO cells which have less than 20% fucose on their cell membrane are obtained as compared with the wild-type cells (i.e. prior to methotrexate treatment).

According to another embodiment, CHO cells which have less than 10% fucose on their cell membrane are obtained as compared with the wild-type cells (i.e. prior to methotrexate treatment).

Following isolation of the cell populations of the present invention, they may be grown in cultures, and in any apparatus that may be used to grow cultures, including fermentors or bioreactors. They may be grown as monolayers or attached to a surface. Alternatively, the isolated cell populations may be grown in suspension.

The cells can be grown in a culture medium that is serum-free. The media can be a commercially available media, such as, but not limited to, ProCHO5 (Lonza, Catalogue #BE12-766Q), CHO DHFR− Medium powder (SAFC Bioscinces, Catalogue #C6614) or Opti-CHO (Invitrogen, Catalogue #12681) supplemented with glutamine, such as 8 mM L-glutamine.

According to one embodiment, the medium is devoid of xeno contaminants i.e. free of animal derived components.

According to another embodiment, the cells are grown in a cell culture under conditions (e.g. medium and space) that allows for indefinite proliferation—i.e. a cell line.

The isolated CHO cells can maintain their variant glycosylation pattern (i.e. low fucose expression) for a high number of passages in culture, i.e. have high stability. It was found according to one embodiment that the modified CHO host cell can maintain its variant glycosylation pattern even after 370 passages.

The present inventors have found that CHO cells selected according to the methods described herein have a particular phenotype, e.g. expression of a mutated GDP-mannose 4,6-dehydratase (GMD), which is responsible for the low fucosylation of their cell membrane.

The cells, following mutagenesis, may comprise at least one allele of GMD having a loss of function mutation.

The term "allele" as used herein, refers to any of one or more alternative forms of a gene locus, all of which alleles relate to a trait or characteristic. In a diploid cell or organism, the two alleles of a given gene occupy corresponding loci on a pair of homologous chromosomes.

A "loss-of-function mutation" is a mutation in the sequence of a gene, which causes the function of the gene product, usually a protein, to be either reduced or completely absent. A loss-of-function mutation can, for instance, be caused by the truncation of the gene product because of a frameshift or nonsense mutation. A phenotype associated with an allele with a loss of function mutation is usually recessive but can also be dominant.

It will be appreciated that the present invention also contemplates cells wherein both alleles of GMD carry a loss-of function mutation. In such instances the GMD may be in a homozygous form or in a heterozygous form. According to this embodiment, homozygosity is a condition where both alleles at the GMD locus are characterized by the same nucleotide sequence. Heterozygosity refers to different conditions of the gene at the GMD locus.

Specifically, the present inventors have found that CHO cells following mutagenesis and the selection procedure of the present invention may express two variant forms of GMD as set forth in SEQ ID NOs: 23 and 24, which correspond to deletions of exons 3 and 4, and 8 and 9 of the GMD gene, respectively.

Thus, according to another aspect of the present invention there is provided an isolated CHO cell being genetically modified to express a mutated GDP-mannose 4,6-dehydratase (GMD) having an amino acid sequence as set forth in SEQ ID NOs: 23 and/or 24.

It was found that the cells of this aspect of the present invention express a functioning fucosyl transferase-8 (Fut8). The functioning Fut8 may be a wild-type Fut8 having a polypeptide sequence as set forth in SEQ ID NO: 29.

In addition, the cells of the present invention express a functioning GDP-keo-6-deoxymannose 3,5-epimerase, 4-reductase (FX). The functioning FX may be a wild-type FX having a polypeptide sequence as set forth in SEQ ID NO: 30.

The present inventors have shown that the CHO cells which have been generated according to the methods described herein can be used to produce glycoproteins, e.g. antibodies or Fc fusion proteins, that can be harvested or collected. The glycoproteins may be secreted, exhibit a variant fucosylation pattern, and/or have a therapeutic use, as further described herein. Such glycoproteins may be e.g. antibodies, such as an antibody with increased ADCC activity as compared to a corresponding antibody produced in an unmodified parental host cell, as further described herein.

"Antibody-dependent cell-mediated cytotoxicity" (ADCC), as used herein, refers to a cell-mediated reaction in which effector cells that express FcRs (e.g. Natural Killer (NK) cells, neutrophils, and macrophages) recognize bound antibody on a target cell and subsequently cause lysis of the target cell. The primary cells for mediating ADCC comprise NK cells, monocytes, and macrophages. NK cells typically express Fc.gamma.RIII predominantly, whereas monocytes express Fc. gamma.RI, Fc.gamma.RII and Fc. gamma.RIII. FcR expression on hematopoietic cells is summarized in Ravetch and Kinet, Annu. Rev. Immunol 9:457-92 (1991).

"Effector cells" are leukocytes which express one or more FcRs and perform effector function(s). Preferably, the cells express at least Fc .gamma.RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein, or may propagate in vitro using known methods in the art.

In one embodiment, an antibody produced from a CHO cell line of the present invention mediates antibody-dependent cell-mediated cytotoxicity (ADCC) in the presence of human effector cells more effectively than a corresponding antibody produced by parental host cells, when the subject antibodies are applied in comparable amounts. Generally, ADCC activity can be ascertained using assays disclosed herein, but other assays or methods for determining ADCC activity, e.g. in an animal model etc, are contemplated. The antibody obtained from the CHO cell line of the present invention iseffective at mediating ADCC than the parent antibody, e.g. in in vivo or in vitro assay systems as further described in U.S. Patent Publication No. 2010/0081150, incorporated herein by reference.

Accordingly, the isolated cell populations or cell lines of the present disclosure previously modified to yield variant fucosylation patterns may be further modified so as to comprise a heterologous polynucleotide sequence. Such sequences may comprise a coding or non-coding region of a gene or gene fragment, messenger RNA (mRNA), transfer RNA, ribosomal RNA, ribozymes, etc. The heterologous sequences may encode a proteinaceous moiety, which refers to proteins, polypeptides, peptides, amino acid sequences, which encompasses polymers of amino acids of any length. The heterologous polynucleotide sequences are typically operatively linked to promoters (i.e. into expression vectors) to enable expression of the recombinant polypeptide.

According to one embodiment, transfection of the CHO cells of the present invention is effected in the presence of exogenous fucose. Contemplated concentrations of fucose include 1-20 μg/ml—e.g. 10 μg/ml.

Figures 44, 45:
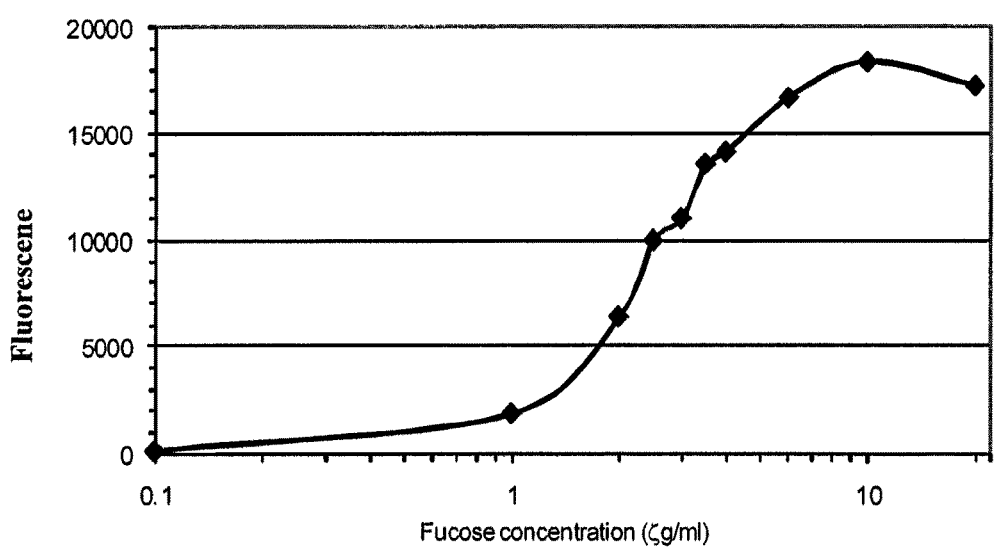
FIG. 44 is a table which provides glycan profiles for Anti-EGFR Fc fractions.
FIG. 45 is a graph illustrating the effect of exogenous fucose had on fucosylation level of ITL-LF2 EGFR mAb transfected cells. ITL-LF2 anti EGFR mAb transfected cells were seeded in ProCHO5 medium in a concentration of 0.2×10⁶ cells/ml with different concentrations of L-fucose and incubated at 37° C. incubator on shaker at 320 rpm with $CO_2$.

As illustrated in FIGS. 45 and 48, the amount of fucosylation of the recombinant polypeptide may be controlled by incubating the transfected cells in fucose. Contemplated concentrations of fucose include 1-10 μg/ml such as 2.5-5 μg/ml—e.g. 3.5 μg/ml.

Thus, there is provided a population of CHO cells which are not fucosylated on their cell membrane and are capable of expressing proteins of varying degrees of fucosylation, the amount of fucosylation being dependent on the amount of fucose in the culture medium at the time of, and following transfection. The amount of fucosylation of the recombinant polypeptide may range from zero to 100%.

Other than containing the necessary elements for the transcription and translation of the inserted coding sequence, expression construct employed can also include sequences engineered to enhance stability, production, purification, yield or toxicity of the expressed peptide. For example, the expression of a fusion protein or a cleavable fusion protein comprising the protein of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the protein and the cleavable fusion protein, the cleavable fusion protein can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265: 15854-15859].

According to one embodiment, purification is carried out in the absence of exogenous fucose.

Preparation of nucleic acids can be carried out by a variety of routine recombinant techniques and synthetic procedures. Standard recombinant DNA and molecular cloning techniques are well known in the art and are described by Sambrook, J., Fritsch, E. F. and Maniatis, T. Molecular Cloning: A Laboratory Manual; Cold Spring Harbor Laboratory Press: Cold Spring Harbor, (1989) (Maniatis) and by T. J. Silhavy, M. L. Berman, and L. W. Enquist, Experiments with Gene Fusions, Cold Spring Harbor Laboratory, Cold Spring Harbor, N.Y. (1984) and by Ausubel, F. M. et al, Current Protocols in Molecular Biology, pub. by Greene Publishing Assoc. and Wiley-Interscience (1987). Briefly, the subject nucleic acids can be prepared genomic DNA fragments, cDNAs, and RNAs, all of which can be extracted directly from a cell or recombinantly produced by various amplification processes including but not limited to PCR and rt-PCR.

As mentioned, the CHO cells of the present invention may be used as host cells for the production of antibodies. The antibodies may be monoclonal or polyclonal.

In some embodiments, the antibody is an inhibitory antibody. Inhibitory antibody may inhibit one or more biological activities of the antigen to which the antibody binds. For example, an inhibitory antibody can downregulate signal transduction of the corresponding antigen by inhibiting the activity of the antigen or inhibit expression of the antigen. In some embodiments, the antibody is a neutralizing antibody. A neutralizing antibody reduces or abolishes some biological activity of a soluble antigen or of a living microorganism, such as an infectious agent. Neutralizing antibodies may compete with the natural ligand or receptor for its antigen. In some embodiments, the antibody is a stimulatory or activating antibody. A stimulatory or activating antibody may be an agonist antibody which may activate signal transduction of the corresponding antigen upon binding of the antigen thereby activating or upregulating the activity of the antigen, or upregulate the expression of the antigen to which the antibody binds.

The term "antibody" as used in this invention includes intact molecules as well as functional fragments thereof, such as Fc fusion proteins, defined as follows: genetically engineered molecules containing the constant region of the heavy chainwhich is linked directly, or via a suitable polypeptide linker, to another polypeptide or protein.

Humanized forms of non-human (e.g., murine) antibodies are chimeric molecules of immunoglobulins, immunoglobulin chains or fragments which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

In one embodiment, the light and heavy chains may be transformed into separate modified host cell cultures, either of the same or of differing species. In an alternative embodiment, separate plasmids for light and heavy chain may be used to co-transform a single modified host cell culture. In another embodiment, a single expression plasmid containing both genes and capable of expressing the genes for both light and heavy chain may be transformed into a single modified host cell culture.

When heavy and light chains are coexpressed in the same host, the isolation procedure is designed so as to recover reconstituted antibody. This can be accomplished by conventional antibody purification procedures such as, for example, protein A-Sepharose, hydroxylapatite chromatography, gel electrophoresis, dialysis, or affinity chromatography.

The recombinant antibodies which can be produced in the cells of the present invention have a variant fucosylation pattern so as to increase the effector function of the antibody. Preferably the recombinant antibodies of the present invention have low fucose levels on the Fc monomer, which is the ADCC relevant fucose residue, thereby increasing the antibody-dependent cellular cytotoxicity (ADCC) activity of an antibody.

According to one embodiment, the antibodies produced are IgG1 or IgG3 type antibodies.

The antibody with variant fucosylation patterns and/or produced by modified CHO host cells of the present disclosure may bind an antigen such as a cancer antigen. The cancer antigen may be selected from the group consisting of HER2, Immunoglobulin epsilon Fc receptor II, Alk-1, CD20, EGF receptor, VEGF receptor, FGF receptor, NGF receptor, PDGF receptor, EpCam, CD3, CD4, CD11a, CD19, CD22, CD30, CD33, CD38, CD40, CD51, CD55, CD80, CD95, CCR2, CCR3, CCR4, CCR5, CTLA-4, Mucin 1, Mucin 16, Endoglin, Mesothelin receptor, Nogo receptor, folate receptor, CXCR4, insulin-like growth factor receptor, Ganglioside GD3, and alpha and beta integrins.

Exemplary antibodies produced in the cells of the present invention include, but are not limited to, adalimumab (Humira®), alemtuzumab (Campath®), basiliximab (Simulect®), bevacizumab (Avastin®), cetuximab (Erbitux®), daclizumab (Zenapax®) dacetuzumab, efalizumab (Raptiva®), epratuzumab, ibritumomab (Zevalin®), tiuxetan, infliximab (Remicade®), muromonab-CD3 (OKT3), omalizumab (Xolair®), palivizumab (Synagis® oregovomab (OvaRex®), rituximab (Rituxan®), trastuzumab (Herceptin®), ocrelizumab, pertuzumab, hu M195Mab, anti-Abeta, anti-CD4, anti-oxLDL, trastuzumab-DM1, apomab, rhuMAb GA101, anti-OX40L, ipilimumab, ustekinumab, golimumab, ofatumumab, zalutumumab, motavizumab, ecromeximab, MDX010, 4B5, TNX-901, IDEC-114 and any Fc antibody fragments specific for antigens and capable of inducing ADCC.

As used herein the term "about" refers to ±10%

The terms "comprises", "comprising", "includes", "including", "having" and their conjugates mean "including but not limited to".

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al. "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials

Cells:
CHO-S (GibcoBRL, Cat. #11619) cells adapted to culture medium Sigma C6614 were established.
CHO-S in C6614 cultured in 200 nM MTX.

CHO-Dukx in C6614.

CHO-S1 in ProCHO-5.

Plasmids: PGL3 anti EGFR mAb EMCV-PAC1-DHFR Tandem—872; pTT5 vector; pCMV-P.

Reagents

AccuPrime Pfx Invitrogen DNA Polymerase Cat No. 12344-024;

Agarose Molecular biology certified, IBI Agarose, Cat # IB70042;

Albumine Bovine Fraction Solution (BSA), 7.5%, Sigma, Cat. # A8412;

Aleuria Aurantia Lectin AAL: 1 mg/ml, cat: L-1390, Vector;

*Aspergillus Oryzae* Lectin AOL, 5 mg/ml Cat. L0169, EY Ampicillin—Sigma Cat. # A9518;

Antibodies for ELISA: Capture: Goat anti-human IgG (H+L), Jackson Immuno Research Cat. #109-005-088 (USA). Detection: Goat anti-human IgG Fc (Fab$_2$), Jackson Immuno Research Cat. #109-036-098 (USA);

Beta actin assay on demand (probe and primers for Q-PCR)—ABI Cat. #RN00667869_m1;

Biotin (EZ-Link® NHS-PEG4-Biotin, No-Weigh™ Format, cat: 21329, Thermo Cat. #21329;

Biotinylated AAL 1 mg active conjugate, Vector, Cat. # B-1395;

Biotinylated MAL 1 mg, EY, Cat. # BA-7801-2;

Bovine serum albumin (BSA), Bovostar. Bovogen Cat. # BSAS.01;

Cell Boost, HyClone, Cat. # SH30866.01;

CHO CD EfficientFeed™ A, Invitrogen, Cat. # A10234-01

CHO CD EfficientFeed™ B, Invitrogen, Cat. # A10240-01

Citric acid, Sigma Cat. # C-1909;

Dextrane sulfate sodium salt, Sigma, Cat. # D4911;

DH5α competent bacteria—Life-Technologies Cat. #18263-012;

DMSO, Merck, Cat. #1.02931.1000;

DNA ladder: 1 kb ladder for DNA—Biolabs Cat No. #3232L;

DNA ladder: 100 bp ladder for DNA—Biolabs Cat No. #3231L;

DTT, Cat: D9779, Sigma;

EDTA, Sigma, Cat. # E7889;

Ethanol Merck Cat. #00983.1000;

EZ-Link® NHS-PEG4-Biotin, No-Weigh™ Format, cat: 21329, Thermo Fisher Scientific Inc USA;

FACS Accudrop Beads, Becton Dickinson, Cat. # MAB345249;

Fucose, Sigma, Cat. # F2252;

Glucose, Sigma, Cat. # G7021;

Glutamine, Biological Industries, Cat. #03-020-1A;

Glutamine, Sigma, Cat. # G5972;

Glycine, Merck, Cat. #4201;

Guanidin-HCl, cat: G3272, Sigma;

Hepes 1M, Invitrogen, Cat. #15630-056;

High Capacity cDNA Reverse Transcription Kit, Applied Biosystems Cat. #4368814;

HTX50, Biological Industries, Cat. #03-085-1C;

Hydrochloric acid, Merck, Cat. # UN-1789 1.00317.2500;

iCE 280 methyl cellulose 1%, Cat.#102220 and 101876, Convergent Biosciences, (Canada);

iCE 280 pharmalyte 3-10, Cat. #10-0456-01, GE Healthcare (Germany);

iCE 280 pI markers 6.14 and 9.5, Cat. #102220 and 101996 respectively, Convergent Biosciences, (Canada);

iCE 280 system suitability kit, Cat. #102093-j, Convergent Biosciences, (Canada);

iCE280 IEF Kit Convergent Biosciences;

IMag buffer, Becton Dickinson, Cat. #552362;

IMag SA Particles Plus—DM, Becton Dickinson, Cat. #557812;

Iodoacetamide, cat: I1149, Sigma;

ITSX100, Invitrogen, Cat. #51500-056;

LB+Ampicillin plates—Hy-Labs Cat. #PD 178;

L-Cysteine, Cat: C7352, Sigma;

LipofectAmine, Invitrogen, Cat #50470;

Maackia amurensis agglutinin 1 mg/ml, cat: L8025, Lot: 036k4075 Sigma;

MAA-FITC, 2 mg in 2 ml buffer, EY, Cat. # F-7801-2;

Maleimide, cat: 129585, Lot: S56783-278 Sigma;

Na$_2$PO$_4$. 2H$_2$O, Merck, Cat. #6580;

NaH$_2$PO$_4$.H$_2$O, Merck, Cat. #6346;

Octet QK System, Kinetics buffer×10 cat #18-5032 Fortebio. Fortebio Inc, USA;

Papain, Cat: P3125, Sigma. Supplied in 0.05 M sodium acetate, pH 4.5 containing 0.05% thymol;

Phenol red, Sigma, Cat. # P0290;

Pluronic F-68, Sigma Cat. # P5556;

Polyethylenimine powder, Linear MW 25000, Polysciences, Cat. #23966;

Protease inhibitor cocktail, Sigma Cat. # P8340;

Protease inhibitor, Sigma, Cat. # P8340;

Protein A Sepharose—Mab Select Xtra, Cat.#17-5269-07, Lot#10011545;

Protein G magnetic beads, Biolabs, Cat. # S1430;

Puromycin, Invivogen, Cat. # Ant-pr 5;

Puromycin, Sigma Cat. # P8833;

Reference sample: ERBITUX® 5 mg/ml solution for infusion from MERCK SERONO lot #7820907;

Restriction enzymes were purchased from New England Biolabs;

R-Phycoerythrin-conjugated Streptavidin (SA-PE) Biolegend, Cat. #405203;

R-Phycoerythrin-conjugated Streptavidin (SA-PE). Jackson, Cat. #016-110-084;

Skim Milk Powder, Fluka. Cat. #70166;

Sodium bicarbonate, Merck, Cat. #6329;

Sodium carbonate, Merck, Cat. #6392;

Sodium chloride, Merck, Cat. #6404;

Sodium Hydroxide pellets, Merck Cat. #1.06498.5000;

SuperScript® III CellsDirect cDNA Synthesis Kit, Invitrogen Cat. #18080-051;

SYBR Safe DNA gel stain, 10000× in DMSO, Invitrogen, Cat # S33102;

TMB solution, Cat: 1928, Savyon Diagnostics;

TransIT-PRO Reagent kit, Mirus, Cat. # Mir5700;

Tris-HCl, cat: T3038, Lot: 037K8402, Sigma;

Tween20, cat: 8.17072, Merck;

Valproic acid sodium salt, Sigma, Cat. # P4543.

Solutions

Biotinylated AAL-SA-PE mixture: biotinylated AAL 20 μg/ml and SA-PE 2 μg/ml in PBS+0.1 pluronic acid;

Bleach 1%—FACS Clean, Becton Dickinson, Cat. #340345;

ELISA assay buffer—1% skim milk powder in PBS;

ELISA blocking solution—1% BSA/0.05% Tween-20 in PBS;

ELISA capture (coating) solution—Goat anti-human IgG (H+L) was diluted 1:900 to final concentration of 2 mcg/ml in 0.1 M Carbonate Buffer pH 9.6;

ELISA standard curve samples: The reference sample Erbitux (EMD Lot-7820907, 5.0 mg/ml) was diluted with assay buffer to 100 ng/ml, followed by two fold serial dilution up to 1.56 ng/ml. Each standard point concentration was prepared a final volume at least of 1 ml;

ELISA wash buffer—0.05% Tween-20 in PBS;

Formulation buffer: Sodium chloride 11.7 gr (100 mM); Citric acid 4.2 gr (10 mM); Glycin 15 gr (100 mM); Sodium hydroxide to pH 5.8 and were completed the volume to 2 liter with WFI;

iCE 280 running stock solution: 70 mcl of 1% methylcellulose, 1 mcl of 6.14 and 9.5 pI marker, 8 mel of pharmalytes (pH 3-10) add 100 ml WFI;

Papain cleavage buffer: 0.1M Tris-HCl, 4 mM EDTA, 5 mM Cystein pH7.6. Cystein should be prepared fresh every time. Dilute Papain to 1 mg/ml with the buffer according to manufacture instructions;

PBS (buffered phosphate saline)—10 mM sodium phosphate, 150 mM sodium chloride, pH 7.2 prepared by 1:10 dilution of 10×PBS;

PBS with 0.1% Pluronic;

PBS, (ITL preparation, BR R0450V01);

PBS-0.05% Tween 20: 0.5 ml Tween 20 were mixed with 1 L PBS×1;

Phosphate buffer 20 mM: pH 7.5: 1.8 gr $Na_2PO_4.2H_2O$ and 1.38 gr $NaH_2PO_4.H_2O$ in 1 L water;

Protein A—Elution buffer: 20 mM Acetic Acid pH=3.2;

Protein A—equilibration/Wash 2 buffer: 50 mM Sodium Acetate, pH=6.8;

Protein A—Wash 1 buffer: 50 mM Sodium Acetate+1.5 M Sodium Cloride, pH=6.8;

Reducing buffer×2: 8M Guanidin-HCl, 100 mM Tris-HCl, 10 mM DTT, pH8.8 (prepare fresh each time).

Culture Media 3.5% Cell boost 6 stock;

CHO Cloning medium, Cat. # C6366, Sigma;

CHO DHFR$^-$ Medium powder, SAFC Bioscinces, Cat. # C6614 (ITL preparation R0461V01);

DMEM-F/12 1:1 X1, Invitrogen, Cat. #21331-020;

FEME medium ((DMEM/F-12 (1:1) (Invitrogen Cat. #32 500_043) supplemented with 8 ml/L ITS-X (Invitrogen, Cat. #51500-056);

Minimum Essential Medium Eagle, Sigma, Cat. 4 M2279;

ProCHO5, Lonza, Cat. # BE12-766Q;

Select CD1000, Becton Dickinson, Cat. #215204;

VPA sodium salt stock, 100 mM.

Disposables 14 ml Centrifuge tubes, Greiner, Cat. #187261;

15 ml Centrifuge tubes, Corning, Cat. #430052;

24 Wells plates, Nunc, Cat. #142475;

5 ml polystyrene round bottom tube, Becton Dickinson, Falcon, Cat. #352054;

5 ml Round bottom tube polystyrene, Becton Dickinson, Falcon, Cat. #352054;

96 Wells plates, Costar, Cat. #3595;

96 Wells Plates, Falcon, Cat. #353072;

ABI PRISM TM Optical Adhesive Covers 100/Pkg, Applied Biosystems, Cat#4311971

Cryo tube vials 2 ml, Grenier, cat.#126-263;

Acrodisc filter 0.2 μm, Gelman, Cat. #4192;

Amicon Ultra 15 ml 10 kDa, Cat: UFC901024, Millipore;

Amicon Ultra 3 kDa, Cat: UFC900324, Millipore;

Amicon ultra, centrifugal filter unit, Millipore, Cat. # UFC801024;

Cryo Freezing 1° C. container, Nalgene, Cat. #5100-0001;

Disposable 0.22μ filter for PBS or water sterilization, Nalgene, Cat. 1270020;

Disposable 0.2μ filter for ACFM sterilization (GP express plus membrane), Millipore, Cat. # SCGPU05RE or SCGPU11RE;

Disposable 0.45μ filter for FACS clean sterilization, Nalgene, Cat. #4500045;

Disposable 40μ cell strainer sterile, Becton Dickinson, Falcon, Cat. #352340;

Disposable 5 ml polystyrene tube with cell strainer cup 35μ, Becton Dickinson, Falcon, Cat. #352235;

Disposable 70μ (or 35μ) sterilefilter cup Filcon, Becton Dickinson, Falcon, Cat. #340634;

Disposable filter 10μ Cup filcon, Becton Dickinson, Cat. #340732;

Disposable filter 30μ Cup filcon, Becton Dickinson, Cat. #340625;

DynaMag, Dynal, Invitrogen, Cat. #123.01D;

DynaMag, Dynal, Invitrogen, Cat. #123.21D;

ELISA, microtiter plates MaxiSorp F96, cat: NUNC;

Erlenmeyer 1000 ml, Triforest, Cat. # TF FPC1000S;

Erlenmeyer flasks: 125 ml, Corning, Cat. # WI-431143, 250 ml, Corning, Cat. # WI-431144, 500 ml, Corning, Cat. # WI-431145, 2 L, Corning, Cat. # WI-431255;

FACS tubes, Falcon, Cat. #352235 with blue filter cap;

FACS tubes, BD Falcon, Cat. #352235;

Filter 10" 0.1 μm, Durapore, Millipore, Cat. # MILLIPAK200;

Filter tubes 50, TPP, Cat#87050;

iCE 280 Capillary Cartridge, Cat: FC Coating (PN: 101700), Convergent Biosciences;

iCE 280 microinjector transfer capillary, Cat:PN:102019, Convergent Biosciences;

IMagnet, Becton Dickinson, Cat. #552311;

Kova Glasstic Slide 10 with Grids, Hycor, Cat. 87144;

Microcentrifuge tubes (1.7 ml), Costar, Cat. #3207;

Octet QK System, microplate black 96 wells cat:655209, Greiner bio-one, Germany;

Optical 96-Well Fast Thermal Cycling Plate with barcode 20/Pkg, Applied Biosystems, Cat#4346906Pipet tips, Sorenson, Cat. 1114200 and 14220;

Pipet tips, Sorenson, Cat. #14200 and 14220;

Pipette tips 0-200 μl, Costar, Cat. #4864;

Slide—A Lyzer Dialysis cassette G2 2 kDa: cat: 87718, Thermo;

SnakeSkin Dialysis tubing 10 kDa, cat: 68100, Lot: JJ127549, Thermo HiTrap MabSelect Xtra 1 ml, Cat: 28-4082-58, GE;

Stericup 1 L filter unit 0.1 μm, Millipore, Cat. # SCGPU05RE;

Stericup 1 L filter unit 0.2 μm, Millipore, Cat. # SCGPU11RE;

Steriflip Filter Unit 50 ml, 0.22 μm, Millipore, Cat. # SCGP00525;

Sterile 24-well plates, Nunc, Cat. #143982;

Sterile 6-well plates, Costar, Cat. #3506;

Sterile centrifuge tubes: 15 ml, Becton Dickinson, Falcon, Cat. #2097 and Corning, Cat. #430055, 50 ml Corning, Cat. #430290, 250 ml Corning, Cat. #430776, 500 ml Corning, Cat. #431123;

Sterile FACS tubes, Becton Dickinson, Falcon, Cat. #352054;

Sterile pipettes: 10 ml Sterillin Cat. #47110, 1 ml Sterillin, Cat. #40105, 2 ml Sterillin, Cat. #40102, 5 ml Corning, Cat. #4011, 50 ml Corning, Cat. #4501, 25 ml Falcon, Cat. #35-7525;

Sterile tissue culture flasks: 25 cm2, (T-25), Nunc, Cat. #163371;

Streptavidin Biosensor tips cat: 18-5019, Fortebio Inc, USA;
Syringe 2.5 ml sterile, Medi-Plus, Cat.;
TCF 175 cm², Nunc, Cat#156502;
TCF 25 cm², Nunc, Cat#136196;
TCF 80 cm², Nunc, Cat#153732.

Equipment

AKTA explorer 100, cat: 18-1112-41, GE (Germany);
Cellavista—Innovatis, Roche;
Centrifuge—Cat. #5417R—Eppendorf;
Centrifuge—Type RC 3C Plus—Sorvall (USA);
Circulating water bath, Model F3/K, Haake (Finland);
Conduct meter ORION, Model 150, ORION Research Inc.;
Coulter counter—Model Z1, Coulter Electronics (England);
Cryo Freezing 1° C. container, Nalgene, Cat. # No. 5100-0001;
ELISA plate reader Sunrise basic, Cat. #16039400, TECAN;
ELISA Plate Washer Columbus, Cat. #6040834, TECAN;
ELISA Robot Genesis RSP 150/8, Cat. #611408, TECAN;
ELISA, iEMS incubator, Cat. #5112200, Thermo;
Eppendorf centrifuge, series 5417R, Eppendorf (Germany);
FACSAria Flow Cytometer, Beckton Dickinson;
Finnpipette, Cat. #4540000 Labsystems (Finland);
GE Fanuc series 90-70 programmable controller—General Electric Ltd. (USA);
GeneAmp® PCR System 9700, PE Applied Biosystems (USA);
Horizen Gel electrophoresis System, GIBCO-BRL Horizon 58, Cat. #41060;
iCE 280 Imaged Capillary Electrophoresis Analyzer, Cat. #1241, Convergent Biosciences;
iCE 280 PrinCE MicroInjector, Cat. #5418074067, Convergent Biosciences;
iCE 280 Software iCE280 CFR software v.23.6 Convergent Biosciences;
Image master VDS, Cat. #80-6254-80 Pharmacia (Sweden);
Incubation Shaker Box, CERTOMAT® BS-T, B. Braun Biotech International (Germany);
Incubator 37° C. 5% CO2, temperature and CO2 controlled, Tuttnauer (Israel);
Incubator—Shake "n" stack, Hybaid, Cat # HBMOVC5T220 (Hybridization oven);
Laminar Flow Hood (LFH) class 100—Israflow (Israel);
Light microscope—Model TMS No. 301070—Nikon (Japan);
Microplate incubator/shaker, iEMS, ThermoLabsystem (Finland);
Microplate Washer, Cat. # WW015, Applied Quality Services LTD (UK);
Microwave oven—Crystal 17 L;
Octet QK System, Data Acquisition Software 6.3 version, Fortebio Inc, USA;
Octet QK System, Data Analysis software 6.3 version, Fortebio Inc, USA;
Octet QK System, Fortebio Inc, CA, USA;
Orbital Platform Shaker with a shaking amplitude (orbit) of 25 mm New Brunswick Scientific (USA);
Peristaltic pumps—Watson Marlow 503S or 505U (United Kingdom);
pH meter, series PHM210, Radiometer (Denmark);
Plate washer (SLT 96PW) TECAN;
Platform rocking shaker—Hoefer "Red-Rocker" PR50-250V (Pharmacia biotech.);
Power supply, Cat. # PS500XT, Hoefer scientific instruments (USA);
Refrigerated centrifuge, Multifuge 3 S-R, Heraeus;
Refrigerated Incubator Shaker, Innova 4230, New Brunswick Scientific (USA);
Robotic sample processor, Model RSP 150/8 Genesis, TECAN, (Switzerland);
Shaker, Rotamax, Series #120 Heidolph (Germany);
Software—WIZCON-PC Soft International Ltd. (Israel);
StepOnePlus™ Real-Time PCR System, Applied Biosystems, Cat#4376600;
UV table, BTS 20.MS, Uvitec, Cat. # M023641;
Water bath—Temp. controller, Polyscience, Model 9106

General Methods

Abbreviations

AAL—Aleuria aurantia lectin
ACF—Animal component free
ACFM Animal Component Free Medium
ADCC—Antibody-dependent cell-mediated cytotoxicity anti EGFR mAb
CHO—Chinese Hamster Ovary
DHFR— Dihydrofolate Reductase
DMEM—Dulbecco's Modified Eagle's Medium
DMSO Dimethylsulfoxid
DTT—Dithiothreitol.
EDTA Ethylenediaminetetraacetic acid.
EGFR Epidermal Growth Factor Receptor
ELISA Enzyme-Linked Immunosorbent Assay
EMCV—encephalomyocarditis virus
Fab—The CH1 and $V_H$ portion of the heavy chain and the light chain of the IgG1.
FACS—Fluorescence Activated Cell Sorter
Fc—The CH3 and CH2 portions of the IgG1 heavy chain.
F-SA—Fluorescent streptavidin
Fut8—fucosyl transferase 8
FX GDP-keo-6-deoxymannose 3,5-epimerase, 4-reductase
GFT—GDP-fucose transporter
GMD—GDP-mannose 4,6-dehydratase
GOI—Gene of interest
HC—heavy chain
hCMV-IE—Human Cytomegalovirus immediate early promoter
HRP Horse Radish Peroxidase
ICE Imaged capillary electrophoresis
IgG1 Immunoglobulin type G1.
IRES—Internal ribosome entry site
LC—light chain
MAA—Maackia amurensis lectin
MCB—Master cell bank
mCMV—murine cytomegalovirus promoter
MFI—Mean Fluorescence Intensity
MS—Mass sperctrometry
MTX—Methotrexate
NK—Natural killer cells
pA—polyadenylation
PAC—Puromycin N-Acetyl Transferase
PBS Phosphate Buffered Saline
PCD—Picogram per Cell per Day
PCR—Polymerase Chain Reaction
PDL—Population doubling level
PDT—Population doubling time POI—Protein of interest
PreMCB—Pre master cell bank
RE—Restriction enzyme(s)
RT—Room temperature
SA—Streptavidin
SA-PE R-Phycoerythrin-conjugated streptavidin
SP—Signal Peptide
SV40—simian virus 40
TM—Trans membrane peptide
TMB 3,3',5,5'-Tetramethylbenzidine
VPA—valproic acid Incubation of CHO-S Cells in the Presence of MTX:

CHO-S cells in C6614 were seeded at $0.2 \times 10^6$ cells/ml in 100 nM MTX and propagated for ten days until viability exceeded 90%. Then the cells were transferred to 200 nM MTX for 27 days and subsequently the cells were frozen in the presence of 200 nM MTX. For isolation of zero fucose expressing cells the cells were thawed in medium that did not contain MTX.

Selection of Low Fucose Cells with Streptavidin Magnetic Beads:

MTX treated CHO-S cells were labeled with biotinylated AAL or AOL and mixed with streptavidin linked to magnetic beads. The cells were separated with a magnet and cells in suspension, which did not attach to the magnet (i.e. had low fucose level on their surface), were further propagated. This procedure was performed twice and then the cells were sorted by FACS.

$50 \times 10^6$ MTX treated CHO-S cells were collected and washed in PBS+0.1% Pluronic acid (Pluronic F-68, Sigma Cat. # P5556). Then cells were resuspended in 5 ml of biotinylated AAL (Vector, cat. B-1395, Lot# U0922) at a concentration of 20 µg/ml or with AOL (Cat. L0169, EY) at a concentration of 5 µg/ml in PBS+0.1% Pluronic acid for 30 min at RT. The stained cells were washed with PBS+0.1% Pluronic acid prior to addition of 250 µl BD IMag SA Particles Plus—DM (BD, Cat. #557812) and incubation of another 30 min at RT. Then, 2.25 ml of PBS+0.1% Pluronic acid+0.5% BSA were added. The beads were divided into three 5 ml tubes. The tubes were placed on BD IMagmet (BD, Cat. #552311) and left for 8 minutes. The supernatant was aspirated and transferred to a new 15 ml tube. This step was done twice and the aspirated supernatant was combined. The supernatant was divided again into 5 ml tubes and placed on the BD IMagmet (BD, Cat. #552311) for 8 minutes. The supernatant was collected, centrifuged and seeded in C6614 medium (CHO DHFR⁻ Medium powder, SAFC Bioscinces Cat. # C6614) (ITL preparation R0461V01). The cells were propagated and then another round of separation with the beads was performed.

Following incubation with the lectin the cells' viability was 83% when incubated with AAL and 89% when incubated with AOL. Typical viability of cells following incubation with PBS is 85-95%.

Sorting of Low Fucose Cells by FACS

A. Sorting Following Separation with Magnetic Beads:

Cells, after two rounds of separation with magnetic beads, were subjected to FACS sorting for cells having low fucose levels on their cell surface. $40 \times 10^6$ cells were washed in cold PBS+0.1% Pluronic acid, centrifuged, resuspended in 10 ml biotinylated AAL or AOL+SA-PE mixture 20 µg/ml and transferred to a T80 flask for incubation of 30 minutes with shaking at 45 rpm at 37° C. The cells were centrifuged, washed in cold PBS+0.1% Pluronic acid, centrifuged twice and resuspended in PBS+0.1% Pluronic acid to a final concentration of $10 \times 10^6$ cells/ml. The lowest fluorescent fraction of the population (1.5%), were sorted by FACS into 2 ml of Sigma C6614 SFM+HT (Biological Industries Cat. #03-085-1C)/tube, centrifuged, resuspended in 1.5 ml of Sigma C6614 SFM+HT/tube and seeded into a well in a 6 well plate and propagated.

B. Sorting of Low Fucose Cells—Four Rounds:

$100 \times 10^6$ cells were washed in cold PBS+0.1% Pluronic acid, centrifuged, resuspended in 10 ml biotinylated AAL (20 µg/ml)+SA-PE (1:100) mixture in PBS+0.1% pluronic acid and transferred to T80 flask for incubation of 30 minutes with shaking at 45 rpm 37° C. The cells were centrifuged, washed in cold PBS+0.1% pluronic acid, centrifuged twice and resuspended in PBS+0.1% Pluronic acid to obtain cell concentration of $10 \times 10^6$/ml and filtered into FACS tubes. Following incubation with the AAL the cells' viability was 81%. Typical viability of cells following incubation with PBS is 85-95%. The lowest fluorescent fraction (0.2% in the first sort, 0.07% in the second, 1% in the third and 2% of the fourth) of the population were sorted by FACS into 2 ml of Sigma ProCHO5 SFM+HT/tube, centrifuged, resuspended in 1 ml (in the first and second sorts) 3 ml (in the third and fourth sorts) of ProCHO5+HT/tube, seeded into a well in a 24 well plate (in the first and second sorts), T25 flask (in the third and fourth sorts) and propagated.

Analysis of Fucose Level on Cells' Membrane by FACS:

$2 \times 10^6$ cells were washed in PBS+0.1% Pluronic acid, centrifuged, resuspended in 500 µl biotinylated AAL (Cat. B1395, Vector) (diluted to 20 µg/ml) or AOL (Cat. L0169, EY) (diluted to 5 µg/ml)+SA-PE (Cat. 40250, Biolegend) (diluted to 2 µg/ml) mixture in PBS+0.1% pluronic acid and transferred to 24 well plates for incubation of 30 minutes with shaking at 37° C. The cells were resuspended thoroughly and transferred to 15 ml tubes. 10 ml PBS+0.1% pluronic acid were added and the cells were mixed, centrifuged and washed again. The pellet was resuspended in 0.5 ml of PBS+0.1% Pluronic acid/tube and filtered into FACS tubes for analysis according to the fluorescence of the cells.

Analysis of Sialic Acid Content on Cells' Membrane by FACS:

$2 \times 10^6$ cells were washed twice in PBS+0.1% Pluronic acid, centrifuged, re-suspended in 500 µl MAA-FITC (diluted to 50 µg/ml) in PBS+0.1% pluronic acid and transferred to 24 well plates for incubation of 30 minutes with shaking at 25° C. The cells were re-suspended thoroughly and transferred to 15 ml tubes. 10 ml PBS+0.1% pluronic acid were added and the cells were mixed, centrifuged and washed again. The pellet was re-suspended in 0.5 ml of PBS+0.1% pluronic acid/tube and filtered into FACS tube for analysis according to the fluorescence of the cells.

Addition of Exogenous Fucose to ITL-1f2 Cell Culture:

ITL-LF2 cells, either before or after transfection with anti EGFR mAb, were seeded in ProCHO5 medium at a concentration of $0.2 \times 10^6$ cells/ml with different concentrations of L-fucose (Sigma Cat. #F2252) and incubated at 37° C. on a shaker at 320 rpm with $CO_2$. After 4 days, cell samples were taken for FACS analysis according to the fluorescence of the cells (as described herein below). In addition, crude harvest samples from anti EGFR mAb transfected cells were analayzed by FACS.

Preparation of Pre-Master Cell Banks:

Cell cultures for cell freezing, were expanded in Erlenmeyers. The required amount of cells was centrifuged and resuspended in cryopreservation medium composed of 92.5% of a 1:1 mixture of fresh ProCHO5 medium+HT and conditioned medium (from exponentially growing ITL-LF2 host cells) and 7.5% DMSO. Sixty vials were frozen from each clone in each Pre-Master Cell Bank (pre-MCB), $10 \times 10^6$ cells per vial in 1.5 ml per vial. Cells were frozen at −80° C. in Cryo Freezing 1° C. container, (NALGENE, Cat. #No. 5100-0001), and 24 hours later transferred to storage in liquid nitrogen vapor.

Cell Bank Testing:

Viability of cells in frozen ampoule in the pre-MCB of ITL-LF2 cells was tested 11 days after pre-MCB preparation. One ampoule was thawed and viability was determined immediately after thawing. Cells were propagated along three growth cycles and viability was determined after the third cycle.

Sterility testing was performed by the direct transfer or immersion technique. Cells were also tested for *mycoplasma*.

Cloning by FACS ACDU:

Cloning by the Automated Cell Deposition Unit (ACDU) device of the FACSAria cell sorter, of cells growing in ProCHO5+HT was performed by the ACDU, in the "Single Cell" precision mode, into 96 well plates containing 200 μl/well of 80% C6366+20% ProCHO5 ACFM mixture. Cells' concentration was $0.4 \times 10^6$ cells/ml. Plates were photographed by Cellavista at the day of cloning (day 0) and then eighth days later. Several clones were picked, propagated and then transferred to T25 flasks containing 4 ml of 50% Sigma C6366 and 50% ProCHO5 mixture. ProCHO5 was added gradually during cell propagation. These cells were analyzed for mRNA characterization.

RNA Extraction from Cells:

Total RNA was isolated from cells with Rneasy kit (Qiagen Cat. #74104) according to manufacturer instructions.

RT-PCR for Detection of Fucose Pathway Genes:

cDNA was prepared from total RNA extracted from CHO-S or ITL-LF2 cells utilizing Invitrogen SuperScript III Kit (Cat. #18080-051) and the Oligo dT primers provided in the kit. PCR was then preformed using gene specific primers. Primers were synthesized at Sigma Aldrich. Sequences of primers are detailed in Table 1, herein below. The resulting bands were analyzed on agarose gels and compared to DNA size markers.

TABLE 1

| Construction of vector | Template used | Fragment obtained | 5' primer No. | Sequence* | 3' primer No. | Sequence* |
|---|---|---|---|---|---|---|
| MB-127 (pTT5-anti EGFR mAbanti EGFR mAb-HC) | PGL3 anti EGFR mAb EMCV-PAC1-DHFR Tandem - 872 | HindIII-anti EGFR mAbHC-NotI | 690-36 | SEQ ID NO: 1 | 691-38 | SEQ ID NO: 2 |
| MB-128 (pTT5-anti EGFR mAb-LC) | PGL3 anti EGFR mAb EMCV-PAC1-DHFR Tandem - 872 | HindIII-anti EGFR mAbLC-NotI | 692-36 | SEQ ID NO: 3 | 693-32 | SEQ ID NO: 4 |

Q-PCR (Real Time PCR) for Evaluation of Fucose-Pathway mRNA Expression Levels:

cDNA was prepared utilizing the Applied Biosystems high capacity cDNA reverse transcriptase Kit and random primers supplied in the kit (Applied Biosystems Cat. #4368814).

Gene specific primers and TaqMan® MGB probes were synthesized at Applied Biosystems. Sequences of primers and probes are detailed in Table 2, herein below.

TABLE 2

| Gene | Probe | 5' primer | 3' primer |
|---|---|---|---|
| Alpha 1,6 fucosyltransferase (Fut8) | SEQ ID NO: 5 | SEQ ID NO: 6 | SEQ ID NO: 7 |
| GDP-4-keto-6-deoxy-D-mannose epimerase-reductase (Fx) | SEQ ID NO: 8 | SEQ ID NO: 9 | SEQ ID NO: 10 |
| GDP-mannose 4,6-dehydratase (GMD)- 5-6 exon primers | SEQ ID NO: 11 | SEQ ID NO: 12 | SEQ ID NO: 13 |
| GDP beta L fucose pyrophosphorylase (GFPP) | SEQ ID NO: 14 | SEQ ID NO: 15 | SEQ ID NO: 16 |
| GDP-fucose transporter (GFT) | SEQ ID NO: 17 | SEQ ID NO: 18 | SEQ ID NO: 19 |
| VEZT | SEQ ID NO: 20 | SEQ ID NO: 21 | SEQ ID NO: 22 |

Q-PCR was performed in the following manner:

For each reaction 5 μl of prepared cDNA was added to a mix containing: TaqMan™ gene expression master mix, forward and reverse primers & TaqMan™ MGB probe in a final volume of 13 μl.

Q-PCR was run on the StepOnePlus™ Real Time PCR machine in the "fast" mode and results analyzed utilizing the StepOnePlus™ and DataAssist v2.0 softwares.

DNA Sequencing of cDNA Fragments and Plasmids:

DNA sequencing was performed by the fully automated 16 Capillary ABI Prism 3100 Genetic Analyzer. The sequences were analyzed in-house utilizing the Sci-Ed General software (Clone manager software, version 7.01 and Align plus 5, version 5.01).

Construction of DNA Expression Vectors:

All vectors were constructed utilizing standard molecular biology techniques.

Preparation of Plasmid DNA:

Plasmid DNA was isolated using QIAGEN Hispeed plasmid Maxi Kit according to the procedure described by the manufacturer. For stable transfections DNA was linearized by specific restriction enzymes and sterilized by DNA precipitation in ethanol. Transient transfections were performed with circular DNA.

Stable Transfections of ITL-LF2 and CHO-S Cells:

ITL-LF2 cells were adapted to C6614 serum free medium (CHO DHFR⁻ Medium powder, SAFC Biosciences Cat. # C6614). Cells were grown in suspension in 50 ml tubes (Filter tubes 50, TPP, Cat#87050), 37° C., humidified and shaken at 320 RPM. Two days prior to transfection, 100 ml of the cells were seeded at a concentration of $0.5 \times 10^6$ cells/ml in a 500 ml Erlenmeyer (Corning, Cat. WI-431145).

The cells were transfected with PGL3 anti EGFR mAb EMCV-PAC1 DHFR Tandem-872 vector containing the anti EGFR mAb coding sequence by LipofectAmine (GibcoBRL Cat. #18324-020). On the day of transfection, the cells in replicates were washed; resuspended and $10 \times 10^6$ cells were seeded in 4 ml MEM (Sigma, Cat. # M2279) per T-25 flask (Nuns Cat. #163371). For each transfection with single plasmid, 20 µg linearized PGL3 anti EGFR mAb EMCV-PAC1 DHFR Tandem-872 vector were used. The final DNA volume was adjusted to 100 µl in MEM. Subsequently, 100 µl LipofectAmine were added and incubated for 45 minutes at room temperature. The DNA-LipofectAmine mix was then added to the cells and incubated for 4 hours at 37° C., 5% $CO_2$ in a shaking incubator at 50 RPM. At the end of this incubation period, the cells were spun down and medium was replaced with 8 ml fresh 50% C6614 (Sigma) and 50% C6366 (Sigma) supplemented with 13.6 mg/L Hypoxanthine/3.9 mg/L thymidine (HT, Biological Industries Cat. #03-085-1C) and 10 µg/ml fucose (Sigma, Cat. #F2252).

The flasks were incubated at 37° C. in a shaking incubator at 50 RPM for 72 hours. Then the cells were collected, centrifuged and resuspended in 10 ml 50% C6614+50% C6366 media supplemented with 10 mg/ml fucose and 5-10 µg/ml Puromycin (for the different replicates) and returned to the original T-25 flask. Under these selective conditions, only cells expressing the PAC gene could survive. Following replicate pool recovery, C6614 medium+10 µg/ml fucose was added gradually. When pools recovered completely, the cells were seeded in fresh C6614 medium without fucose. Then cells were transferred to ProCHO5 medium and fucosylation level on the cells' membrane was detected as described herein below.

CHO-S cells were cultured in ProCHO5 serum free medium (Lonza, Cat. #BE12-766Q) supplemented with Hypoxanthine 13.61 mg/L and Thymidine 3.88 mg/L (HT× 1, Biological Industries Cat. #03-085-1B). Cells were grown in suspension in filter tubes 50 ml Bioreactor (TPP, Cat#87050), 37° C., humidified and shaken at 320 RPM. Two days prior to transfection, the cells were seeded at a concentration of $0.2 \times 10^6$ cells/ml in 500 ml shake flask Erlenmeyers, with filter cap (Corning, Cat. #431145). On the day of transfection, the cells were centrifuged and $10 \times 10^6$ cells were seeded in 4 ml MEM (Sigma, Cat. # M2279) in T25 flasks (Nunc, Cat. #163371). For each transfection with single plasmid, 20 µg linearized vector (PGL3 anti EGFR mAb EMCV-PAC1 DHFR Tandem-872) were used. The final DNA volume was adjusted to 100 µl in MEM. Subsequently, 100 µl LipofectAmine (GibcoBRL Cat. #18324-020) were added and incubated for 45 minutes at room temperature. The DNA-LipofectAmine mix was then added to the cells and incubated for 4 hours at 37° C., 5% $CO_2$ in a shaking incubator at 50 RPM. At the end of this incubation period the cells were spun down and medium was replaced with 8 ml fresh ProCHO5 (Lonza, Cat #BE12-766Q) supplemented with dextrane sulfate 0.1 mg/ml, Hypoxanthine 27.22 mg/L and Thymidine 7.76 mg/L (HT×2, Biological Industries Cat. #03-085-1B) in Erlenmeyer 125 ml with filter cap (Corning, Cat. #431143). The flask was incubated at 37° C. in a shaking incubator at 125 RPM for 72 hours. Then, the cells were collected, centrifuged and resuspended in 20 ml ProCHO5 medium supplemented with 25 µg/ml puromycin (Invivogen, Cat. # ant-pr-1), under these selective conditions, only cells expressing the PAC gene could survive.

Transient Transfections of ITL-LF2 Cells:

Two days prior to transfection, cells propagated in ProCHO5 were seeded at a concentration of $0.5 \times 10^6$ cells/ml in 250 ml in a 1000 ml Erlenmeyer (TRIFOREST, Cat. # TF FPC1000S) in order to reach the approximate density of $2.5-3.0 \times 10^6$ cells/ml after 2 days.

Two transfection protocols were used:

1. Transfection in Medium Containing ProCHO5 (Lonza)

On transfection day, 37.5 µg DNA, (18.75 µg each of the HC+LC plasmids) were diluted in 2.5 ml FEME medium ((DMEM/F-12 (1:1) (Invitrogen Cat. #32 500_043), 29 mM NaHCO3, 10 mM HEPES, 5 g/l D-Glucose and 7.5 mM L-Glutamine) in 15 ml tube (Corning, Cat. #430052) Er125 flask was filled with 10 ml initial volume of FEME medium (DMEM/F-12 (1:1) (Invitrogen Cat. #32 500_043) supplemented with 8 ml/L ITS-X (Invitrogen, Cat. #51500-056); 187.5 µg PEI stock (Polysciences inc., Cat. #23966), were added to the DNA+FEME medium (DNA:PEI 1:5), the reagents were mixed on vortex for 10 seconds and incubated for 10 seconds at room temperature. $60 \times 10^6$ live cells were centrifuged in 50 ml tubes. The pellet was re-suspended gently with the transfection mixture and transferred into the 125 ml Erlenmeyer following by incubation for 180' minutes in $CO_2$ shaking incubator at 37° C. in 160 pm. 12.5 ml of ProCHO5 medium were added to reach final concentration of $2.4 \times 10^6$ cells/ml in 25 ml culture.

Twenty four hours post transfection, CHO-S transfected cells were supplemented with 100 µl (final concentration 0.5 mM) of valproic acid (VPA) sodium salt stock 100 nM (Sigma, Cat. #P4543) and 2 ml of 3.5% Cell boost (HyClone Cat# SH30866.01). ITL-LF2 cells were supplemented with 100 µl (final concentration 0.5 mM) of valproic acid (VPA) sodium salt stock 100 nM (Sigma, Cat. # P4543) and the incubation temperature was reduced to 31° C.

After 6 days of incubation a sample of cell suspension was taken for cell count and viability. Following centrifugation the supernatant was taken for evaluation of transient expression in ELISA test.

2. Transfection in a Second Medium.

Production of Anti-EGFR mAb by ITL-LF2 and CHO-S Cells:

Cells at a concentration of $0.5-2 \times 10^6$ were seeded in 200-600 ml ProCHO5 containing dextrane sulphate in 1 or 2 L Erlenmeyer flasks and cultured for 4 days at 37° C. on a shaker incubator at 320 rpm. The harvest was centrifuged and included through 0.22 µm filter. A protease inhibitor cocktail (Sigma, Cat. # P8340) was subsequently added (1 ml for 1 L of culture). The harvest was kept frozen at −80° C. until the beginning of purification process.

Analysis of Fucose Level of Crude Harvest Sample or Purified Recombinant Protein by FACS:

Protein G magnetic beads (Cat. S1430S, Biolabs) were thoroughly re-suspended and 25 µl were transferred into 2 ml tubes at room temperature. The tube was placed on a magnet for 1 minute and the supernatant was aspirated. 0.5 ml of 20 mM phosphate buffer was added in order to re-suspend the Protein G beads. This washing step was repeated once more.

100 µl of sample antibody (25-37 µg/ml either crude harvest or purified protein) were added to the magnetic beads containing tubes. The mixture was incubated for 30 min at 37° C. and placed on the magnet in order to discard the supernatant. The beads were washed two times with 0.5 ml of 20 mM phosphate buffer and the buffer was aspirated on the magnet. The beads bound to the sample antibodies were resuspended in 0.5 ml of biotinylated AAL-SA-PE mixture (biotinylated AAL Vector, Cat. B1395, 20 µg/ml and SA-PE. BioLegend, Cat. 40520, 0.2 µg/ml diluted to 2 µg/ml in PBS+0.1% pluronic acid) and transferred into 24 well plates (Nunc, Cat. 142475) covered with aluminum foil and incubated 30 min shaking at 80 rpm 37° C. The mixture was resuspended thoroughly and transferred to 15 ml tubes (Corning, Cat. 430052) with 10 ml PBS+0.1% pluronic acid. Then two rounds of washing were performed by addition of 10 ml PBS+0.1% pluronic acid centrifugation and removal of the supernatant. The pellet was resuspended in 0.5 ml PBS+0.1% pluronic acid, filtered through a FACS tube (Falcon, Cat. 352235) and analyzed by FACS.

Analysis of Sialic Acid Level of Crude Harvest Sample or Purified Recombinant Protein by FACS:

Protein G magnetic beads (Cat. S1430S, Biolabs) were thoroughly re-suspended and 25 µl were transferred into 2 ml tubes at room temperature. The tube was placed on a magnet for 1 minute and the supernatant was aspirated. 0.5 ml of 20 mM phosphate buffer was added in order to re-suspend the Protein G beads. This washing step was repeated once more.

100 µl of sample antibody (25 µg/ml either crude harvest or purified protein) were added to the magnetic beads containing tubes. The mixture was incubated for 30 minutes at room temperature and placed on the magnet in order to discard the supernatant. The beads were washed two times with 0.5 ml of 20 mM phosphate buffer and the buffer was aspirated on the magnet. The beads bound to the sample antibodies were resuspended in 0.5 ml of MAA-FITC (2 mg in 2 ml, EY, Cat. F-7801-1 diluted to 25 µg/ml in PBS+0.1 pluronic acid) and transferred into 24 well plates (Nunc, Cat. 142475) covered with aluminum foil and incubated 30 minutes whilst shaking at 80 rpm at room temperature. The mixture was resuspended thoroughly and transferred to 15 ml tubes (Corning, Cat. 430052) with 10 ml PBS+0.1% pluronic acid. Then two rounds of washing were performed by addition of 10 ml PBS+0.1% pluronic acid centrifugation and removal of the supernatant. The pellet was resuspended in 0.5 ml PBS+0.1 pluronic acid, filtered through a FACS tube (Falcon, Cat. 352235) and analyzed by FACS.

ELISA for Anti-EGFR Antibody:

ELISA assay was used to determine the concentration of human antibody in the test samples. The assay was performed as described below.

Microtiter plates were coated with 2 µg/ml of goat anti-human IgG (H+L) in 0.1 M Carbonate Buffer pH 9.6 and incubated overnight at 4° C. The plates were washed four times with washing buffer (0.05% Tween-20 in PBS). The plates were then blocked with blocking buffer (1% BSA in PBS-T 0.05%), 200 µl/well, for 1 hour at RT. After blocking, the plates were washed four times with washing buffer (0.05% Tween-20 in PBS). Coated plates were used immediately after preparation, or stored at −20° C. until used (within 6 weeks). The samples, standard curve and check samples were added to the plates (100 µl/well) and incubated at 37° C. for 1 hr. Plates were washed again four times with wash buffer and 100 µl aliquots of the HRP-conjugated goat anti human IgG Fab diluted to 8 ng/ml in assay buffer (1% skim milk powder in PBS) and incubated at 37° C. for 1 hour. Plates were washed again four times with wash buffer and 100 µl of substrate solution (TMB) were added and incubated for approximately 10 minutes at RT. The reaction was stopped by adding 100 µl 1N HCl to each well. The absorbance was measured at $A_{450}$ nm in an ELISA reader. Standard solutions were prepared by serial dilutions of the reference sample anti-EGFR (ERBITUX from MerckSerono) to give a standard curve range from 100 to 1.56 ng/ml in assay buffer. A sample of crude product from pool 2390 (produced at ITL) was used as a check sample. The Magelan 5 software calculated the optical data results. The four-parameter logistic equation was used and the results of the unknown samples were automatically interpolated from the standard curve expressed in ng/ml. Dilution of samples, preparation of standard curve, distribution of samples on the plate was performed by a Robotic sample processor.

Figure 1:
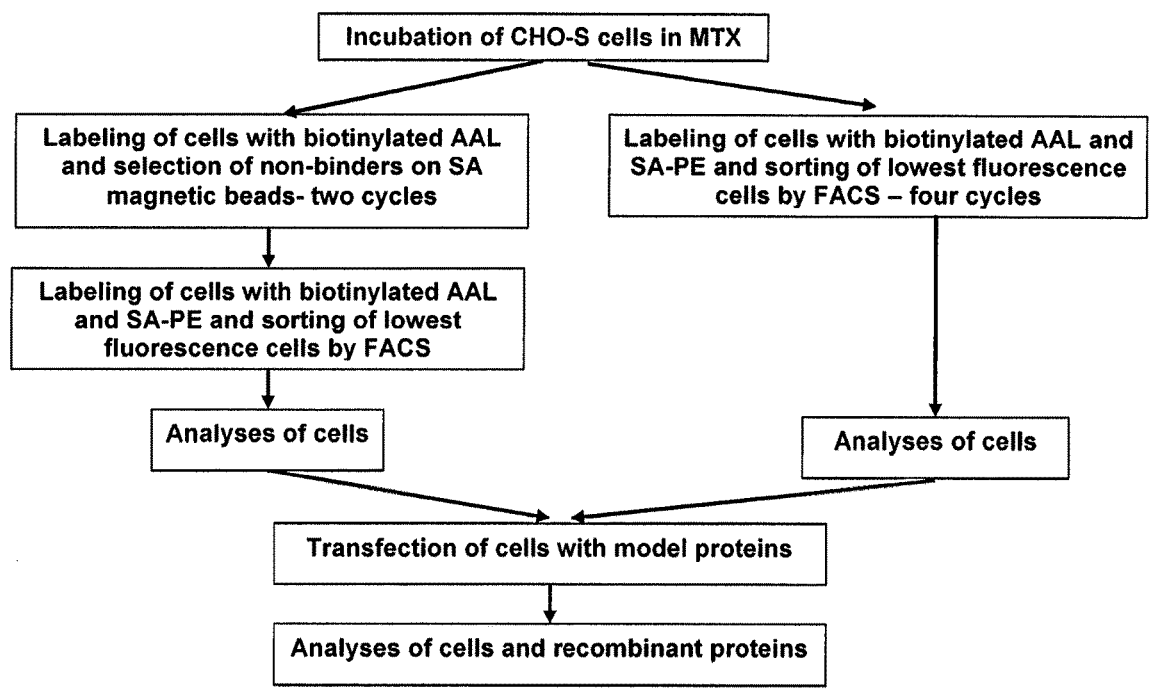
FIG. 1 is a flowchart of the experimental approach that was used to obtain cells with express polypeptides having zero or low fucose levels.
Figure 2:
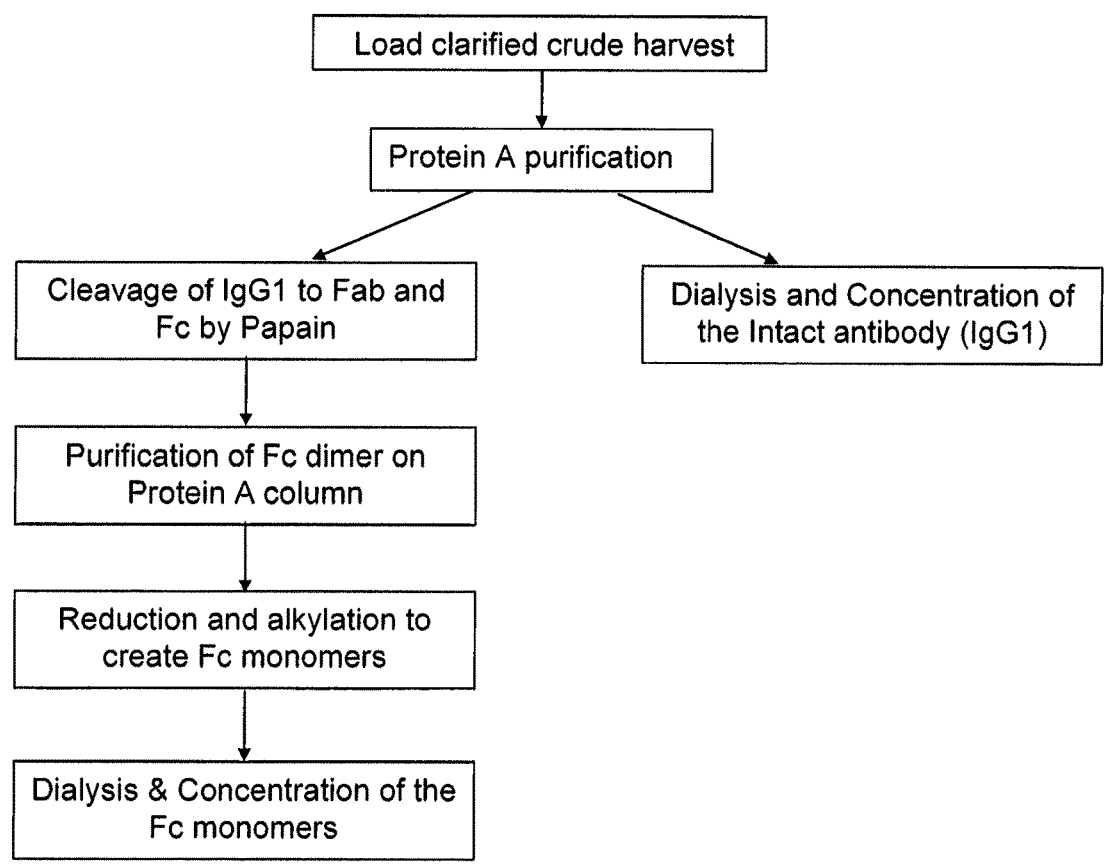
FIG. 2 is a flowchart of the anti-EGFR mAb intact and monomer purification processes.

Purification of Anti-EGFR Intact and FC Monomer:

The anti-EGFR products produced from pools (2390 and 2622UN) were purified on Protein A column. The purified products were analyzed either as intact IgG or Fc monomer (produced as described below). The purification process was done as outlined in FIG. 2 and was carried out using the AKTA Explorer systems.

Anti-EGFR Purification on Protein A:

The Protein A Sepharose-MAb Select Xtra pre-packed column (5 ml volume) was equilibrated with 5-6 CV of 50 mM Sodium Acetate pH 6.8, at a flow rate of 2.0 ml/min. The clarified crude harvest (~500 ml) containing product from pool was loaded onto the column at a flow rate of 2.0 ml/min. The column was washed in two steps (7-9 CV): first wash with 1.5 M NaCl in 50 mM Sodium Acetate pH 6.8 followed by the second wash with 50 mM Sodium Acetate pH 6.8, at a flow rate of 2.0 ml/min till baseline was obtained. The product was eluted in one fraction with 20 mM Acetic Acid pH 3.2 at a flow rate of 2.0 ml/min. The column run was performed at RT and monitored by UV at 280 and 215 nm. The pH was adjusted to 6.0 with Tris 1M. The column was washed with 0.1M Acetic acid, pH 2.9, and then cleaned in-place with 8 CV 4M Guanidin HCl. The column was re-equilibrated with 50 mM Sodium Acetate pH 6.8 and stored in 20% Ethanol.

Dialysis and Concentration Intact Anti-EGFR mAb:

The fraction eluted from the Protein A Sepharose—MAb Select Xtra column was dialysed in SnakeSkin dialysis tubing (10 kDa MW cut-off pore size) twice against "Formulation buffer" (100 mM NaCl, 100 mM glycine, 10 mM citrate, pH 5.8) over night in volume ratio about 1:100. After dialysis the sample was concentrated by ultrafiltration (10 kDa MW cut-off membrane) in an Amicon concentrator. Those steps were performed at 2-8° C. Product concentration of the concentrated product was measured by ELISA or by O.D. 280 nm.

Papain Cleavage of Antibody:

The fraction eluted from the Protein A column was dialysed in SnakeSkin dialysis tubing (10 kDa MW cut-off pore size) twice against buffer (0.1 M Tris-HCl, 4 mM EDTA, pH 7.6) over night at 4° C. in volume ratio about 1:100 (protein:buffer). After dialysis the sample was concentrated to 1 mg/ml by ultrafiltration (10 kDa MW cut-off membrane) in an Amicon concentrator. The anti-EGFR was cleaved to Fab and Fc fractions by Papain. The cleavage was carried out by incubating the antibody at a final concentration of 1 mg/ml in 0.1 M Tris-HCl pH 7.6, 4 mM EDTA, 5 mM cysteine. The digestion was initiated by the addition of papain (diluted to 1 mg/ml with water) to give a final protein:enzyme ratio of 100:1 (w/w). The digestion was carried out for 2 hours at 37° C., the cleavage was stopped by the addition of maleimide (33 mM) and chilled on ice. The Fc dimer fraction was purified from the cleavage mixture by Protein A affinity chromatography as described herein above. The purified Fc dimer dialysed in SnakeSkin dialysis tubing (10 kDa MW cut-off pore size) twice against PBS×1, pH 7.2 and concentrated to 2 mg/ml by ultrafiltration (10 kDa MW cut-off membrane) in an Amicon concentrator.

Reduction and Alkylation:

Reduction and alkylation was performed using the Fc dimer fraction under denaturing conditions to produce the Fc monomer for characterization of fucose level on the N glycosylation site at position 297 located in CH2 domain of the heavy chain (see background). Fc dimer fraction was diluted to 1 mg/ml with a buffer (4 M Guanidine-HCl, 50 mM Tris-HCl, pH 8.8), then Dithiothreitol (DTT, 5 mM) was added and the reaction mixture was placed at 75° C. for 5 minutes. Protein solution was then cooled to room temperature and 0.5 M Iodoacetamide stock solution was added to reach a final concentration of 15 mM. The alkylation was performed at room temperature for 40 minutes in the dark. Then a 0.5 M DTT stock solution was added to obtain 15 mM concentration to quench the alkylation.

Dialysis and Concentration Anti-EGFR Fc Monomer:

The fraction eluted from the Protein A Sepharose—MAb Select Xtra column was dialysed in SnakeSkin dialysis tubing (10 kDa MW cut-off pore size) twice against "Formulation buffer" (100 mM NaCl, 100 mM glycine, 10 mM citrate, pH 5.8) overnight in volume ratio about 1:100 (protein:buffer). After dialysis the sample was concentrated by ultrafiltration (10 kDa MW cut-off membrane) in an Amicon concentrator. Those steps were performed at 2-8° C. Product concentration of the concentrated product was measured by ELISA or by O.D. 280 nm.

Analysis of Fucose and Sialic Acid Level on Purified Protein by Octet:

This assay was used to determine either the level of fucose or sialic acid on purified products (intact IgG1 or Fc monomer) by the Octet kinetic analysis. The assay was performed as described below.

The NHS-PEG4-Biotin reagent was used for biotinylation of either AAL or MAA according manufacturer instructions. The biotin reagent solution (1 mM in PBS×1, pH 7.2) was added to 1 ml of lectin (1 mg/ml) (1:5 ratio Lectin: Biotin). The reaction mixture was incubated for 2 hours on ice. Dialyis of the sample was performed against PBS pH 7.2 in Slide-A-Lyzer cassette (10 kDa MW cut-off pore size).

Figure 3:
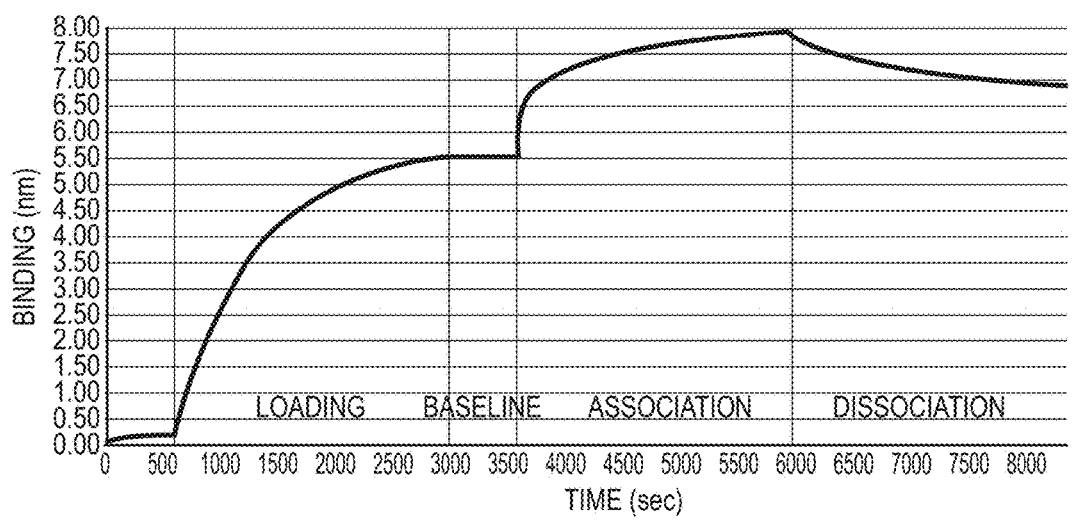
FIG. 3 is an exemplary profile of a kinetic analysis by Octet.

The streptavidin biosensors (SA) were pre-incubated in kinetic buffer for 20 min at 30° C. without shaking before the experiment was started. The buffers, the biotinylated lectin and the purified product were prepared according to the required concentration and were transferred to a 96-well plate (250 µl/well), all steps were performed at 30° C., shaking rate (1000 rpm). The run was initiated by placing the biosensors in the appropriate wells and measuring the change in layer thickness (in nanometers, nm) with time, all under computer control. First the 1 µg/ml of biotinylated AAL (AAL-B) or 10 µg/ml biotinylated MAA (MAA-B) was immobilized onto the streptavidin biosensor tips surface for 40 min (the loading step). Then the tips were washed in diluted kinetics buffer (KB×1) for 10 min (baseline step). At the association step the purified protein was bound to the biotinylated lectin for 40 min followed by washing in the KB×1 buffer for the dissociation step. FIG. 3 shows a typical profile of a kinetic analysis by the Octet. Data was processed automatically using the Octet User Software version 6.3.

Charge Profile Analysis of Purified Antibody by ICE 280:

Imaged capillary isoelectric focusing was performed using an iCE280 Analyzer (Convergent Biosciences). The isoforms separation is achieved on a capillary cartridges (50 mm length, 100 µm I.D. column), separation capillary that has its inner surface pre-coated with fluorocarbon compound.

The purified and dialyzed anti-EGFR samples were concentrated to 4 mg/ml by ultrafiltration (10 kDa MW cut-off cellulose membrane) in an Amicon Ultra Centrifugal Filter. The sample for analysis was prepared by mixing 20 µl of 4 mg/ml anti-EGFR, 80 µl of running stock solution. The separation is performed using a 100 mM NaOH as catholyte and a 80 mM H3PO4 as anolyte solutions. The electropherograms are acquired by UV absorbance at 280 nm. A summary of the final conditions and concentration are given in Table 3 herein below.

TABLE 3

| | |
|---|---|
| Final Sample concentration | A round 0.4 mg/ml (80 µg of protein in the final volume of 200 µl of final ampholyte sample solution is sufficient to run more than three replicates). |
| Capillary | 50 mm length, 100 µm ID column, fluorocarbon coating |
| Electrolytes | Analyte-80 mM $H_3PO_4$; Catholyte-100 mM NaOH in 0.1% methyl-cellulose. |
| Carrier Ampholytes | Pharmalyte 3-10 (4% final concentration)) |
| Additive | 0.35% Methyl cellulose |
| Internal pI Markers | 6.14 and 9.5 (0.5% final concentration) |
| Focusing Time | 1 + 8 minutes |
| Focusing Voltage | 1 minute at 1500 V (300 V/cm) 8 minute at 3000 V (600 V/cm) |

Analysis of the Glycosylation Profile on Fc Monomer by MS:

Fc monomer of antibody to EGFR was isolated as described above further evaluated for glycan analysis by MS.

Cell Propagation and Productivity in ACFM

Cell Culture Maintenance and PDT Calculations

Cell cultures were maintained in ACFM as follows: Cells were seeded into 50 ml tubes at a concentration of 0.2×10⁶ cell/ml and incubated at 37° C. on an orbital shaker at 320 rpm. Twice a week, cell number and viability were measured. The culture was passaged by centrifugation at 100 g for 5 minutes at 4° C. and cell pellet was then re-suspended in fresh pre-warmed ACFM.

Population doubling level (PDL) and population doubling time (PDT) calculations were determined according to the following equations:

$$PDL = \frac{\log(Te) - \log(Ti)}{\log(2)}$$

$$PDT = \frac{24 * (\text{days})}{PDL}$$

Ti—total live cells at seeding
Te—total live cells in the end

Determination of Maximum Cell Concentration:

Cells were seeded into 50 ml tubes (TPP, Cat#87050) at a concentration of 0.2×10⁶ cell/ml and incubated at 37° C. on an orbital shaker at 320 rpm. At different time points cell number and viability were measured.

Specific Productivity in ACFM:

For specific productivity (PCD) in ACFM, cells were seeded in the specified ACFM at a concentration of 0.5×10⁶ cells/ml, in a 50 ml tube and incubated at 37° C. in a shaker incubator (320 rpm) for 24 hours. Medium was then taken out and product concentration was determined by ELISA. The calculation was done by dividing the 24 hours titers by the average concentration of cells at seeding and after 24 hours of the experiment.

$$PCD = \frac{T}{\frac{Ci + Ce}{2}}$$

PCD—pg/cell/day
T—titer (pg/ml)
Ci—cell concentration at seeding (cells/ml)
Ce—cell concentration after 24 hrs (cells/ml)

Growth and Productivity in a Batch Process:

Growth and productivity in cell suspension batch process was done at seeding concentration of $0.2\times10^6$ cells/well in 40 ml ProCHO5 medium and 12 ml CHO CD Efficient-Feed™ A, (Invitrogen, Cat. # A10234-01)+CHO CD EfficientFeed™ B Invitrogen, Cat. # A10240-01) (1:1) in 125 ml Erlenmeyer flasks: 125 ml (Corning, Cat. # WI-431143) shaking at 125 RPM, at 37° C. with 5% $CO_2$ until viability level declined below 70%. Samples were withdrawn for product titer analysis (by ELISA), metabolites concentration, cell concentration & viability every 1-2 days from day three onward.

Example 1

Strategy for Isolation of Low Fucose Containing Cells

The strategy employed for isolation of low fucose expressing cells was based on creation of random mutations and selection of cells with the required low fucose phenotype.

Figure 4:
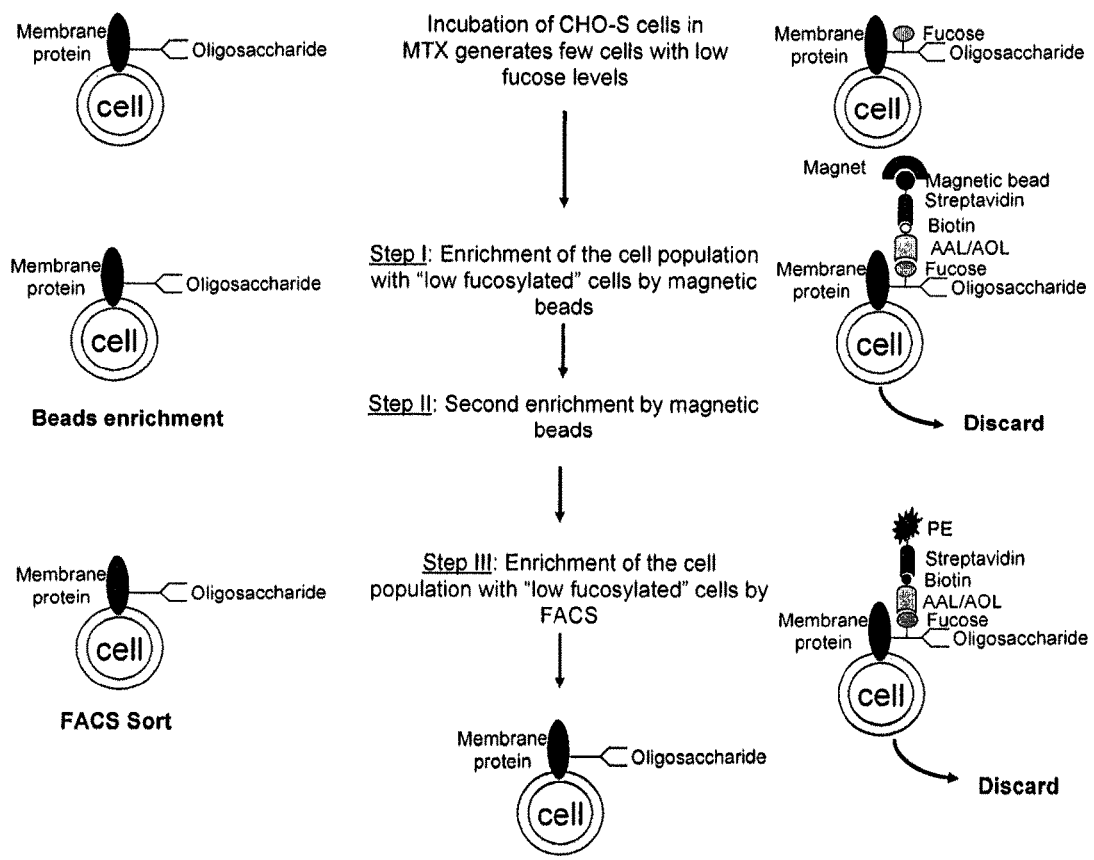
FIG. 4 is a diagram illustrating an exemplary strategy for isolation of ITL-LF1 low fucose cells (zero fucose, in the absence of external fucose). CHO-S cells were incubated with the mutagenic agent methotrexate (MTX) following by two rounds of selection of low fucose cells by labeling the cells with biotinlyated fucose specific lectin (biotinylated AAL) and isolation of cells that do not bind to streptavidin coated magnetic beads. This step was followed by another round of selection in which the cells were labeled with biotinlyated fucose specific lectin (biotinylated AAL) and fluorescent streptavidin and selection of the low fluorescent cells was performed by FACS.
Figure 5:
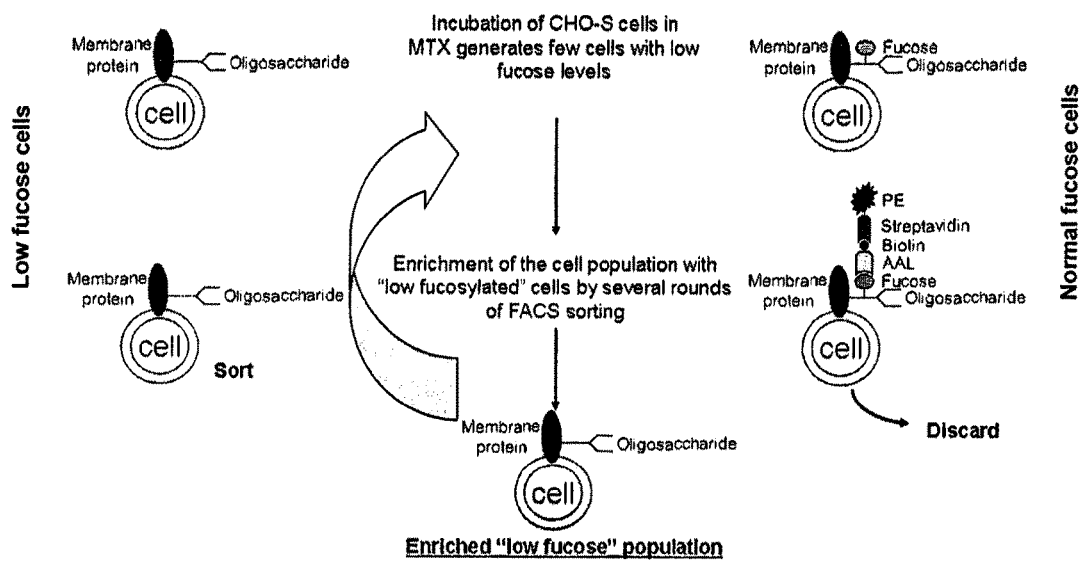
FIG. 5 is a diagram illustrating an exemplary strategy for isolation of ITL-LF1 low fucose cells. CHO-S cells were incubated with the mutagenic agent MTX followed by four rounds of cell labeling with biotinlyated fucose specific lectin (biotinylated AAL) and fluorescent streptavidin and sorting of the low fluorescent cells by FACS.

The process comprised several steps (as depicted in FIGS. 4 and 5) and was initiated by by incubation of CHO-S cells with the mutagenic agent MTX so as to generate mutations. Then MTX was removed and the cells were isolated according to one of the following steps:
1. Two rounds of cell labeling with biotinlyated fucose specific lectin (biotinylated AAL or AOL) and isolation of cells that do not bind to streptavidin coated magnetic beads. This step was followed by cell labeling with biotinlyated fucose specific lectin (biotinylated AAL or AOL) and fluorescent streptavidin and a single sort of the low fluorescent cells by FACS (FIG. 4).
2. Four rounds of cell labeling with biotinlyated fucose specific lectin (biotinylated AAL) and fluorescent streptavidin and sorting of the low fluorescent cells by FACS (FIG. 5).

Incubation of CHO-S Cells in MTX:

CHO-S cells in C6614 were seeded at $0.2\times10^6$ cells/ml in 100 nM MTX and propagated for 10 days until viability exceeded 90%. Then the cells were transferred at the same initial concentration to C6614 with 200 nM MTX until viability exceeded 90%. The cells were frozen and served for isolation of low fucose containing cells.

Example 2

Selection of Low Fucose Cells by Two Rounds of Isolation with Streptavidin Magnetic Beads and One FACS Sorting Cycle (ITL-LF1 Cells)

Fifty million CHO-S cells incubated in 200 nM MTX, wild type CHO-S and CHO DUKX cells were separated once on magnetic beads seeded in 96 well plates propagated and transferred in T80 flasks. The number and the viability of the separated unbound cells was higher in the case of the MTX treated CHO-S cells and much lower in non MTX treated cells. Moreover, CHO-S cells incubated in MTX reached T80 flasks in 14 days, whereas CHO-S and CHO-DUKX reached T80 flasks only after 22 days. Further low fucose cell isolation was done only with MTX treated CHO-S cells. The second streptavidin coated magnetic beads isolation was initiated with $5\times10^7$ cells and the selected non-binding cells were seeded in 96 well plates. FACS sorting of the 1.5% lowest fucose population was performed with $4\times10^7$ cells following recovery and cell propagation.

Figure 6:
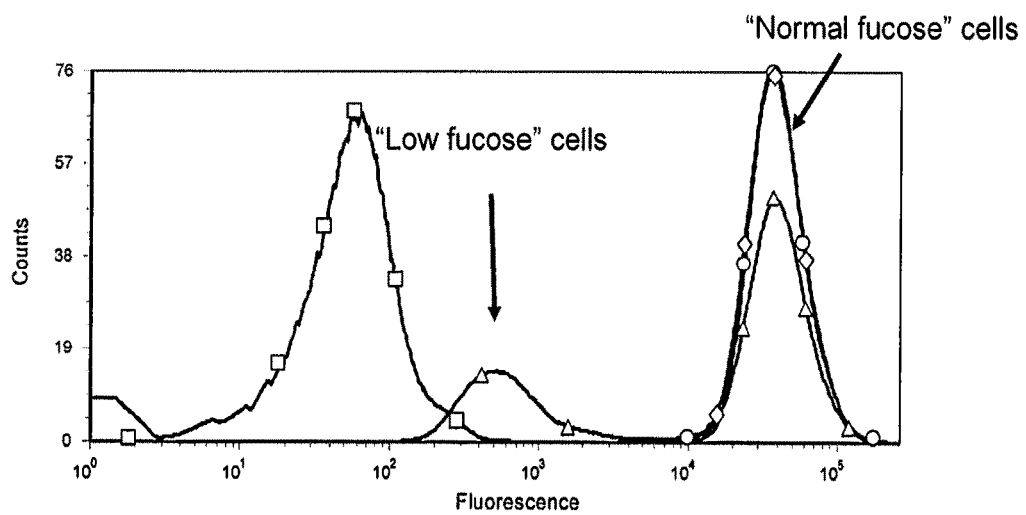
FIG. 6 is a graph illustrating FACS analysis of fucose levels on MTX treated and untreated CHO-S cells after separation on magnetic beads. CHO-S cells incubated or not with MTX were labeled with biotinylated AAL and mixed with streptavidin coated magnetic beads. The cells were separated with a magnet and cells, which did not attached to the magnet, were further propagated. FACS analysis was carried out by labeling the cells with biotinylated AAL followed by staining with fluorescent streptavidin. CHO-S MTX treated cells, not labeled (□), CHO-S incubated with MTX and labeled with AAL (○), low fucose CHO-S cells incubated in MTX and sorted with beads (Δ), CHO-S sorted with beads (◇).
Figure 7A:
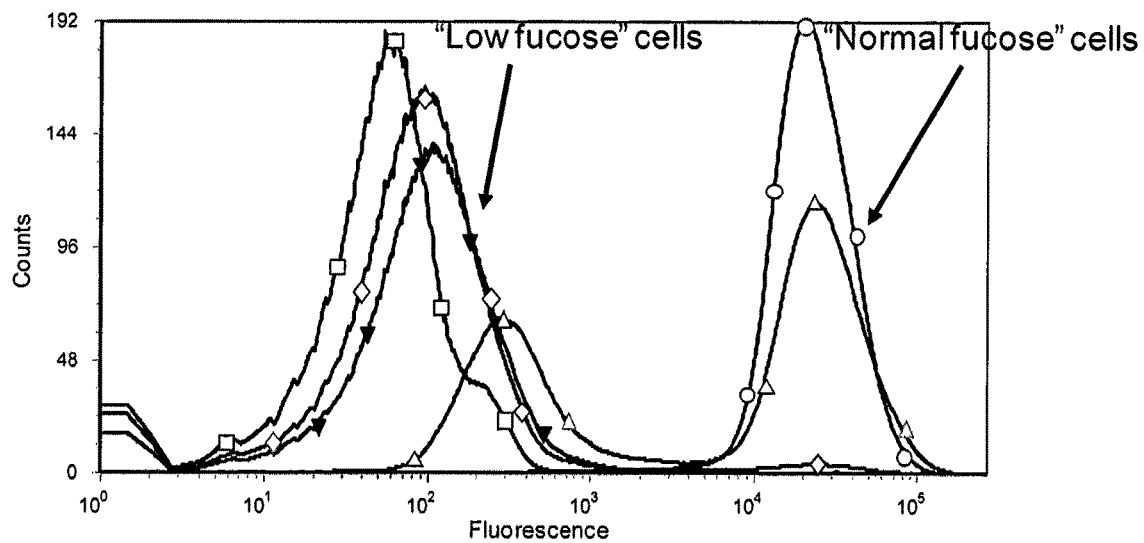
FIG. 7A is a graph illustrating FACS analysis of fucose levels on ITL-LF1 cells isolated by magnetic beads and FACS. CHO-S cells incubated with MTX were labeled with biotinylated AAL and mixed with streptavidin coated magnetic beads. The cells were separated on a magnet and cells, which did not attached to the magnet, were further propagated. This step was repeated two times. Then the cells were labeled with biotinylated AAL and fluorescent streptavidin and the low fluorescent cells were sorted by FACS and were further propagated. FACS analysis was carried out by labeling the cells with biotinylated AAL and fluorescent streptavidin. CHO-S cells MTX treated, not labeled (□), CHO-S cells MTX treated (○), CHO-S cells MTX treated following a single separation on beads (Δ), CHO-S cells MTX treated following two separation cycles on beads (◇), CHO-S cells MTX treated following two separation cycles on beads and a single FACS sorting cycle (▼).
Figure 8A:
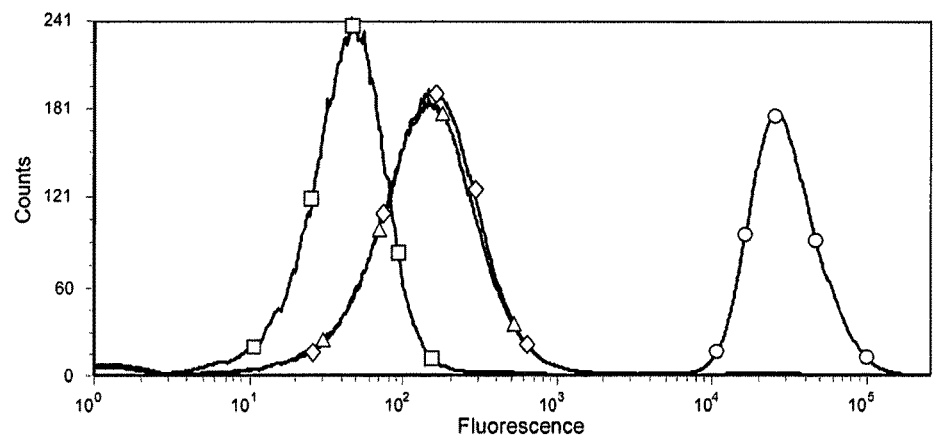
FIG. 8A is a graph illustrating FACS analysis of fucose levels on ITL-LF1 in various media. ITL-LF1 cells propagated in ProCHO5 and C6614 and analyzed by FACS following labeling of the cells with biotinylated AAL and fluorescent streptavidin. CHO-S MTX treated, not labeled (□), CHO-S in ProCHO5 (○), ITL-LF1 in ProCHO5 (Δ), ITL-LF1 in C6614 (◇).

Analysis of Fucose Level on Cells' Membrane:

Analysis of the fucose level on the cells surface showed that following labeling of cells with biotinylated AAL and SA-PE, only the CHO-S MTX sorted cells showed a sub population with low fucose levels on the cells' membrane. CHO-S (FIG. 6) and CHO DUKX (data not shown) separated cells presented normal fucose level on the cells' membrane. A further analysis of CHO-S MTX treated cells following two rounds of streptavidin coated magnetic beads selection and a single FACS sorting selection is depicted in FIG. 7A and shows the low fucose profile of the sorted cells. The low fucose profile was found to be similar in both ProCHO5 and C6614 media (FIG. 8A).

Figure 8B:
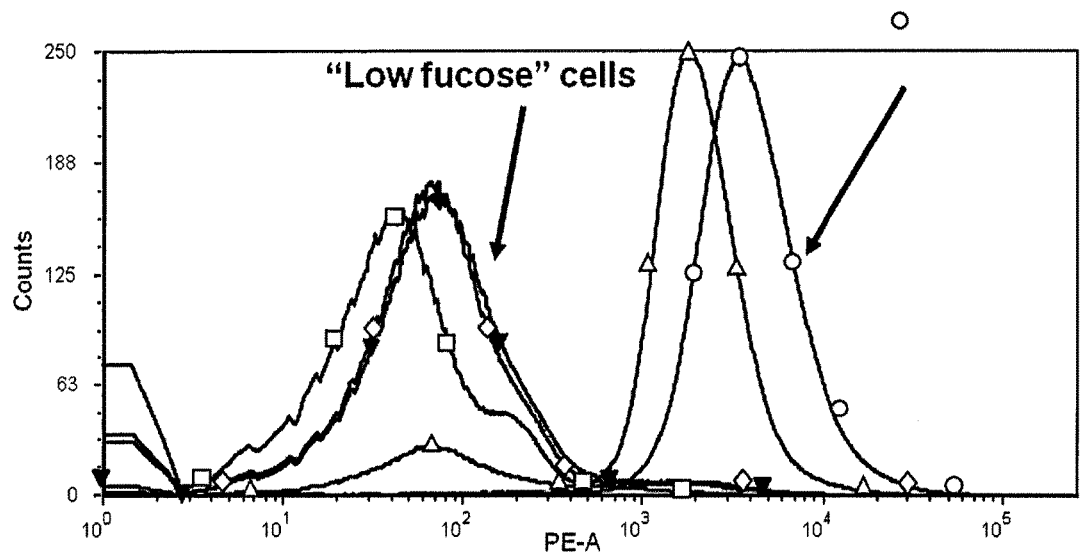
FIG. 8B is a graph illustrating FACS analysis of fucose levels on MTX treated CHO-S cells isolated by magnetic beads and FACS. CHO-S cells incubated with MTX were labeled with biotinylated AOL and mixed with streptavidin coated magnetic beads. The cells were separated on a magnet and cells, which did not attached to the magnet, were further propagated. This step was repeated two times. Then the cells were labeled with biotinylated AOL and fluorescent streptavidin and the low fluorescent cells were sorted by FACS and were further propagated. FACS analysis was carried out by labeling the cells with biotinylated AOL and fluorescent streptavidin. CHO-S cells, not labeled (□), CHO-S cells (○), CHO-S cells MTX treated following a single separation on beads (Δ), CHO-S cells MTX treated following two separation cycles on beads (◇), CHO-S cells MTX treated following two separation cycles on beads and a single FACS sorting cycle (▼).

A similar approach was performed with biotinylated AOL. Analysis of CHO-S MTX treated cells labeled with biotinylated AOL following two rounds of streptavidin coated magnetic beads selection and a single FACS sorting selection is depicted in FIG. 8B and shows the low fucose profile of the sorted cells.

Figure 7B:
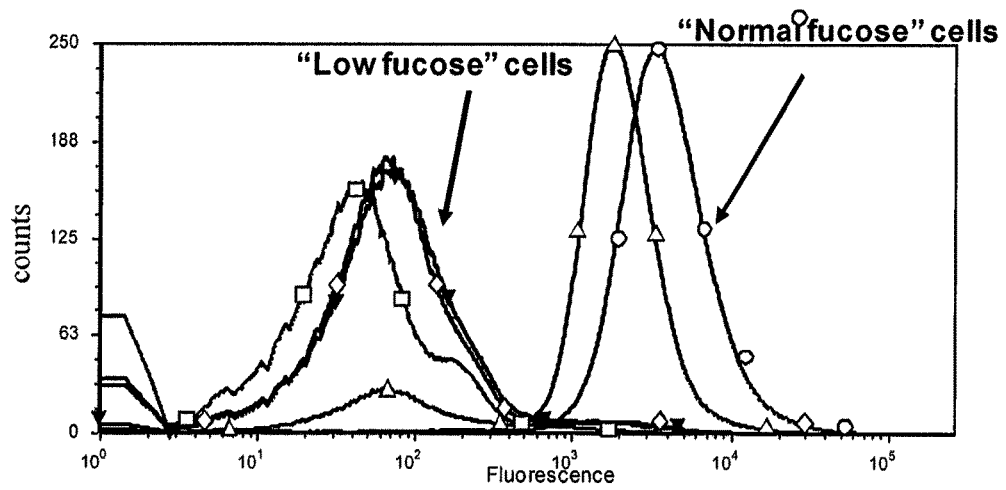
FIG. 7B is a graph illustrating FACS analysis on fucose levels on cells selected using *Aspergillus oryzae* 1-fucose-specific lectin (AOL). CHO-S cells, not labeled (□), CHO-S cells (○), CHO-S cells MTX treated following a single separation on beads (Δ), CHO-S cells MTX treated following two separation cycles on beads (◇), CHO-S cells MTX treated following two separation cycles on beads and a single FACS sorting cycle (▼).

Use of *Aspergillus oryzae* l-Fucose-Specific Lectin (AOL) to Select for Low Fucose Cells:

CHO-S cells incubated with MTX were labeled with biotinylated AOL and mixed with streptavidin coated magnetic beads. The cells were separated on a magnet and cells, which did not attach to the magnet, were further propagated. This step was repeated twice. Then the cells were labeled with biotinylated AOL and fluorescent streptavidin and the low fluorescent cells were sorted by FACS and were further propagated. FACS analysis was carried out by labeling the cells with biotinylated AOL and fluorescent streptavidin. The results shown in FIG. 7B show that AOL may also be used to select for low fucose expressing cells.

Figure 9:
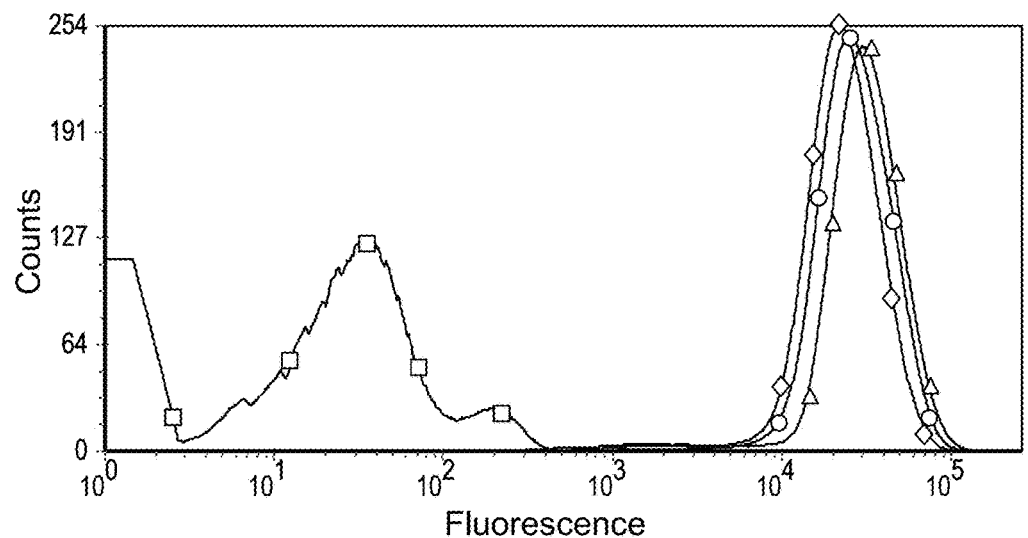
FIG. 9 is a graph illustrating FACS analysis of the sialic acid levels on ITL-LF1 cells in various media. ITL-LF1 cells were analyzed for sialic acid levels in ProCHO5 and C6614 media. The cells were labeled with FITC conjugated sialic acid binding lectin specific lectin (MAA) and analyzed by FACS. CHO-S cells, not labeled (□), CHO-S cells labeled with MAA-FITC (○), ITL-LF1 cells in ProCHO5 labeled with MAA-FITC (Δ), ITL-LF1 cells in C6614 labeled with MAA-FITC (◇).

Analysis of Sialic Acid Level on Cells' Membrane:

Analysis of the sialic acid level may indicate not only the existence of sialic acid on the oligosaccharides, but also ensures that during the low fucose cell selection, the entire oligosaccharide has not been lost. Analysis of the sialic acid level on the cell's membrane was done by incubation of the cells with sialic acid specific lectin (MAA) conjugated to FITC followed by FACS analysis. The analysis showed that following labeling of cells with biotinylated AAL and SA-PE, both CHO-S and ITL-LF 1 cells present similar levels of sialic acid on the cells' membrane in ProCHO5 and C6614 media (FIG. 9).

Figure 10:
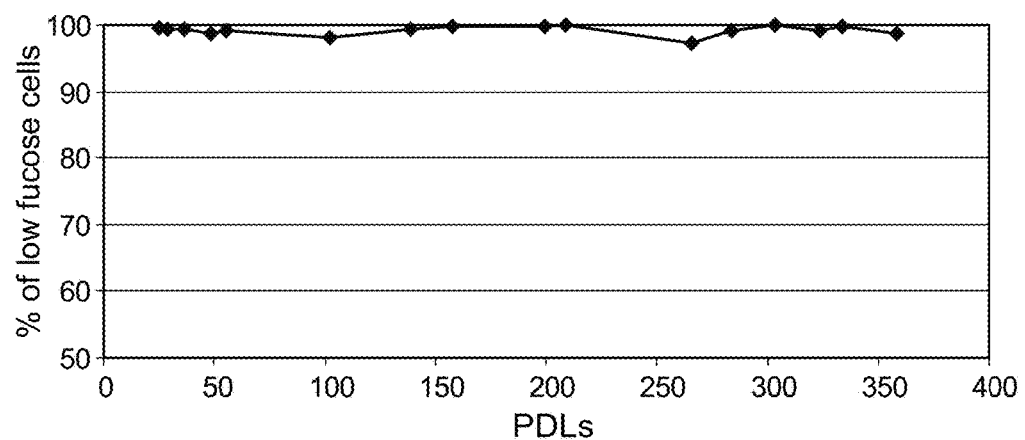
FIG. 10 is a graph illustrating evaluation of the fucose stability of ITL-LF1 cells. ITL-LF1 cells were analyzed by FACS for fucose level on cell surface at different times points after completion of the separation process, in order to evaluate the stability of low fucose expression. For analysis, the cells were labeled with biotinylated AAL and fluorescent streptavidin.

Stability of Low Fucose Phenotype:

Analysis of the fucose level on the cells surface was determined at different time points after selection of the ITL-LF1 cells for 358 population doublings (PDLs) and showed that following labeling of cells with biotinylated AAL and SA-PE, the low fucose phenotype remained low and stable (FIG. 10).

Growth Rate:

The growth rate of the ITL-LF1 cells was determined during the fucose stability test and was found to result in a PDT of 15-20 hours (FIG. 11) similar to CHO-S.

Example 3

Selection of Zero Fucose Cells by Sorting with FACS (ITL-LF2 Cells)

CHO-S cells incubated in 200 nM MTX were sorted by FACS to select for a low fucose population. The initial cell number taken for sorting, the fraction of low fucose gated cells as well as the number of sorted cells in every sorting cycle is indicated in Table 4 herein below.

TABLE 4

| FACS sorting cycle | Initial cell number | % of cells gated | Sorted cell number |
|---|---|---|---|
| 1 | $6.5 \times 10^7$ | 0.2 | $1.2 \times 10^{4*}$ |
| 2 | $6.5 \times 10^7$ | 0.07 | $5.8 \times 10^{3*}$ |
| 3 | $8 \times 10^7$ | 1.0 | $8 \times 10^{5\#}$ |
| 4 | $6 \times 10^7$ | 2.0 | $1 \times 10^{6\#}$ |

*Cells counted by Cellavista after sort
Estimated number of cells according to the FACS gate.

Figure 12:
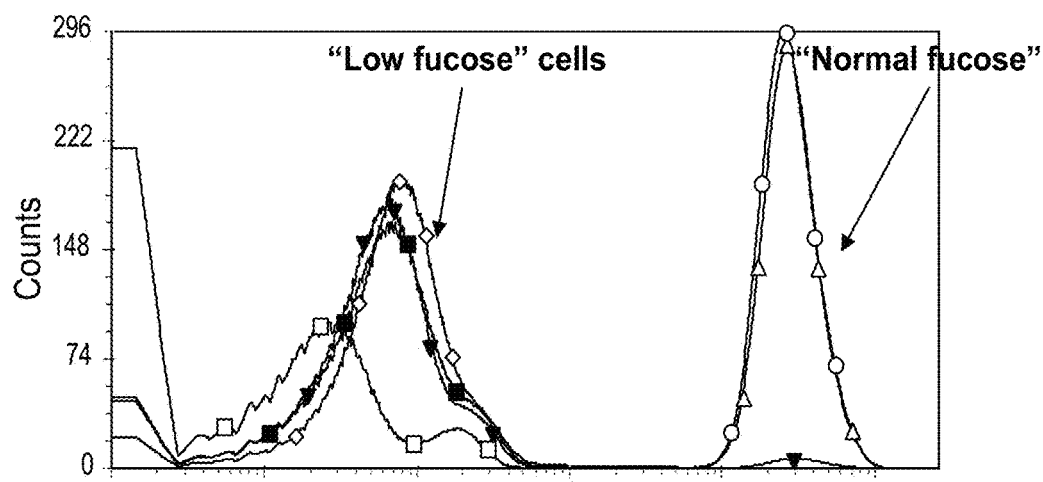
FIG. 12 is a graph illustrating FACS analysis of ITL-LF2 cells isolated by consecutive FACS sorting. CHO-S cells incubated with MTX were labeled with biotinylated AAL and fluorescent streptavidin. The low fluorescent cells were sorted by FACS and were further propagated. This procedure was repeated four times. FACS analysis was carried out by labeling the cells with biotinylated AAL and fluorescent streptavidin. CHO-S MTX treated cells, not labeled (□), CHO-S MTX treated cells (○), CHO-S MTX treated cells after the first sort (Δ), CHO-S MTX treated cells after the second sort (◇), CHO-S MTX treated cells after the third sort (▼) CHO-S MTX treated cells after the fourth sort (■).
Figure 13:
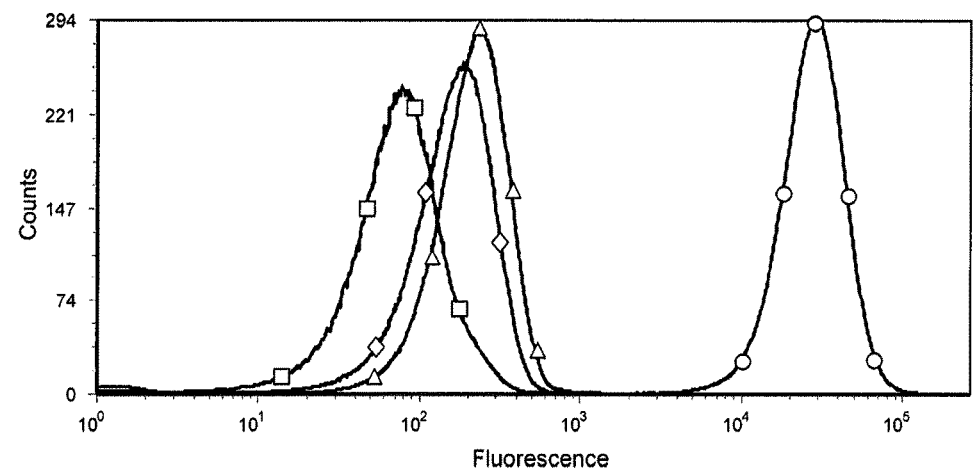
FIG. 13 is a graph illustrating FACS analysis of fucose levels on ITL-LF2 cells in various media. ITL-LF2 cells propagated in ProCHO5 and C6614 and analyzed by FACS following labeling of the cells with biotinylated AAL and fluorescent streptavidin. CHO-S, not labeled (□), CHO-S in ProCHO5 (○), ITL-LF2 in ProCHO5 (Δ), ITL-LF2 in C6614 (◇).

Analysis of Fucose Level on Cells' Membrane:

Analysis of the fucose level on the cells' surface showed that following labeling of cells with biotinylated AAL and SA-PE, the zero fucose sorted CHO-S MTX fraction increased with the number of sorts performed. Three rounds of sorts resulted in a homogenous population with low fucosylation levels. A fourth sort was applied in order to further substantiate the selection of homogenous population with low fucose levels (FIG. 12). Another analysis showed that the fucosylation levels of ITL-LF2 cells were zero in both ProCHO5 and C6614 media (FIG. 13).

Figure 14:
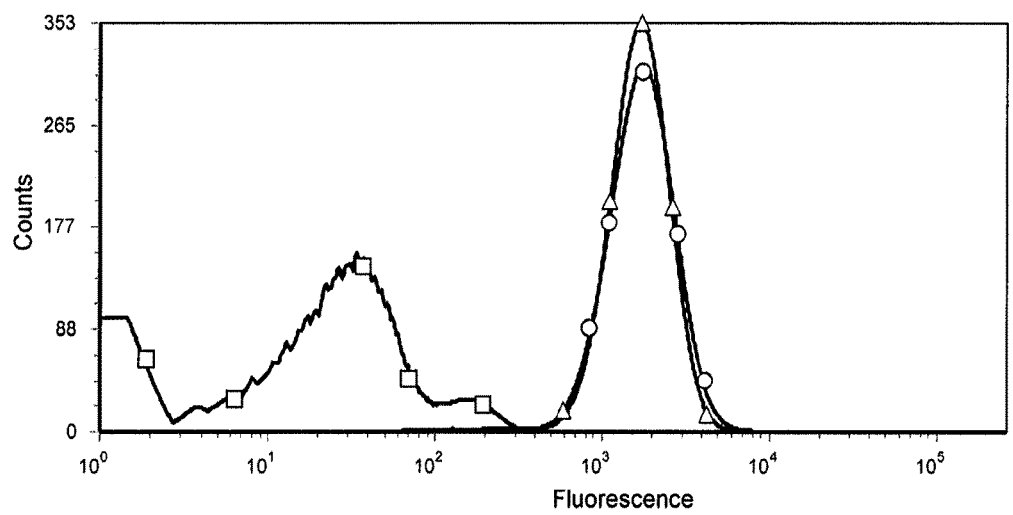
FIG. 14 is a graph illustrating FACS analysis of the sialic acid levels on ITL-LF2 cells. ITL-LF cells were analyzed for sialic acid levels in ProCHO5 medium. The cells were labeled with FITC conjugated sialic acid binding lectin (MAA) and analyzed by FACS. CHO-S cells, not labeled (□), CHO-S cells labeled with MAA-FITC (○), ITL-LF2 cells in ProCHO5 labeled with MAA-FITC (Δ).

Analysis of Sialic Acid Level on Cells' Membrane:

Analysis of the sialic acid level may indicate not only the existence of sialic acid on the oligosaccharides but also ensures that along the low fucose selection the entire oligosaccharide has not been lost. The analysis showed that following labeling of cells with sialic acid specific lectin FITC conjugated MAA, both CHO-S and ITL-LF2 cells present similar levels of sialic acid on the cells' membrane (FIG. 14).

Stability of Low Fucose Phenotype:

Analysis of the fucose level on the cells surface was determined at different time points after selection of the ITL-LF2 low fucose cells for 370 PDLs and showed that following labeling of cells with biotinylated AAL and SA-PE, the low fucose phenotype remained low and stable (FIG. 15).

Figure 16:
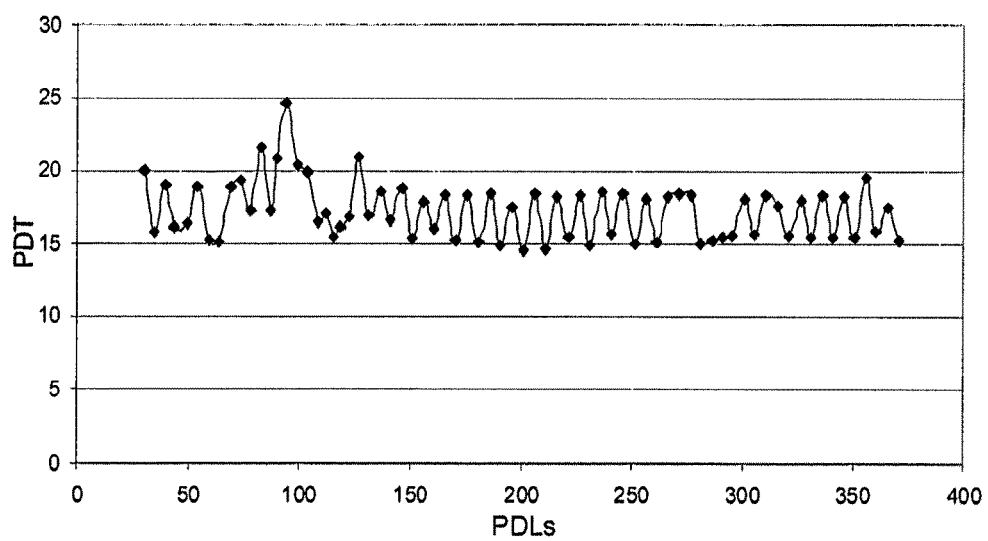
FIG. 16 is a graph illustrating the growth rate of ITL-LF2 cells. ITL-LF2 cells were propagated along 370 PDLs and the growth rate was determined after every passage.

Growth Rate:

The growth rate of the ITL-LF2 cells was determined during the fucose stability test and was found to result in a PDT of 15-20 hours (FIG. 16) similar to CHO-S.

Figure 17:
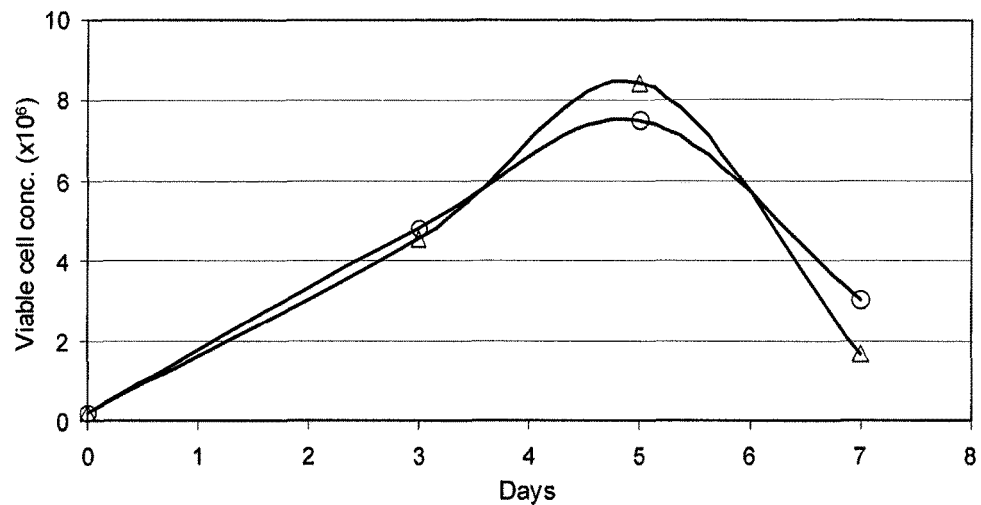
FIG. 17 is a graph illustrating evaluation of maximum cell concentration of ILA-LF2 cells in ProCHO5. Cells were seeded at $0.2 \times 10^6$ in a batch process and the number of cells was determined every couple of days. CHO-S cells (○) and ITL-LF2 cells (Δ).

Maximum Cell Concentration:

To determine maximum cell concentration under pure batch culture conditions (no feed), ITL-LF2 cells were seeded at a concentration of $0.2 \times 10^6$ cells/ml in a 50 ml tube and cultured for seven days. Maximum viable concentration reached was $8.4 \times 10^6$ cells/ml which is slightly higher than parent CHO-S that reached a maximum of $7.5 \times 10^6$ viable cells/ml (FIG. 17).

Figure 18:
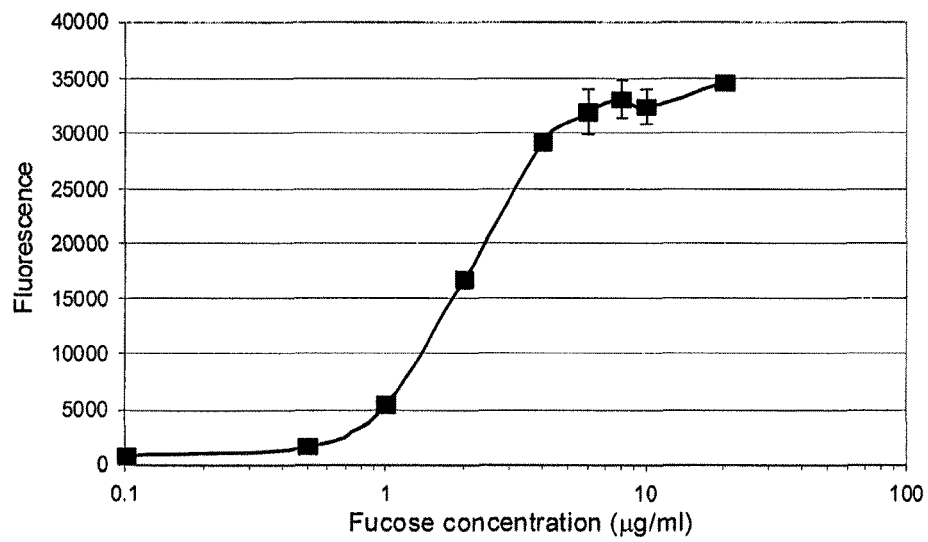
FIG. 18 is a graph illustrating the effect of exogenous fucose on fucosylation level of ITL-LF2 cells. ITL-LF2 cells were seeded in ProCHO5 medium at a concentration of $0.2 \times 10^6$ cells/ml with different concentrations of L-fucose and incubated at 37° C. incubator on shaker at 320 rpm with $CO_2$.

Effect of Exogenous Fucose on Fucosylation Level of ITL-LF2 Cells:

ITL-LF2 cells were seeded in ProCHO5 medium in the presence of increasing concentrations of L-fucose in the culture medium. FACS analysis results show correlation between the exogenously added fucose concentration and the fucosylation level on the cells' membrane (FIG. 18).

Figure 19A:
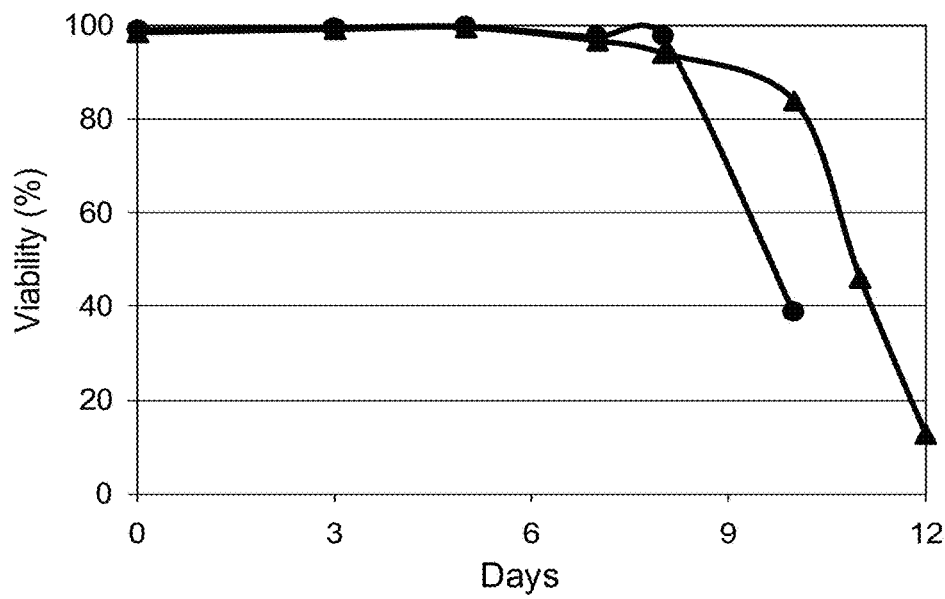
FIG. 19A is a graph illustrating viability of ITL-LF2 and CHO-S in a batch process. Cells were seeded at a concentration of $0.2 \times 10^6$ cells/ml in ProCHO5 with supplements in a batch process and the viability of the cells was analysed along the process. CHO-S cells (○) and ITL-LF2 cells (Δ).
Figure 19B:
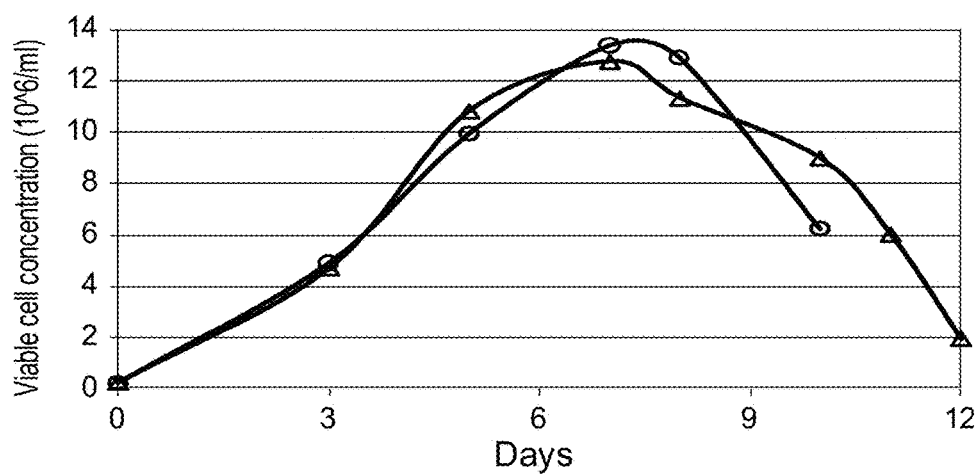
FIG. 19B is a graph illustrating viable cell concentration of ITL-LF2 and CHO-S in a batch process. Cells were seeded at a concentration of $0.2 \times 10^6$ cells/ml in ProCHO5 with supplements in a batch process and the number of cells was analyzed along the process. CHO-S cells (○) and ITL-LF2 cells (Δ).
Figure 19C:
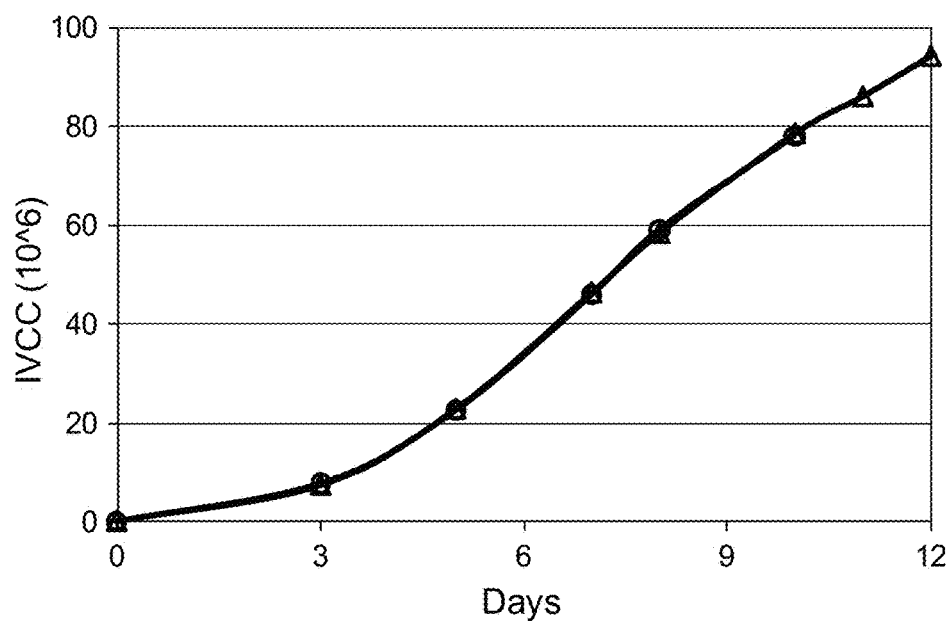
FIG. 19C is graph illustrating integral viable cell concentration (IVCC) of ITL-LF2 and CHO-S in a batch process. Cells were seeded at a concentration of $0.2 \times 10^6$ cells/ml in ProCHO5 with supplements in a batch process. The viable cell concentration was measured along the process. IVCC was calculated based on cell concrtation measurement. CHO-S cells (○) and ITL-LF2 cells (Δ). Note that both CHO-S and ITL-LF2 lines are congruent, but CHO-S cells reach only day 9 whereas ITL-LF2 cells reach day 12.

Growth of ITL-LF2 Cells in a Batch Process:

In order to evaluate the performances of the ITL-LF2 cells and compare them to CHO-S cells in a batch process the cells were seeded in ProCHO5+CHO CD EfficientFeed™ and propagated for as long as the viability remained higher than 60%. Samples were taken from the culture in order to measure cell concentration, cell viability, metabolites concentration and product titers. The results show that ITL-LF2 grow for a longer time with higher viability (FIGS. 19B and 19C) and ~20% higher integral viable cell concentration (IVCC) (FIG. 19D) in comparison to CHO-S cells. ITL-LF2 cells also show significantly lower lactate concentration along the process (FIG. 19D), which indicates that those cells utilize of lactate as a carbon source more efficiently than the parent CHO-S cells.

Cloning by FACS ACDU:

Cloning of ITL-LF2 cells was done by the Automated Cell Deposition Unit (ACDU) device of the FACSAria cell sorter. 103 and 124 clones emerged from 192 wells seeded in 80% C6366+20% ProCHO5 in two experiments (which reflects 54 and 65% recovery) eight days post cloning. Similar recovery range is usually obtained following cloning of CHO-S cells (data not shown). Several clones were propagated in ProCHO5 medium and served for mRNA characterization.

Genetic Analysis of ITL-LF2 Cells:

The fucosylation pathway is composed of two routes that start separately and converge. The two routes are composed of the de novo pathway from D-glucose and the salvage pathway from L-fucose. To investigate the cause of the low fucose phenotype in ITL-LF2 cells, analysis was carried out on expression of genes that are involved in the pathway. This is in order to see if any of these genes may be disrupted either in sequence or in expression levels. The genes that were analyzed for expression pattern (by RT-PCR and sequencing) and expression level (by Q-PCR) are highlighted in FIG. 20.

The sequence of the primers are detailed in Table 5 herein below.

TABLE 5

| Gene | 5' primer # | Sequence | 3' primer # | Sequence |
|---|---|---|---|---|
| Alpha 1,6 Fucosyltransferase (Fut8) | 580-23 | ATAATGCGGG CATGGACTGGTTC SEQ ID NO: 33 | 581-26 | ATACTATTTT TCAGCTTCAGGATATG SEQ ID NO: 34 |
| GDP-4-keto-6-deoxy-D-mannose epimerase-reductase (Fx) | 582-23 | ATAATGGGT GAGCCCCAGGGATC SEQ ID NO: 35 | 583-23 | ATATCTAGACAA GGGACAGCAGG SEQ ID NO: 36 |
| GDP-mannose 4,6-dehydratase | 586-26 | ATAATGGCTC ACGCTCCCGCTAGCTG | 587-22 | ATATCAGGCGTT GGGGTTGGTT |

TABLE 5-continued

| Gene | 5' primer # | Sequence | 3' primer # | Sequence |
|---|---|---|---|---|
| (GMD) - 5-6 exon primers | | SEQ ID NO: 37 | | SEQ ID NO: 38 |
| GDP beta L fucose pyrophosphorylase (GFPP) | 584-23 | ATAATGGCGTC TCTGCGCGAAGC SEQ ID NO: 39 | 585-23 | ATATTAAGATT TCTCCGAATCAG SEQ ID NO: 40 |

Figure 21:
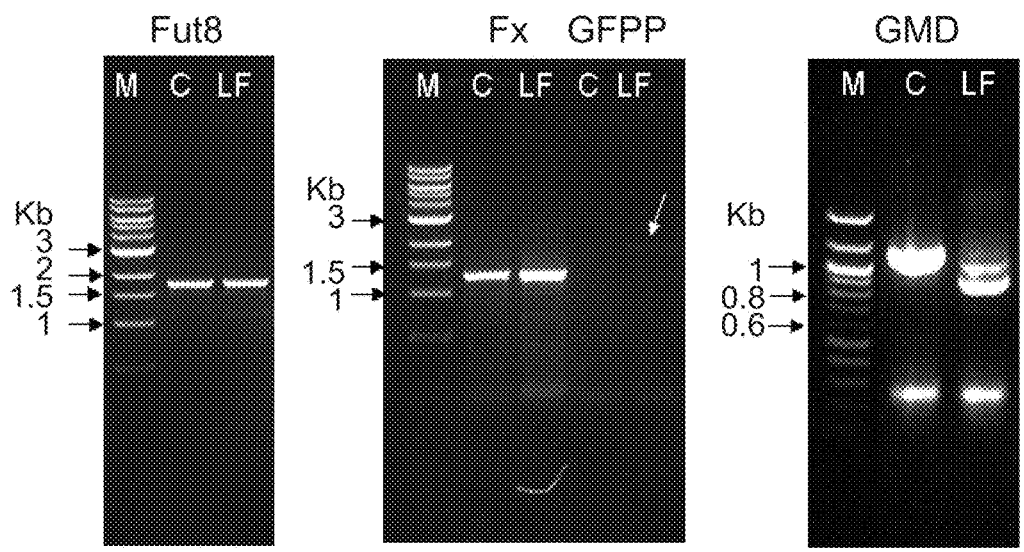
FIG. 21 is a photograph illustrating RT-PCR analysis of fucosylation pathway genes. Total RNA was isolated from CHO-S (C) and ITL-LF2 (LF) cells and subjected to RT-PCR utilizing polydT followed by gene specific primers. The resulting products were run on an agarose gel and detected under UV light by SyberSafe™ staining. Expected sizes: Fut8—1.7 Kb; GMD—1.1 Kb; FX—1.2 Kb; GFPP—1.7 Kb; M—DNA size marker.

To analyze the fucosylation pathway genes expressed in ITL-LF2 in comparison to CHO-S parental cells, total RNA was extracted from both cell lines and subjected to reverse transcription (RT) following by PCR with gene-specific primers that capture the entire coding region. The resulting cDNAs were then run on agarose gels to analyze if there are differences in the sizes obtained from the parental CHO-S and ITL-LF2 cells. The bands that were obtained were further analyzed by sequencing. FIG. 21 shows the results obtained after RT-PCR for all four genes tested.

cDNAs of similar sizes were obtained for the GDP-4-keto-6-deoxy-D-mannose epimerase-reductase (Fx) and Alpha 1,6 fucosyltransferase (Fut8) genes. Sequencing analysis confirmed that both genes' cDNAs are identical in the two cell lines. GDP beta L fucose pyrophosphorylase (GFPP) was undetectable in CHO-S cells (checked in several RT-PCR analyses) but a very faint band at the expected size could be detected in the ITL-LF2 cells (arrow in FIG. 21). Sequencing was not carried out in this case.

For the GMD gene, a band at the expected size was detected in CHO-S cells, and sequencing revealed it to be the expected full length GMD mRNA. However, in ITL-LF2 cells two bands were detected (these two bands sometimes look as one "fat" band on a gel indicating a doublet), both smaller than the full length ORF. Sequencing revealed the presence of two splice variants: one (denoted splice variant 1—SV1) containing a deletion of exons 8 and 9 (FIG. 22A) and the second (splice variant 2—SV2) with a deletion in exons 3 and 4 (FIG. 22B). Protein sequences of the full length GMD and both splice variants are set forth in SEQ ID NOs: 23-25. DNA sequences of the full length GMD and both splice variants are set forth in SEQ ID NOs: 26-28. In addition a small band of ~250 bp was found in both CHO-S and ITL-LF2 cells. Due to the fact that this small band was detected in both cell types, this band does not seem to be the reason for the differences seen in glycosylation in both these cell types. Therefore this band was referred to as a "small" band but was not analyzed further.

Analysis of the GMD splice variants (SV) sequence revealed the presence of a unique restriction enzyme site for each splice variant (BglII on exon 4 and XmnI on exon 8 (see FIG. 23A). For further verification of the mRNA pattern in CHO-S and ITL-LF2 cells, additional RT-PCR was carried out from each cell type. The cDNA was then split into three equal parts, one untreated, the other digested with BglII and the third digested with XmnI. All reactions were then run on an agarose gel and bands were detected and compared to a DNA size marker (FIG. 23B). The rational behind this experiment was that if ITL-LF2 cells contain a mixture of the two SVs, digestion with one restriction enzyme will leave a higher band of the SV that does not contain the specific restriction site and additional new bands will appear at the expected sizes for the other SV that does contain the specific restriction site. Expected sizes of bands were obtained in all digestions, indicating that indeed in ITL-LF2 the two splice variants exist as a mixture. In addition the largest (higher) band after restriction (the SV that was not digested) was excised from the gel and sequenced. Results showed the presence of the SV expected in each case: SV2 remained as a higher band in the BglII digested fraction and SV1 remained in the XmnI digested fragment (for explanation of fragment sizes obtained see Table 6 herein below).

TABLE 6

| Lane # | Cell type | Uncut | Results of digested with BglII* | Results of digested with XmnI |
|---|---|---|---|---|
| 1 | CHO-S | 1.1 (full length) 0.25 ("Small" band) | | |
| 2 | ITL-LF2 | 0.9-0.92 (SV1 & SV2) 0.25 ("Small" band) | | |
| 3 | CHO-S | | 1.1 (non-digested full length fragment) 0.8 (digested fragment) 0.3 (digested fragment) 0.25 ("Small" band) | |
| 4 | ITL-LF2 | | 0.92 (SV2 non-digested) 0.59 (digested fragment) 0.31 (digested fragment) 0.25 ("Small" band) | |
| 5 | CHO-S | | | 0.86 (digested fragment) 0.26 (digested fragment + "small" band) |

TABLE 6-continued

| Lane # | Cell type | Uncut | Results of digested with BglII* | Results of digested with XmnI |
|---|---|---|---|---|
| 6 | ITL-LF2 | | | 0.91 (SV1 non-digested) 0.67 (digested fragment) 0.26 (digested fragment + "small" band) |

*BglII digestion of cDNA from CHO-S cells is incomplete

Figure 24:
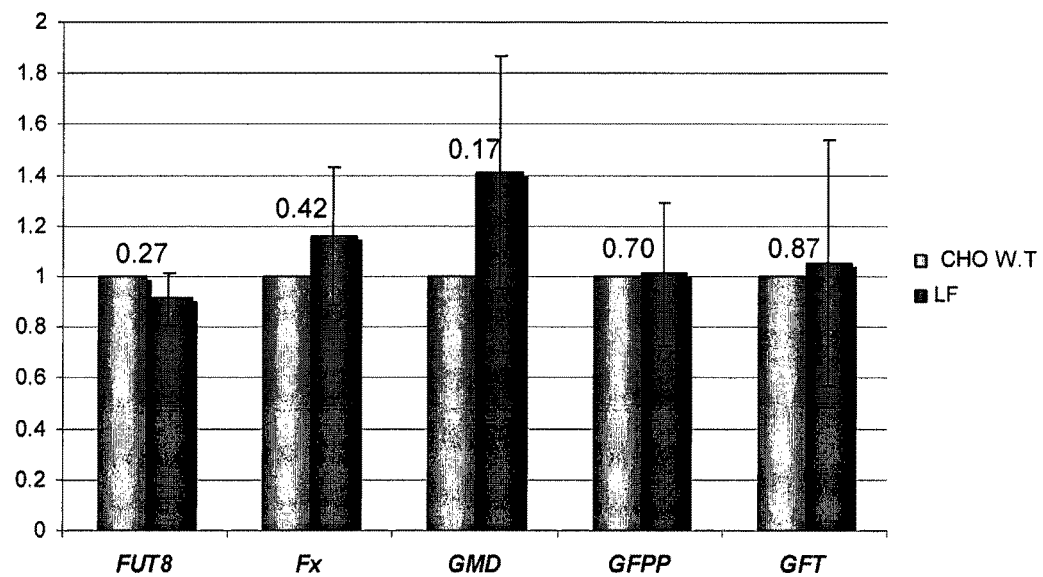
FIG. 24 is a graph illustrating the analysis of fucosylation pathway gene expression levels in ITL-LF2 cells vs. CHO-S cells by Q-PCR. cDNA was prepared from ITL-LF2 and CHO-S (control) RNA and subjected to Q-PCR analysis utilizing gene specific primers and probes that are situated on exons 5-6 (which are present in the full length GMD mRNA and both splice variants). The results for each gene were obtained from four separate RNA extractions, from cells plated on four different dates. From each extraction date, cDNAs were prepared and used for detection of all genes by Q-PCR. All samples were run in triplicates and normalized against a Beta-Actin endogenous control. Numbers above bars indicate P-values for each gene as calculated utilizing the paired Ttest statistical analysis. Significance is indicated by P-values<0.05.
RQ—Fold of change of expression from control.

Expression Levels of Genes Involved in Fucose Synthesis:

The expression level of genes involved in the fucosylation pathway was determined by Q-PCR with gene-specific primers and probes. No significant change was detected in expression levels of any of the genes tested (FIG. 24). The results indicate that changes in the fucosylation levels of the ITL-LF2 cells were not due to the GMD mRNAs expression level.

Preparation of a Pre-MCB (Preparations, Thawing, Sterility and *Mycoplasma* Testing):

ITL-LF2 cells generated following four cycles of low fucose selection by FACS were propagated and frozen. These cells were thawed in order to propagate them and to prepare a PreMCB. Pre-master cell bank (pre-MCBs) containing 60 ampoules with $10 \times 10^6$ cells per vial were prepared.

Viability, Sterility and *Mycoplasma* Testing of Pre-Master Cell Banks:

One ampoule from the pre-MCB of ITL-LF2 cells was thawed 11 days post freezing. Viability measured immediately after thawing was 98.3%. The cells were propagated for three growth cycles and found to be 99.0% viable, respectively.

The pre-MCBs were tested for sterility and *Mycoplasma* contamination. The bank was found to be sterile and *Mycoplasma* free.

Example 4

ITL-LF2 Cells Regain Fucosylation Upon Transfection with Wt GMD Gene

In ITL-LF2 cells it was found that the GMD gene (which is involved in the de-novo synthesis pathway of fucose) exhibited two splice variants and no full length mRNA, which differs from the pattern seen in CHO-S wild type cells. In order to evaluate whether the lack of full length GMD protein is the cause for the low fucose phenotype seen in ITL-LF2 cells, the cells were transfected with the full length GMD cDNA following by FACS analysis of the fucosylation levels.

Construction of Plasmid MB-129 (PCMV-P-GMD):

The full length GMD cDNA was created by RT-PCR on total RNA extracted from CHO-S wt cells utilizing the primers 586-26 and 587-22 depicted in Table 5, herein above. In order to clone this gene into the required vector, an additional step of PCR was carried out with primers 700-45 and 701-30 (for details see Table 7 herein below) that enabled addition of restriction enzyme (RE) sites (5'SwaI and 3'XhoI) required for the cloning step.

TABLE 7

| Construction of vector | Template used | Fragment obtained | 5' primer No. | Sequence* | 3' primer No. | Sequence* |
|---|---|---|---|---|---|---|
| MB-127 (pTT5-APERA-HC) | PGL3 APERA EMCV-PAC1-DHFR Tandem-872 | HindIII-APERAHC-NotI | 690-36 | GTCTGAAT TCAAGCTT GTAGCGAT CGCCGCCA CCAT SEQ ID NO: 41 | 691-38 | GGATCC<u>GC</u> <u>GGCCGCTA</u> CGCCGCCC TCAGATCT TTATCA SEQ ID NO: 44 |
| MB-128 (pTT5-APERA-LC) | PGL3 APERA EMCV-PAC1-DHFR Tandem-872 | HindIII-APERALC-NotI | 692-36 | GCTTGAAT TC<u>AAGCTT</u> CTAGTACG CGTGTTTA AACC SEQ ID NO: 43 | 693-32 | <u>GCGGCCGC</u> TGTCCGCG CCTTACTA ACACTCTC SEQ ID NO: 44 |
| MB-129 (pCMV-P-GMD) | cDNA of GMD from CHOwt cells | SwaI-GMD-XhoI | 700-45 | GTCCGATA TC<u>ATTTAA</u> <u>AT</u>CGCCAC CATGGCTC ACGCTCCC GCTAG SEQ ID NO: 45 | 701-30 | ATCC<u>CTCG</u> <u>AG</u>TTATCA GGCGTTGG GGTTGGTTC SEQ ID NO: 46 |

The PCR fragment was digested with SwaI and xhoI and ligated to vector pCMV-P that was digested with the same restriction enzymes.

Figure 25:
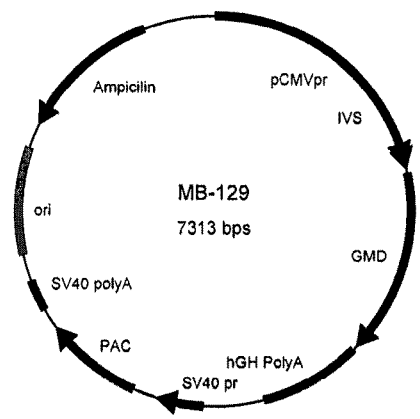
FIG. 25 is a schematic view of vector MB-129 (pCMV-P-GMD). The full length GMD cDNA from CHO-S wt was cloned into vector pCMV-P. pCMVpr—human CMV promoter. IVS—intron A of hCMV IE gene. PAC—puromycin resistance gene.

The resulting vector (MB-129) contains the GMD gene under the hCMV promoter with the puromycin resistance gene as a selection marker on a separate cassette as illustrated in FIG. 25.

Fucose expression of transfected cells: ITL-LF2 and CHO-S cells were transfected with linear plasmid containing the GMD coding sequence (pCMV-P-GMD) in triplicates using lipofectamine reagent. ITL-LF2 cells were recovered for three days in 50% C6614 (Sigma) and 50% C6366 (Sigma) supplemented with 13.6 mg/L Hypoxanthine/3.9 mg/L thymidine (HT) and 10 µg/ml fucose. Then the transfected cells were selected in 50% C6614 (Sigma) and 50% C6366 (Sigma) supplemented with 10 µg/ml fucose and 10 µg/ml Puromycin. After full recovery the ITL-LF2 transfected pools were transferred to ProCHO5 medium containing 10 µg/ml Puromycin without fucose.

Figure 26:
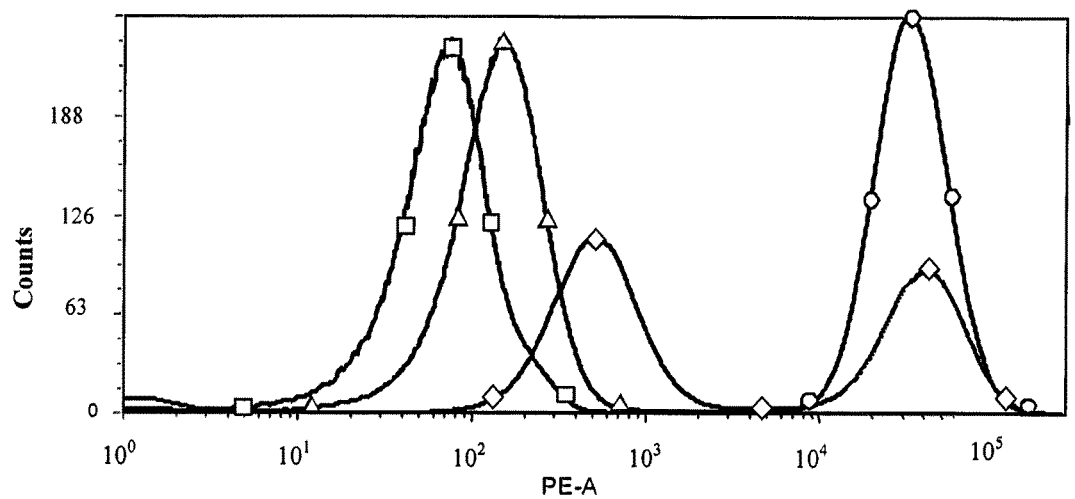
FIG. 26 is a graph illustrating that ITL-LF2 regains fucosylation upon transfection with wild type GMD cDNA. ITL-LF2 cells were transfected with vector containing GMD cDNA (pCMV-P-GMD) in C6614 medium in the presence of fucose. The transfected cells were transferred to ProCHO5 medium in the absence of fucose. The cells were analyzed by FACS following labeling with biotinylated AAL and fluorescent streptavidin. CHO-S, not labeled (□), CHO-S (○), ITL-LF2 (Δ), GMD transfected ITL-LF2 cells (◇).

The fucosylation level was analyzed by FACS on ITL-LF2 GMD transfected cells and compared with the fucosylation levels of CHO-S (positive control) and ITL-LF2 (negative control) cells (FIG. 26). The results demonstrate that approximately 45% of the population express proteins with fucosylation levels similar to those of CHO-S cells. The rest of the population (~55%) shows lower fucosylation levels. Nevertheless, the population with the low fucosylation level had higher fucocylation levels than that of ITL-LF2 non-transfected cells. The above results indicate that fucosylation was reconstituted in ITL-LF2 cells following transfection with GMD containing plasmid and confirms that the defect in the GMD mRNA was the reason for the low fucosylation level on ITL-LF2 cells. The reason for the existence of two sub-populations of ITL-LF2 GMD transfected cells that have different fucosylation level may derive from the stringency of the puromycin selection. It is assumed that both low and high fucosylated subpopulations express puromycin N acetyl transferase (PAC) in a sufficient amount to survive the puromycin selection, but there might be no direct correlation between the PAC and the GMD expression. Therefore, the two subpopulations express different levels of GMD protein that results in different levels of fucosylation.

Example 5

Analysis of ITL-LF2 Cells Following Stable and Transient Transfections

Stable Transfections of ITL-LF and CHO-S Cells

Figure 27:
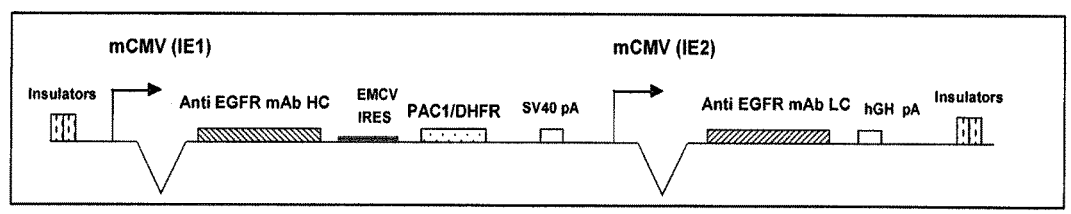
FIG. 27 is a diagram illustrating the anti EGFR mAb containing plasmid-PGL3 anti EGFR mAb-EMCV-PAC1-DHFR Tandem. Linear plasmid containing the LC and HC of anti EGFR mAb was used for transfection of CHO-S and ITL-LF2. mCMV—murine cytomegalovirus promoter, EMCV—encephalomyocarditis virus, IRES—internal ribosome entry site, PAC—puromycin N-acetyltransferase, DHFR—dihydrofolate reductase, HC—heavy chain, LC—light chain, SV40—simian virus 40, pA—polyadenylation.

ITL-LF2 and CHO-S cells were transfected with linear plasmid containing the anti EGFR mAb coding sequence (PGL3 anti EGFR mAb EMCV-PAC1-DHFR Tandem) in triplicates (FIG. 27) using lipofectamine reagent.

ITL-LF2 cells were recovered for three days in 50% C6614 (Sigma) and 50% C6366 (Sigma) supplemented with 13.6 mg/L Hypoxanthine/3.9 mg/L thymidine (HT) and 10 µg/ml fucose. Then the transfected cells were selected in 50° A) C6614 (Sigma) and 50% C6366 (Sigma) supplemented with 10 µg/ml fucose and 5-10 µg/ml Puromycin. After eight days the cells were transferred to C6614 medium with 10 µg/ml fucose and 25 µg/ml Puromycin. After full recovery the ITL-LF2 transfected pools were combined in order to create a combined pool of low fucose transfected cells. Fucose was removed from the medium and later on the cells were transferred to ProCHO5 medium containing 10 µg/ml Puromycin.

CHO-S cells were recovered for three days in ProCHO5 medium (Sigma) supplemented with 27.2 mg/L Hypoxanthine/7.8 mg/L thymidine (HT) and 10 µg/ml fucose. Then the transfected cells were selected in ProCHO5 medium supplemented with 10 µg/ml fucose and 25 µg/ml Puromycin. After 12 days the CHO-S cells were fully recovered.

Figure 28:
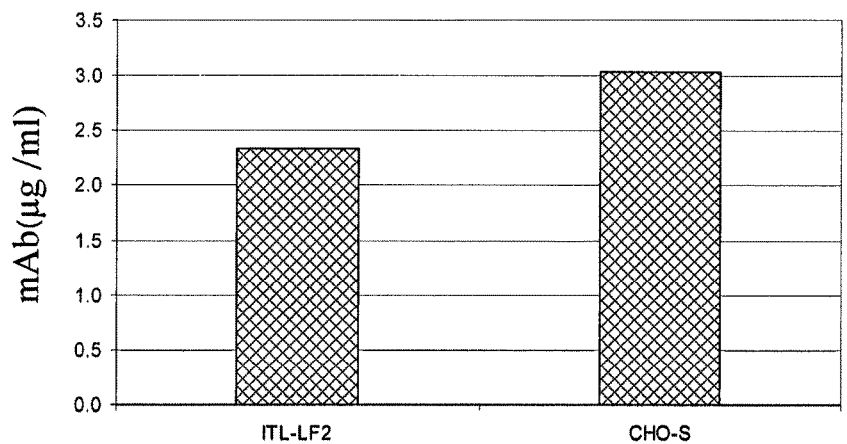
FIG. 28 is a diagram illustrating stable expression of anti EGFR mAb in ITL-LF2 and CHO-S pools. ITL-LF2 and CHO-S were transfected with anti EGFR mAb containing vector (PGL3 anti EGFR mAb EMCV-PAC1-DHFR Tandem). After recovery, productivity was evaluated in pools.

Recombinant antibody expression was analyzed by ELISA was found to be only slightly lower in ITL-LF2 cells in comparison to CHO-S transfected cells (FIG. 28).

Figure 29:
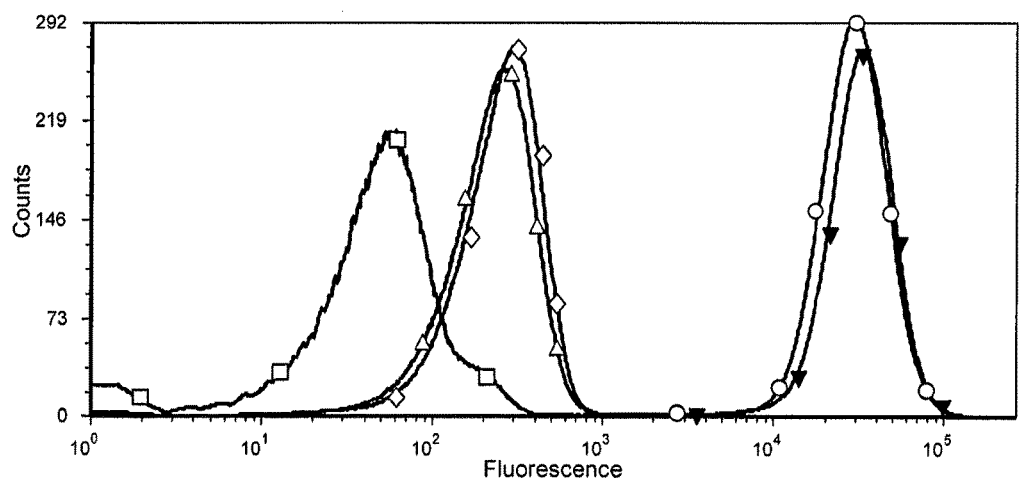
FIG. 29 is a graph illustrating FACS analysis of fucose levels on ITL-LF2 anti EGFR mAb transfected cells. Analysis of fucose levels on the membrane of anti EGFR mAb transfected cells propagated in C6614 medium before and after removal of fucose. CHO-S, not labeled (□), CHO-S in ProCHO5 (○), ITL-LF2 in C6614 (Δ), ITL-LF2 anti-EGFR mAb transfected in C6614 in the presence of fucose (▼), ITL-LF2 anti-EGFR mAb transfected in C6614 in the absence of fucose (Δ).

FACS Analysis of Fucose Level on Anti EGFR mAb Transfected Cells' Membrane:

Analysis of fucose levels on cells' membrane of anti EGFR mAb transfected cells propagated in C6614 medium before and after removal of fucose shows that upon fucose removal fucosylation declines to the initial low level obtained in the absence of fucose (FIG. 29).

FACS Analysis of Sialic Acid Level on Anti EGFR mAb Transfected Cells' Membrane:

The analysis showed that after transfection and following labeling of cells with a sialic acid specific lectin: FITC conjugated MAA, both CHO-S and ITL-LF2 anti EGFR transfected cells present similar levels of sialic acid on their cells' membrane. These levels are also similar to the levels of CHO-S and ITL-LF2 untransfected cells (FIG. 30).

Construction of pTT5-Anti EGFR mAb Vectors for Transient Transfections:

For the transient transfections of anti EFGR mAb into ITL-LF2 cells, two vectors were constructed on the backbone of the pTT5 vector. One vector contained the light chain (LC) and the other the heavy chain (HC) of the EFGR mAb antibody.

To create vector MB-127, a PCR fragment of 1476 bp containing the EFGR mAb HC was created utilizing primers 690-36 & 691-38 on vector PGL3 anti EGFR mAb EMCV-PAC1-DHFR Tandem—872. The fragment was digested with HindIII and NotI and ligated into vector pTT5 that was digested with the same RE. The resulting vector can be seen in FIG. 31A.

To create vector MB-128, a PCR fragment of 762 bp containing the EFGR mAb LC was created utilizing primers 692-36 & 693-32 on vector PGL3 anti EGFR mAb EMCV-PAC1-DHFR Tandem—872. The fragment was digested with HindIII and NotI and ligated into vector pTT5 that was digested with the same RE. The resulting vector can be seen in FIG. 31B.

Figure 32:
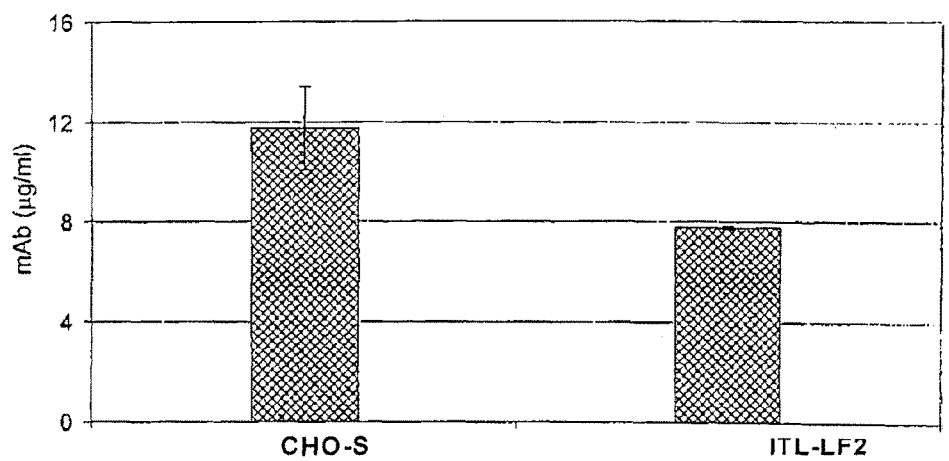
FIG. 32 is a bar graph illustrating transient expression of anti EGFR mAb in ITL-LF2 and CHO-S cells. ITL-LF2 and CHO-S cells were transiently transfected with anti EGFR mAb containing PTT5 vector in ProCHO5 medium. The transfection conditions were specific to the cell type. ITL-LF2 cells were supplemented with VPA and transferred to 31° C. and CHO-S were supplemented with VPA and cell boost 24 hours post transfection.

Transient Transfections of ITL-LF and CHO-S Cells:

ITL-LF2 and CHO-S cells were transfected with anti EGFR mAb containing PTT5 vector (FIG. 30B) using PEI reagent in triplicates. Then two transfection protocols were performed:

Transfection in ProCHO5:

CHO-S and ITL-LF2 cells were transfected in medium containing ProCHO5 at 37° C. and twenty four hours post transfection CHO-S cells were supplemented with valproic acid and incubated at 31° C. The protein concentration in ITL-LF2 and CHO-S cells under the above stated conditions was 12.5 µg/ml and 25 µg/ml, respectively (FIG. 32).

Example 6

Analysis of Recombinant Antibodies

Figure 33:
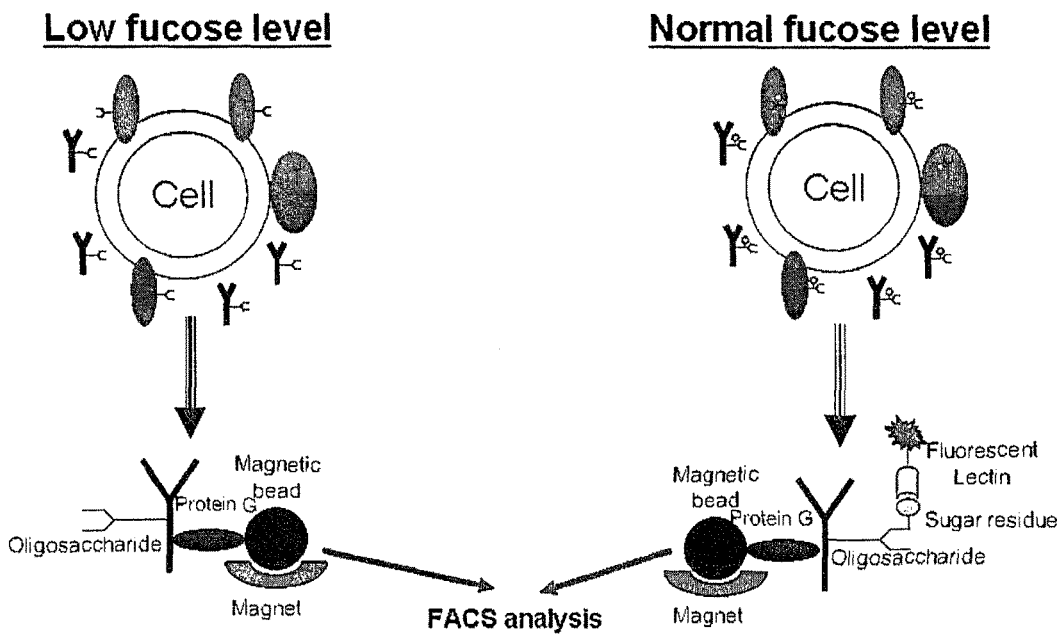
FIG. 33 is an illustration depicting analysis by FACS of sugar residue levels on antibodies. Crude harvest or purified antibody samples were mixed with protein G coated magnetic beads followed by binding to fluorescently label lectin. The fucose levels were determined by FACS according to the fluorescence.

Analysis of Fucose and Sialic Acid Levels on Crude Material or Purified Antibodies by FACS:

Crude or purified material containing antibodies were bound on protein G magnetic beads followed by staining with a fluorescently labeled specific lectin (as illustrated in FIG. 33). The antibody samples were analyzed by FACS in order to detect the sugar residue levels.

Analysis by FACS of Fucose Level on Crude Harvest Material from Transiently Transfected Cells:

Crude harvest samples from transient transfection were concentrated by spin filter (Amicon ultra cat# UFC801024) in order to reach a concentration above 25 µg/ml. Analyses were done as indicated in the Methods section at protein product concentration of 32-37 µg/ml. The results show clearly that the ITL-LF2 transfected cells express anti EGFR mAb protein with low fucose levels (FIG. 33) similar to those of material from stably transfected cells (FIG. 37) and in correlation with the levels detected on the cells' membrane (FIG. 29).

Analysis by FACS of Fucose Level on Crude Harvest from Stable Pools:

Crude harvest samples prepared from cell culture batch were collected. Analyses were done by FACS as described in the Methods section at a protein concentration of 25 µg/ml. The results show clearly that the ITL-LF2 transfected cells express anti EGFR mAb protein with low fucose levels (FIG. 35) similar to those of material from transiently transfected cells (FIG. 34) and in correlation with the levels detected on the cells' membrane (FIG. 29).

Analysis by FACS of Sialic Acid Level on Crude Harvest of Stable Pools:

Crude harvest samples prepared from cell culture batch were collected. Analyses were done by FACS as described in the Methods section at a protein concentration of 25 µg/ml. The results show clearly that the ITL-LF2 and CHO-S transfected cells express anti EGFR mAb protein with similar sialic acid levels (FIG. 36) in correlation with the levels detected on the cells' membrane (FIG. 30).

Figure 34:
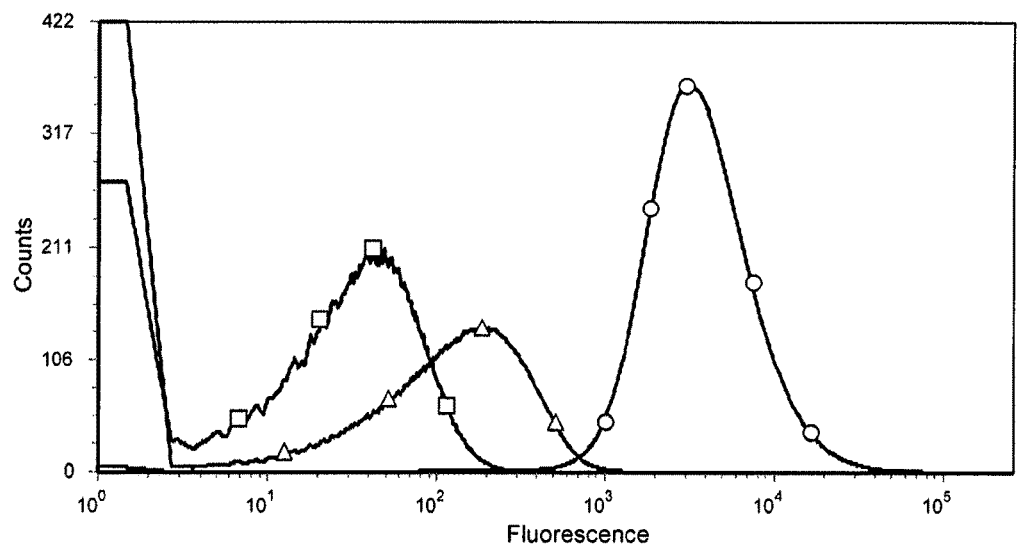
FIG. 34 is a graph illustrating analysis by FACS of fucose levels on anti EGFR mAb transiently expressed in ITL-LF2 and CHO-S. Crude harvest samples were mixed with protein G coated magnetic beads following by binding to biotinylated AAL and fluorescent streptavidin mixture. The fucose levels were determined by FACS according the fluorescence levels. Magnetic beads (□), anti EGFR from CHO-S transfected cells (○), anti EGFR from ITL-LF2 transfected cells (Δ).
Figure 35:
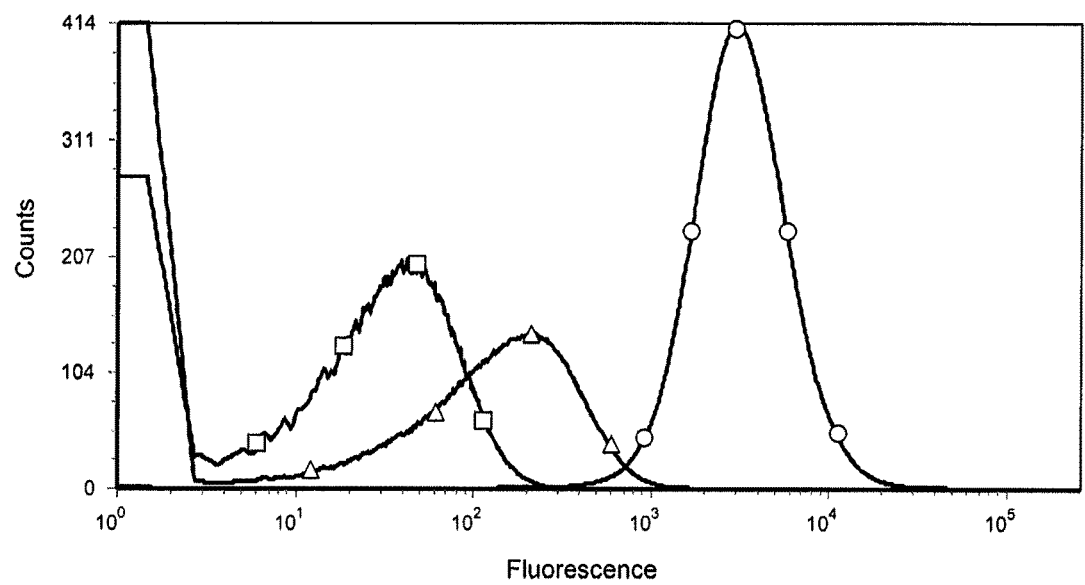
FIG. 35 is a graph illustrating analysis by FACS of fucose levels on crude harvest from anti EGFR mAb stably expressed in ITL-LF2 and CHO-S cultures. Crude harvest samples were mixed with protein G magnetic beads following by binding to biotinylated AAL and fluorescent streptavidin mixture. The fucose levels were determined by FACS according the fluorescence levels. Magnetic beads (□), anti EGFR mAb from CHO-S transfected cells (○), anti EGFR mAb from ITL-LF2 transfected cells (Δ).
Figure 37:
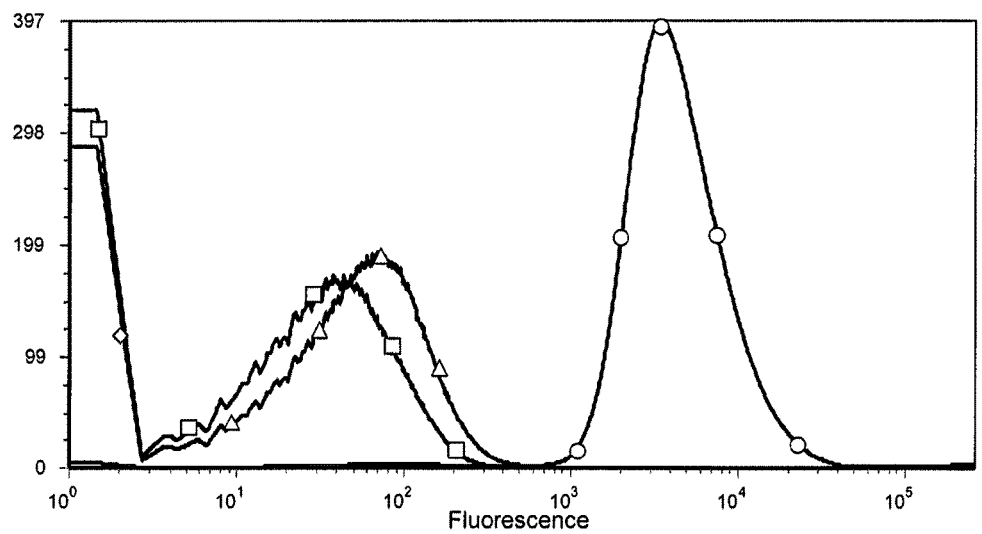
FIG. 37 is a graph illustrating FACS analysis of fucose levels on anti EGFR mAb stably expressed in ITL-LF2 and CHO-S. Purified antibody samples were mixed with protein G magnetic beads followed by binding to biotinylated AAL and fluorescent streptavidin mixture. The fucose levels were determined by FACS according to the fluorescence levels. Magnetic beads (□), anti EGFR mAb from CHO-S transfected cells (○), anti EGFR mAb from ITL-LF2 transfected cells (Δ).

Analysis by FACS of Fucose Level on Purified Product:

FACS analysis of anti EGFR mAb purified product from stably transfected ITL-LF2 cells showed low fucose levels whereas purified product from parent CHO-S cells contained normal fucose levels (FIG. 37). The fucose levels are in correlation with the levels detected on the cells' membrane (FIG. 29) and in crude material (FIG. 34).

Figure 36:
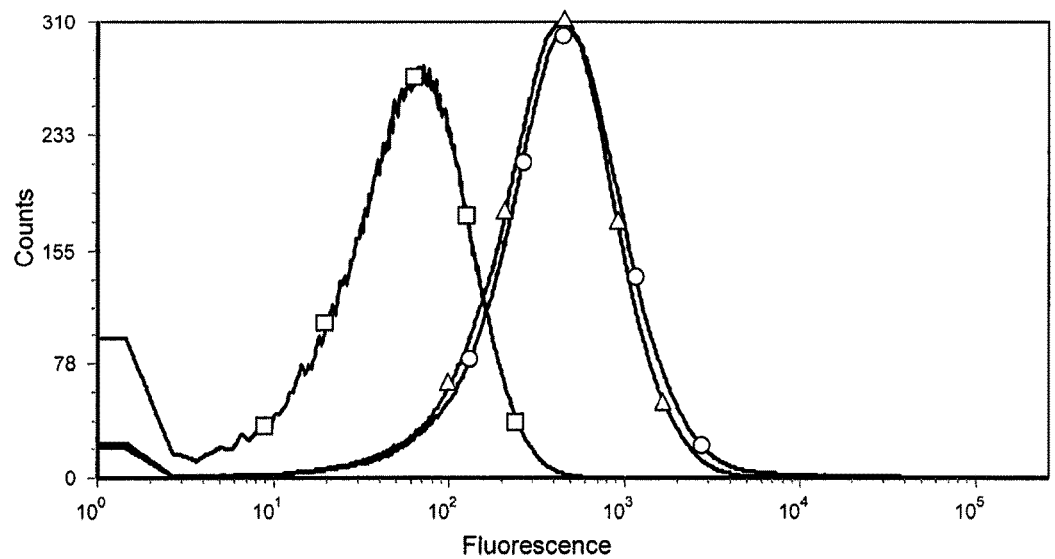
FIG. 36 is a graph illustrating analysis by FACS of sialic acid levels on crude harvest from anti EGFR mAb stably expressed in ITL-LF2 and CHO-S cultures. Crude harvest samples were mixed with protein G magnetic beads followed by binding to FITC conjugated MAA. The sialic acid levels were determined by FACS according the fluorescence levels. Magnetic beads (□), crude harvest from CHO-S transfected cells (○), crude harvest from ITL-LF2 transfected cells.
Figure 38:
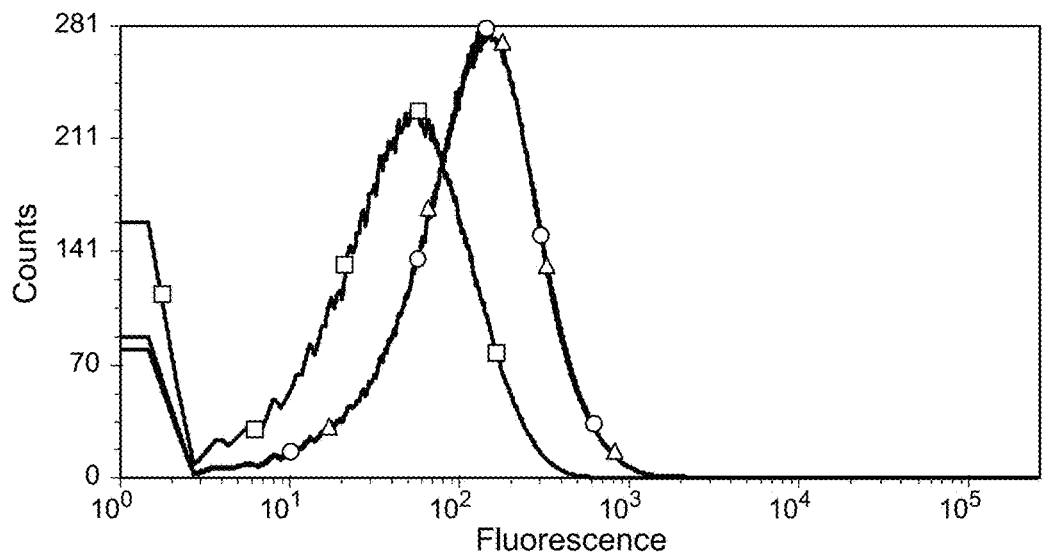
FIG. 38 is a graph illustrating FACS analysis of sialic acid levels on anti EGFR mAb stably expressed in ITL-LF2 and CHO-S. Purified antibody samples were mixed with protein G magnetic beads followed by binding to FITC conjugated MAA. The sialic acid levels were determined by FACS according the fluorescence levels. Magnetic beads (□), anti EGFR from CHO-S transfected cells (○), anti EGFR from ITL-LF2 transfected cells (Δ).

FACS Analysis of Sialic Acid Level on Purified Material:

FACS analysis of anti EGFR mAb purified material from stably transfected cells showed similar sialic acid levels on material from both ITL-LF2 and CHO-S cells (FIG. 38). The sialic acid levels are in correlation with the levels detected on the cells' membrane (FIG. 30) and in crude material (FIG. 36).

Determination of Fucose Levels on Intact Anti-EGFR mAb by Octet:

The intact anti-EGFR mAb purified fraction eluted from the Protein A column was dialyzed against formulation buffer and concentrated. Fucose level on the intact purified anti-EGFR mAb produced by either wild type CHO-S cells or ITL-LF2 was determined by binding anti-EGFR mAb to biotinylated aleuria aurantia lectin (AAL). The assay was performed on the Octet QK system using the kinetic analysis module. First, the biotinylated-AAL was bound to a streptavidin coated biosensor, and then the fucose on the anti EGFR antibody was bound to the AAL lectin. Analysis of the intact anti-EGFR mAb enables detection of the Fab fucosylation residue only, since the fucosylation site (ASN 297) located on the Fc region is not accessible to the AAL (data not shown). In order to detect the fucosylation site on the Fc region an Fc monomer should be prepared.

Figure 39:
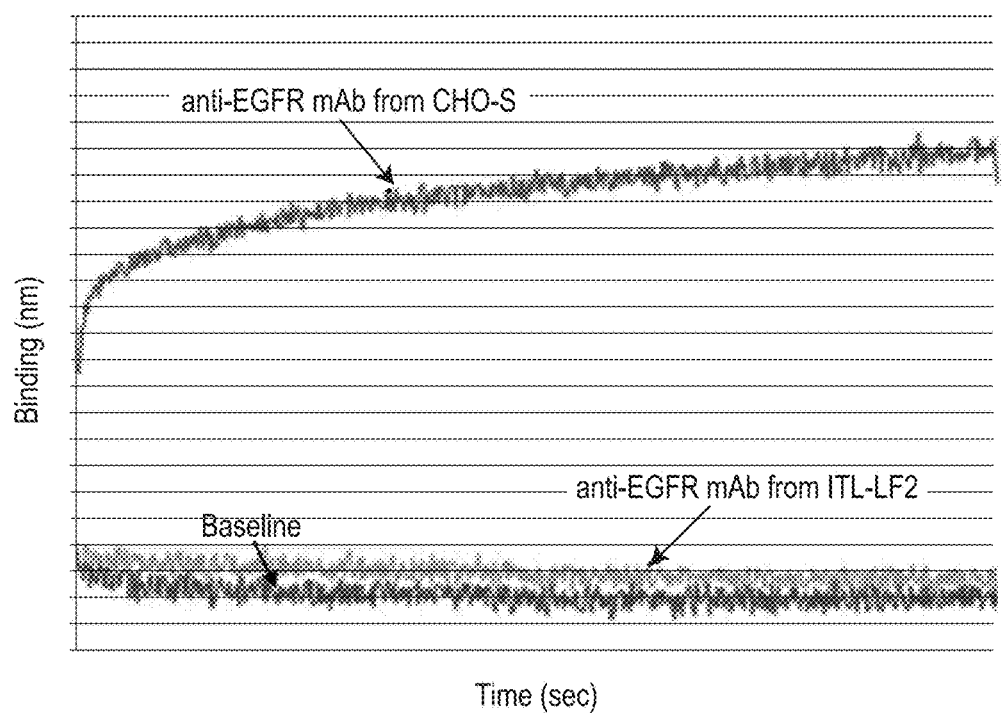
FIG. 39 is a readout of the Octet analysis of fucose levels on the purified intact anti-EGFR mAb. Purified products of anti-EGFR mAb from CHO-S and ITL-LF2—225 µg/ml by O.D 280 were bound to Biotinylated AAL (2 µg/ml) that was previously attached to strepavidin precoated biosensors. The graph represents the association step of the kinetic analysis by the Octet QK system. Each curve represents a specific sample marked by an arrow.
Figure 40:
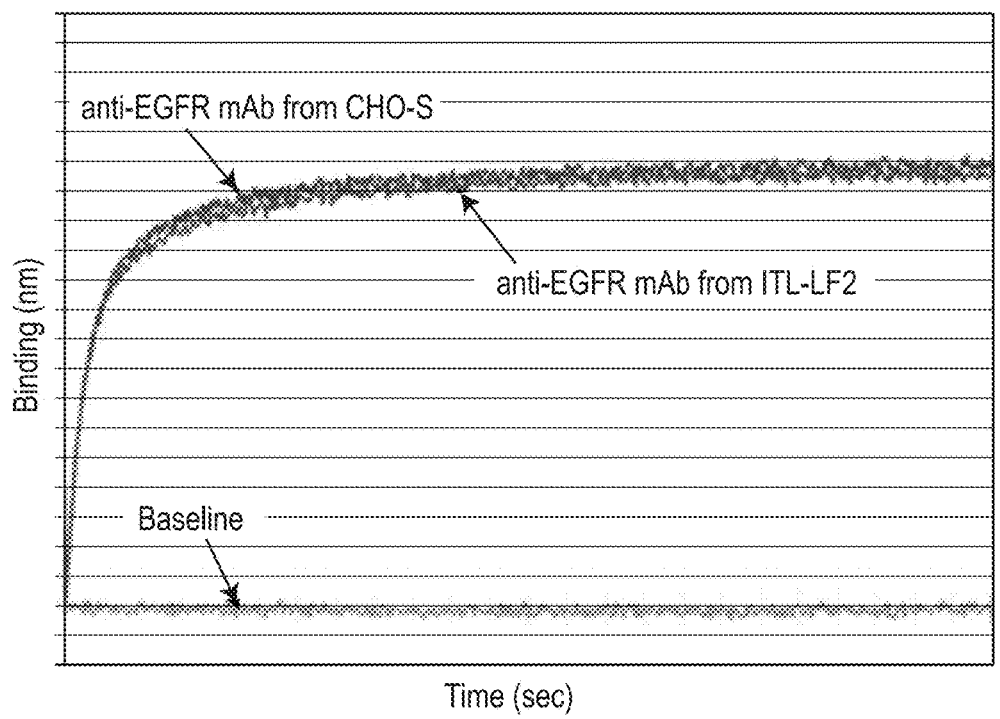
FIG. 40 is a readout of the Octet analysis of sialic acid levels on the purified intact anti-EGFR mAb. Purified products of anti-EGFR mAb from CHO-S and ITL-LF2 cells—115 µg/ml by O.D 280 were bound to Biotinylated-MAA (10 µg/ml) that was previously attached to streptavidin precoated biosensors. The graph represents the association step of the kinetic analysis by the Octet QK system. Each curve represents a specific sample marked by an arrow.

The results demonstrate the low fucose levels on intact anti EGFR mAb produced by the ITL-LF2 cells, relative to the product produced by CHO-S transfected cells (FIG. 39).

Determination of the Sialic Acid Levels on Intact Anti-EGFR mAb by Octet:

The anti-EGFR mAb produced by either wild type CHO-S cells (WT) or ITL-LF2 cells was evaluated for sialylation levels. Intact anti-EGFR mAb purified fraction eluted from the Protein A column was dialyzed against formulation buffer and concentrated. The sialic acid levels on the intact purified anti-EGFR mAb was determined by binding the product to biotinylated Maackia amurensis lectin (MAA). The assay was performed on the Octet QK system using the kinetic analysis module. First, the biotinylated-MAA was bound to a streptavidin-coated biosensor, and then the sialic acid on the anti EGFR mAb was bond to the MAA lectin. The results (FIG. 40) show that the sialic acid levels are similar on both products produced by ITL-LF2 and CHO-S cells. The results imply that the only difference in the product produced by ITL-LF2 and CHO-S cells is the level of fucose, whereas the entire glycosylation profile was probably not changed.

Figure 41:
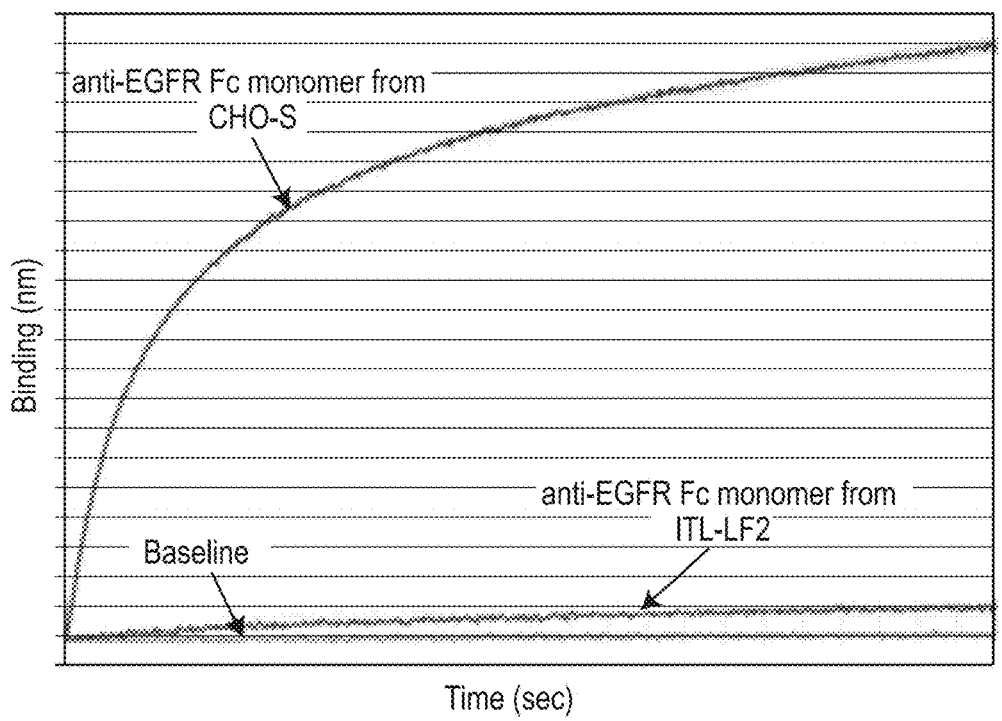
FIG. 41 is a graph of the analysis of fucose levels on the purified anti-EGFR Fc monomer by Octet. The Fc fraction of anti-EGFR mAb from CHO-S cells and from ITL-LF2 cells 40 µg/ml by O.D. 280 were bound to Biotinylated AAL (1 µg/ml) that was previously attached to Streptavidin precoated biosensors. The graph represents the association step of the kinetic analysis by the Octet QK system. Each curve represents a specific sample marked by an arrow.

Determination of Fucose Levels on Anti-EGFR Fc Monomer by Octet:

The Fc fractions of anti-EGFR were prepared by Papain cleavage of the intact antibody, then reduction and alkylation were followed by dialysis and concentration steps. The Fc monomer fractions were prepared from product produced by wild type CHO-S cells, ITL-LF2 cells. The fucose levels on the Fc monomer were determined by binding the fractions to biotinylated-AAL that was previously attached to streptavidin-coated biosensors of the Octet QK. The results demonstrate the low fucose level on anti EGFR Fc monomer from ITL-LF2 cells, relative to the product produced by CHO-S cells (FIG. 41).

Figure 42:
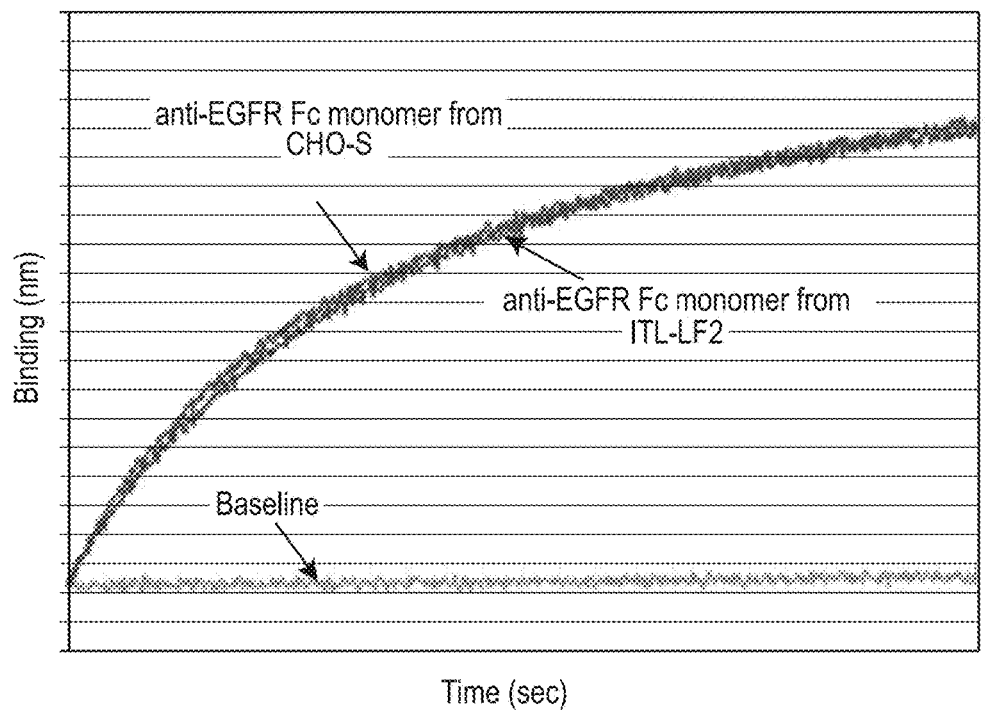
FIG. 42 is a graph of the analysis of the sialic acid levels on purified anti-EGFR Fc monomer by Octet. The Fc fraction of anti-EGFR mAb from CHO-S cells and from ITL-LF2 cells—250 µg/ml by O.D 280 were bound to Biotinylated MAA (10 µg/ml) that was previously attached to streptavidin precoated biosensors. The graph represents the association step of the kinetic analysis by the Octet QK system. Each curve represents a specific sample marked by an arrow.

Determination of Sialic Acid Levels on Anti-EGFR Fc Monomer by Octet:

The Fc fractions of anti-EGFR mAb were prepared by Papain cleavage of intact antibody, then reduction and alkylation were followed by dialysis and concentration. The Fc dialyzed and concentrated monomer fractions were prepared from product produced by wild type CHO-S, ITL-LF2 cells. The fucose level on the Fc monomer was determined by binding the fractions to a biotinylated-MAA that was previously attached to streptavidin-coated biosensors of the Octet QK system. The results show similar sialylation levels on the Fc fraction purified from both CHO-S and ITL-LF2 cells (FIG. 42).

Figure 43:
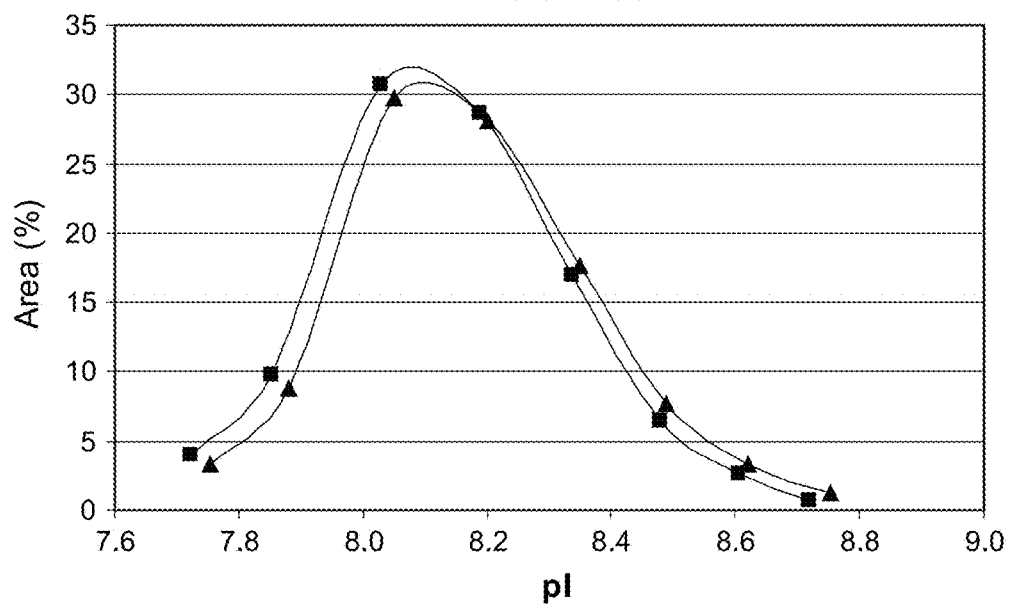
FIG. 43 is a graph showing the results of the charge profile analysis of anti-EGFR mAb purified product by iCE280. Purified products of anti-EGFR mAb from CHO-S cells (■) and from ITL-LF2 cells (▲) 0.4 mg/ml by O.D 280 were analyzed by iCE280. Dots represent % of peak area of isoforms in the iCE280 profile (note that the lines in the figure do not represent continuous functions and were added just to make it easier to follow the isoforms of the same product).

Capillary Isoelectric Focusing of Purified Product from Anti-EGFR Pools:

The anti-EGFR mAb product produced by wild type CHO-S or ITL-LF2 cells was purified on a Protein A column, dialyzed against formulation buffer and concentrated. The charge profile of the intact products was analyzed by capillary electrophoresis on iCE 280. FIG. 43 shows the comparison between the pI values of the purified products from CHO-S cells, ITL-LF2 cells. The results demonstrate that the charge profile of product produced by the CHO-S and ITL-LF2 cells are similar, while the reference sample seems to be slightly more basic compared to them, probably due to the difference in the cell lines and culture conditions.

Mass Spectrometry Analysis of Anti-EGFR Fc Fractions:

The purified anti-EGFR intact mAb, was cleaved by Papain to produced Fc and Fab fractions, then the Fc fraction was purified followed by dialysis and concentration. The anti-EGFR Fc samples from wild type CHO-S and ITL-LF2 cells were analyzed at EMD Serono Research Center (Billerica, USA) by mass spectrometry for evaluation of the fucosylation level at the conserved Fc region glycosylation site. The observed glycan structures were mainly biantennary with 0, 1 and 2 galactoses G0-F, G1-F and G2-F respectively as described in FIG. 44. The galactose level is higher in the CHO-S derived material as indicated by the higher fraction with one and mainly two galactose residues. The results show that the IgG Fc region of product produced by wild type CHO-S cells was fully fucosylated while the Fc region of product produced by ITL-LF2 cells was afucosylated.

Example 7

Figure 46:
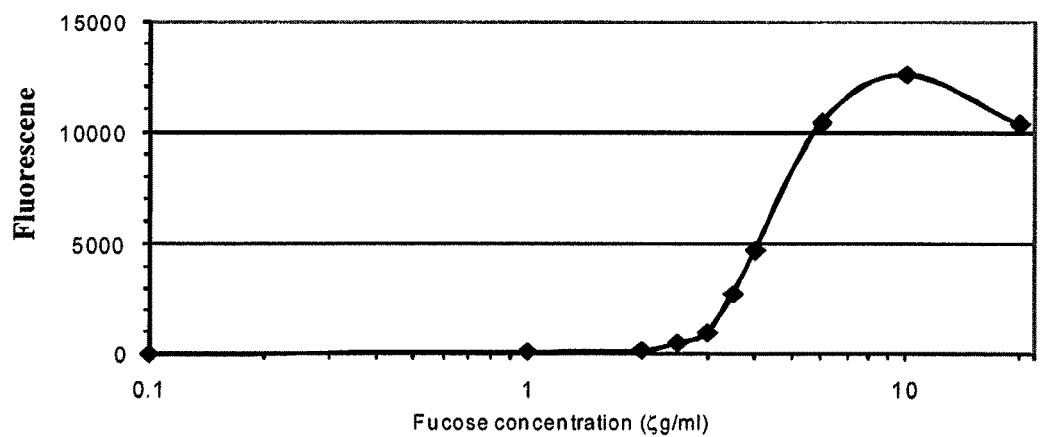
FIG. 46 is a graph illustrating the effect of exogenous fucose had on the fucosylation level EGFR mAb.

Effect of Exogenous Fucose Addition on Fucosylation Level of ITL-LF2 Anti EGFR mAb Transfected Cells ITL-LF2 anti EGFR mAb transfected cells were seeded in ProCHO5 medium in the presence of increasing concentrations of L-fucose in the culture medium. The cells as well as crude material were analyzed 4 days after cell seeding. FACS analysis results show correlation between the exogenously added fucose concentration and the fucosylation level on the cells' membrane (FIG. 45) as well as on the recombinant anti EGFR mAb (FIG. 46). Maximum fucosylation was obtained at 10 µg/ml fucose on both cells and recombinant anti EGFR mAb. The lowest fucosylation levels were detected on cells at 1 µg/ml external fucose, whereas on recombinant anti EGFR mAb the lowest fucosylation level was detected at higher concentration of 2.5 µg/ml external fucose.

Figure 47:
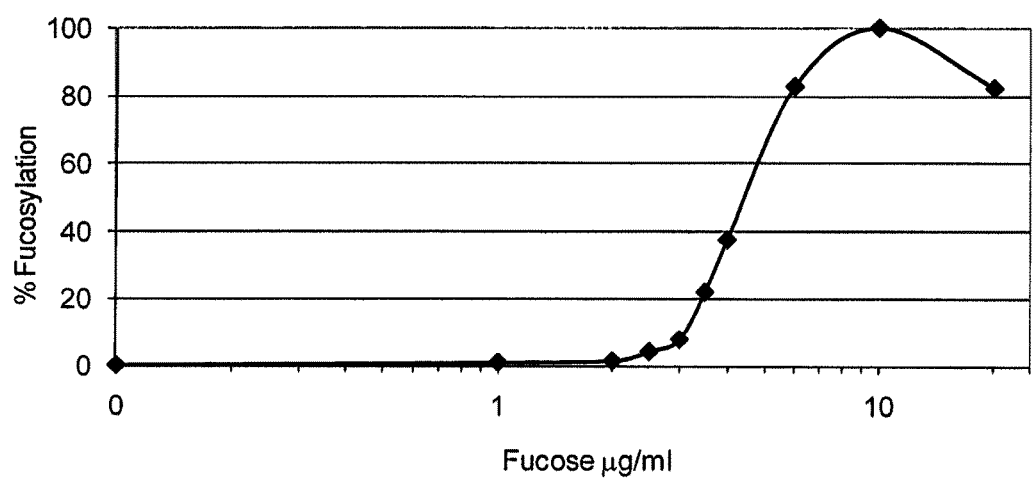
FIG. 47 is a calibration curve of fucosylation level on anti EGFR mAb according to the external fucose added.

Based on the above results, a calibration curve was created where maximum fluorescence was interpreted as 100% fucosylation, and the sample obtained without fucose was determined as 0 fucosylation. The fluorescence level at 0% external fucose was subtracted from the fluorescence level obtained at each external fucose concentration and then the percentage of fucosylation was calculated as the fluorescence level at each fucose concentration devided by the fluorescence level at 100% fucosylation (fucose saturation). A curve was drawn from these figures (FIG. 47).

Figure 48A:
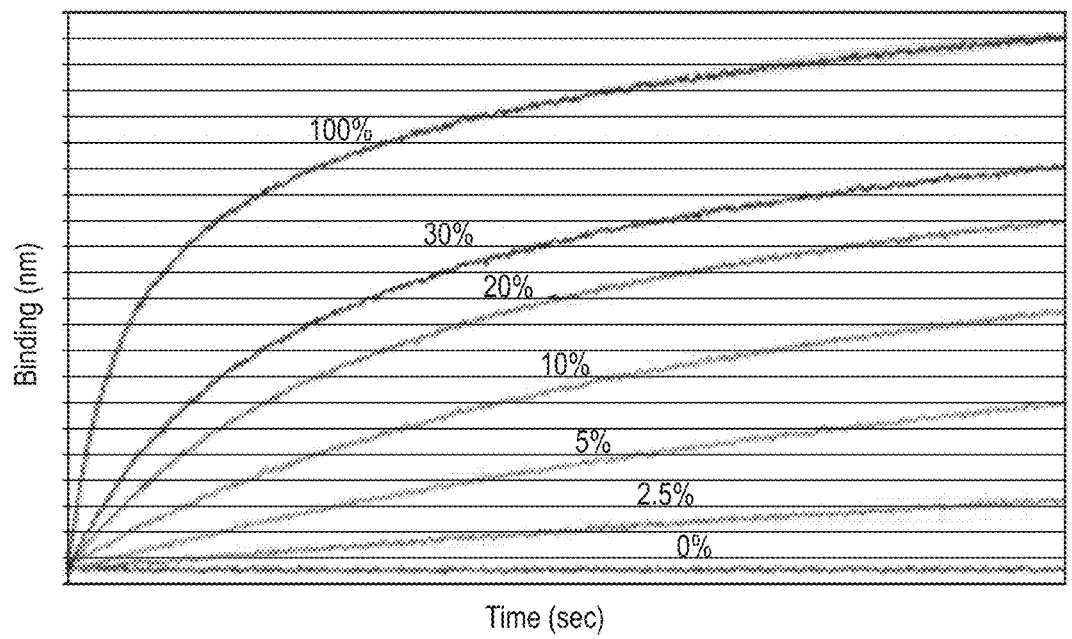
FIGS. 48A-B are calibration curves of fucose levels on purified anti-EGFR Fc monomer by Octet. Samples were prepared by mixing product from the Fc monomer fraction of anti-EGFR mAb from CHO-S cells and from ITL-LF2 cells 40 µg/ml by O.D. 280. Samples were bound to Biotinylated AAL (1 µg/ml) that was previously attached to Streptavidin precoated biosensors. The graph represents the association step of the kinetic analysis by the Octet QK system. Each curve corresponds to a specific % of fucose in the sample (A). Linear curve presentation (B).
Figure 48B:
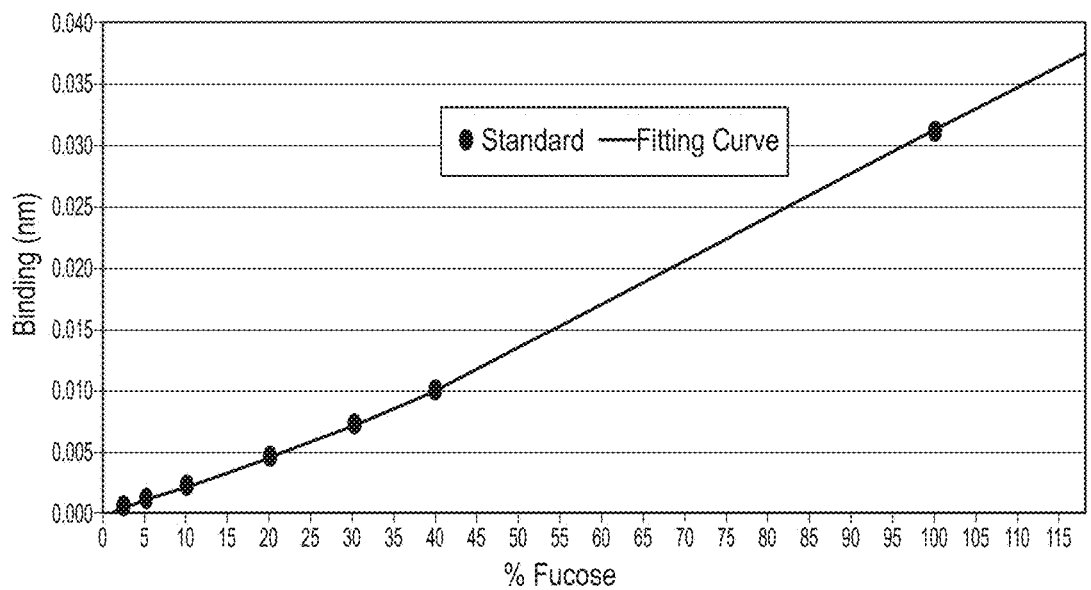

Calibration Curve of Fucosylated and Afucosylated Anti EGFR mAb Fc Monomer Based on the Octet QK Results:

The Fc fractions of anti-EGFR were prepared by Papain cleavage of the intact antibody, followed by reduction, alkylation dialysis and concentration. The Fc monomer fractions were prepared from product produced by wild type CHO-S cells and ITL-LF2 cells. Samples for the calibration curve were prepared by mixing different ratios of product from CHO-S cells (pool 100% fucose) and product from ITL-LF2 cells (0% fucose). The fucose levels on each sample were determined by binding the mixed sample to biotinylated-AAL that was previously attached to streptavidin-coated biosensors of the Octet QK system. The association step of the kinetic analysis was performed by the Octet QK system. Each curve corresponds to a specific % of fucose in the sample (FIG. 48A). The linear correlation between the binding level and the % of fucosylated material in the calibration curve (FIG. 48B) can serve for calculations of the fucosylated level of required samples. The results show that the assay is sensitive and can distinguish with high resulation between close levels of fucose. The linear correlation between the binding level and the % of fucosylated material imply that a required percentage of fucosylation can be obtained by addition of a certain exogenous fucose concentration.

Analysis of Partly Fucosylated Anti-EGFR Fc Monomer Fractions by Octet:

Following the results of the FACS analysis that shows correlation between the exogenously added fucose concentration and the fucosylation level on the cells' membrane, the fucose levels on the purified anti-EGFR mAb was determined by Octet. ITL-LF2 cells expressing anti EGFR mAb were cultured in 5 batches in parallel for 4 days in the presence of 3.5 µg/ml fucose and the medium was harvested. The anti-EGFR mAb was purified and cleaved by Papain followed by reducing and alkylation for isolation of the Fc monomer fraction. The fucose level was analyzed as described above. The results demonstrate that addition of 3.5 µg/ml fucose to the medium generates ~15% of fucosylation level with a variability of +/−0.5% in protein purified from five different batchs (FIG. 49). This indicates that the desired fucose level is reproducible.

Analysis of Partly Fucosylated Anti-EGFR Fc Monomer Fractions by Mass Spectrometry:

The fucosylation level on anti-EGFR mAb monomer fractions were analyzed by mass spectrometry. ITL-LF2 cells expressing anti EGFR mAb were cultured in 5 batches in parallel for 4 days in the presence of 3.5 µg/ml fucose and the medium was harvested. The anti-EGFR mAb was purified and cleaved by Papain followed by reducing and alkylation for isolation of the Fc monomer fraction as described above.

The observed glycan structures were mainly biantennary with 0, 1 and 2 galactose residues G0-F, G1-F and G2-F respectively as described in Table 8, herein below. The galactose level is higher in the CHO-S derived material as indicated by the higher fraction of one and mainly two galactose residues. The results demonstrate that addition of 3.5 µg/ml fucose to the medium induces 15.6% of fucosylation level with variability of +/−1.7% in protein from five different batchs. These results are in correlation with the results obtained by the Octet (FIG. 49). The results show that the IgG Fc region of product produced by wild type CHO-S cells was fully fucosylated while the Fc region of product produced by ITL-LF2 cells was afucosylated. Very good correlation was found between the Octet and the mass spectrometry results in terms of the fucosylation levels.

TABLE 8

| Possible Glycan Mass | 1298 | 1444 | 1460 | 1606 | 1623 | 1769 | 1509 | |
|---|---|---|---|---|---|---|---|---|
| Suggested Structure | | | | | | | Unknown | Fucosylation Level |
| Sample ID | G0 | G0f | G1 | G1f | G2 | G2f | | |
| CHO-S (WT) | | 30.10% | | 60.70% | | 9.20% | | 100% |

TABLE 8-continued

| Possible Glycan Mass | 1298 | 1444 | 1460 | 1606 | 1623 | 1769 | 1509 |
|---|---|---|---|---|---|---|---|
| ITL-LF2 | 49.80% | | 40.80% | | 5.10% | 4.30% | 0% |
| ITL-LF2 (3.5F/1) | 41.70% | 6.50% | 37.60% | 7.70% | 6.40% | | 14.20% |
| ITL-LF2 (3.5F/2) | 37.50% | 7.10% | 38.80% | 9.60% | 7.00% | | 16.70% |
| ITL-LF2 (3.5F/3) | 37.20% | 7.10% | 38.70% | 10.70% | 6.30% | | 17.80% |
| ITL-LF2 (3.5F/4) | 36.70% | 5.50% | 37.90% | 8.10% | 6.20% | 5.50% | 13.60% |
| ITL-LF2 (3.5F/5) | 38.20% | 6.50% | 39.70% | 9.00% | 6.50% | | 15.50% |

GluNac- ■ ; Mannose- ● ; Fucose- ▲ ; Galactose- ○

Conclusions and Discussion

Several approaches were developed recently in order to reduce the fucosylation levels of recombinant antibodies for obtaining enhanced ADCC. Development of the ITL-LF2 cell line from CHO-S cells was done successfully in this work by incubation of cells in the presence of methotrexate followed by an efficient selection of cells with the lowest fucose levels, i.e. zero fucose on the cells' membrane. Mutations and gene amplification created by incubation of cells in the presence of methotrexate (MTX) was previously described in the literature (Schimke 1988; Coquelle, Pipiras et al. 1997; Singer, Mesner et al. 2000).

Following MTX treatment, the mutagenic reagent was removed for the next selection steps. The selection was either done by isolation on magnetic beads (FIG. 7) and/or by FACS sorting (FIG. 12) using the fucose specific lectin aleuria aurantia lectin (AAL) which has high affinity towards the aFuc1-6GlcNA residue present on the Fc glycosylation site. Although the selection of the zero fucose expressing cells was done according to the fucose levels on the cells' membrane, zero fucose levels were found on the recombinant antibody (anti EGFR mAb) expressed in these cells, by a variety of analysis methods (FIGS. 34-43). The anti EGFR mAb which served as a model antibody presents two N glycosylation sites, one on the Fab fragment and the other which is important for the ADCC activity on the Fc CH2. The Octet and MS analyses were performed not only on the intact mAb but also on the Fc monomer with the ADCC relevant fucose residue. The results show zero fucose levels on the ADCC relevant fucose residue from material produced by the ITL-LF2 cells. The zero fucose phenotype of the ITL-LF2 cells was found to be stable for 370 PDLs tested (FIG. 15). Development of cells expressing recombinant proteins and production in bioreactors is usually completed within ~200 PDLs of the cells. The length of the zero fucose stability experiment (370 PDLs) is longer than that, so it is expected that the ITL-LF2 will remain stable for the entire clone development and production process. Most of the ITL-LF2 cell line characteristics were found to be similar to CHO-S as can be concluded from Table 8 herein below. Growth rate, maximum cell concentration, sialic acid level of cells' proteins and of recombinant antibody expressed in these cells and the expression level of anti EGFR mAb were very similar. In addition, ITL-LF2 cells were superior over CHO-S cells in viability and as a result in integral viable cell concentration (IVCC) determined in a batch process. This phenomenon could be a result of the stringent selection process that the cells went through along the sorting cycles for low fucose content on the cells' membrane.

Stable transfection was done with high efficiency to ITL-LF2 cells in the presence of exogenous fucose. Moreover, the recovery of ITL-LF2 cells from the transfection was faster than of CHO-S cells, although in the absence of exogenous fucose the transfected cells could hardly be recovered (data not shown). This finding implies that fucose has an important role in recovery from transfection and selection steps. Transient transfection with anti EGFR mAb was also successful with about 65-75% of the productivity obtained in CHO-S.

Table 9 herein below provides a summary of ITL-LF2 characteristics.

TABLE 9

| Characteristic | Result |
|---|---|
| Fucose level in the absence of fucose | Zero |
| Fucose level in the presence of fucose | Adjustable |
| Transfectability | Similar to CHO-S |
| Stability of Zero fucose phenotype | For at least 370 PDLs |
| Growth rate (PDT) | 15-20 hours, similar to CHO-S |
| Maximum cell concentration | $8.4 \times 10^6$ similar to CHO-S |
| Sialylation level | Similar to CHO-S |
| Transient expression | ~50% of the expression in CHO-S |
| Genetic modification | Modification of the mRNA profile of GMD |
| Stable expression | Similar to CHO-S |
| Viability in a batch process | High viability for a longer time than CHO-S |
| IVCC in a batch process | Higher IVCC than CHO-S cells in the pool stage |

Figure 20:
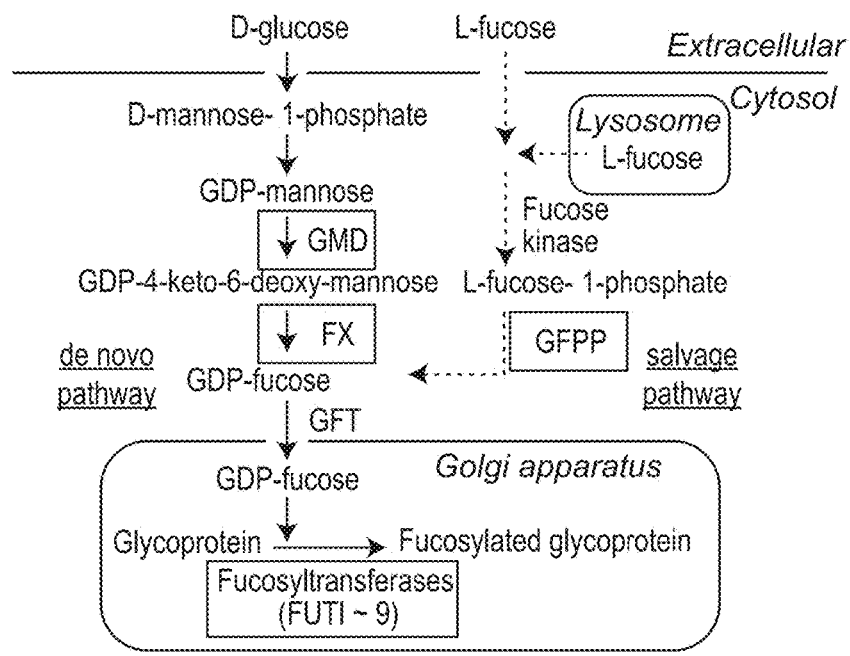
FIG. 20 is a diagram illustrating the protein fucosylation pathways and potential enzymes for mRNA Analysis (marked in squares).

Apart from the fact that the fucose level in ITL-LF2 cells was found to be zero and stable, the level of fucosylation on cells (FIG. 18 and FIG. 45) and recombinant protein (FIGS. 46-47 and 49) was found to be dependent on exogenous fucose addition in a dose dependant manner. Moreover, upon exogenous addition of a certain concentration of fucose, the resulted fucosylation level of a recombinant antibody in different samples was reproducible (FIG. 49 and Table 8). The fucosylation pathway (FIG. 20) shows that both the de novo and the salvage pathway branches could lead to generation of GDP-fucose. Since the ITL-LF2 were selected according to the zero fucose phenotype it was interesting to discover the genetic source for that characteristic. Addition of exogenous fucose resulted in regaining of fucosylation level of proteins on the cell's membrane (FIG. 18). This finding implied that the salvage pathway is active (FIG. 20).

RT-PCR and sequencing analyses of several key enzymes for the de novo and the salvage pathways showed that fucosyl transferase 8 (Fut8) mRNA in ITL-LF2 and CHO-S cells were identical in both size (FIG. 21) and sequence (data not shown). This finding differentiates the ITL-LF2 cells from Kyowa Hakko Kogyo Co., Ltd who disrupted both FUT8 alleles in a Chinese hamster ovary CHO DG44 cell line by sequential homologous recombination (Yamane-Ohnuki, Kinoshita et al. 2004; Kanda, Satoh et al. 2005).

Similarly to Fut8, the mRNA size and sequence of GDP-keo-6-deoxymannose 3,5-epimerase, 4-reductase (FX) (FIG. 21) involved in the de novo pathway was not changed in the ITL-LF2 cells. On the other hand the mRNA size of the GDP-mannose 4,6-dehydratase (GMD) in ITL-LF2 cells was shorter than in CHO-S (FIG. 20) and the sequence revealed two splice variants. The mRNA molecules extracted from the cells lacked either the third and fourth or the eighth and ninth exons (FIGS. 21A-B and FIGS. 22A-B. Differentiation between the deletions can not be detected from the gel, because the sizes of the deletions are similar (FIG. 21 and FIG. 23B). However, only the short GMD versions (and not the full length) could be detected on the gel (FIG. 21). The mechanism by which a sub population that was incubated with a mutagen expresses different splice variants and not the full length mRNA is not clear but it is probable that the alterations do not exist in the original CHO-S population as no low fucose cells were selected without MTX. These results are very interesting taking into account the selection was done phenotypically.

QPCR analysis showed that all the genes tested, that are involved in the fucosylation pathway, and express similar mRNA levels (FIG. 24). The results suggest that the zero fucose levels obtained in the ITL-LF2 cells is derived from either inactivity of the GMD protein expressed from the different splice variants, or from low levels or complete absence of the GMD protein.

A different phenotype selection approach was used by another research group for generation of lectin resistant mutants in CHO cells (Lec 13) (Ripka and Stanley 1986). In this approach the cells were incubated with toxic pea fucose specific lectin and the resistance cells were found to express human IgG1 that were deficient in fucose attached to the Asn(297)-linked carbohydrate (Shields, Lai et al. 2002). Further research work revealed that fucose levels in these cells increased after a relatively short time indicating that the low fucose phenotype was not stable and some active GDP-fucose protein was synthesized in the de novo pathway (Kanda, Yamane-Ohnuki et al. 2006). In another recent paper Kanda and co-workers (Kanda, Imai-Nishiya et al. 2007) showed by RT-PCR analysis that Lec 13 expresses mRNA at the same size as the mRNA expressed in CHO DG44. ITL-LF2 cells, as was indicated before, present a stable zero fucose phenotype probably due to a complete deficiency of the active GMD form (FIG. 21). Genotypic analysis of CHO-SM (Kanda, Imai-Nishiya et al. 2007) which is another lectin (*Lens culinaris* agglutinin-LCA) resistant cell line, by RT PCR sequencing and southern blot revealed that this cell line expresses mutated GMD mRNA that lacks exons 5, 6 and 7 encoding critical activity domains (Somoza, Menon et al. 2000; Webb, Mulichak et al. 2004). Exons 3 and 4 as well as exons 8 and 9 are also critical for the GMD activity as was demonstrated in ITL-LF2 cells. It is therefore concluded that ITL-LF2 cell's GMD profile is different from both Lec13 and CHO SM.

ITL-LF2 cells were generated following four successive sorting cycles by FACS selecting in each sort the lowest fucose (or absence of fucose) containing fraction of cells (Table 4). The first sort hardly even resulted in cells with low fucose phenotype. Nevertheless, after the second sort most of the cells expressed low fucose levels on the cell's membrane. Additional (third) sort ended with homogenous population that present only zero fucose levels. The fourth sort was done to ensure that only the zero fucose expressing cells are present (FIG. 12).

The ITL-LF2 cell line has been deposited at the Collection Nationale de Cultures de Microoganisms at the Pasteur Institute in Paris as deposit CNCM I-4449 on Feb. 28, 2011.

REFERENCES

ANOLIK, J. H., D. CAMPBELL, ET AL. (2003). "THE RELATIONSHIP OF FCGAMMARIIIA GENOTYPE TO DEGREE OF B CELL DEPLETION BY RITUXIMAB IN THE TREATMENT OF SYSTEMIC LUPUS ERYTHEMATOSUS." ARTHRITIS RHEUM 48(2): 455-9.

CARTER, P. J. (2006). "POTENT ANTIBODY THERAPEUTICS BY DESIGN." NAT REV IMMUNOL 6(5): 343-57.

CARTRON, G., L. DACHEUX, ET AL. (2002). "THERAPEUTIC ACTIVITY OF HUMANIZED ANTI-CD20 MONOCLONAL ANTIBODY AND POLYMORPHISM IN IGG FC RECEPTOR FCGAMMARIIIA GENE." BLOOD 99(3): 754-8.

CLARK, M. R. (1997). "IGG EFFECTOR MECHANISMS." CHEM IMMUNOL 65: 88-110.

COQUELLE, A., E. PIPIRAS, ET AL. (1997). "EXPRESSION OF FRAGILE SITES TRIGGERS INTRACHROMOSOMAL MAMMALIAN GENE AMPLIFICATION AND SETS BOUNDARIES TO EARLY AMPLICONS." CELL 89(2): 215-25.

COX, K. M., J. D. STERLING, ET AL. (2006). "GLYCAN OPTIMIZATION OF A HUMAN MONOCLONAL ANTIBODY IN THE AQUATIC PLANT LEMNA MINOR." NAT BIOTECHNOL 24(12): 1591-7.

CROWE, J. S., V. S. HALL, ET AL. (1992). "HUMANIZED MONOCLONAL ANTIBODY CAMPATH-1H: MYELOMA CELL EXPRESSION OF GENOMIC CONSTRUCTS, NUCLEOTIDE SEQUENCE OF CDNA CONSTRUCTS AND COMPARISON OF EFFECTOR MECHANISMS OF MYELOMA AND CHINESE HAMSTER OVARY CELL-DERIVED MATERIAL." CLIN EXP IMMUNOL 87(1): 105-10.

DALL'OZZO, S., S. TARTAS, ET AL. (2004). "RITUXIMAB-DEPENDENT CYTOTOXICITY BY NATURAL KILLER CELLS: INFLUENCE OF FCGR3A POLYMORPHISM ON THE CONCENTRATION-EFFECT RELATIONSHIP." CANCER RES 64(13): 4664-9.

GENNARI, R., S. MENARD, ET AL. (2004). "PILOT STUDY OF THE MECHANISM OF ACTION OF PREOPERATIVE TRASTUZUMAB IN PATIENTS WITH PRIMARY OPERABLE BREAST TUMORS OVEREXPRESSING HER2." CLIN CANCER RES 10(17): 5650-5.

HAMILTON, S. R., R. C. DAVIDSON, ET AL. (2006). "HUMANIZATION OF YEAST TO PRODUCE COMPLEX TERMINALLY SIALYLATED GLYCOPROTEINS." SCIENCE 313(5792): 1441-3.

IDUSOGIE, E. E., L. G. PRESTA, ET AL. (2000). "MAPPING OF THE CIQ BINDING SITE ON RITUXAN, A CHIMERIC ANTIBODY WITH A HUMAN IGG1 FC." J IMMUNOL 164(8): 4178-84.

IDUSOGIE, E. E., P. Y. WONG, ET AL. (2001). "ENGINEERED ANTIBODIES WITH INCREASED ACTIVITY TO RECRUIT COMPLEMENT." J IMMUNOL 166(4): 2571-5.

IIDA, S., R. KUNI-KAMOCHI, ET AL. (2009). "TWO MECHANISMS OF THE ENHANCED ANTIBODY-DEPENDENT CELLULAR CYTOTOXICITY (ADCC) EFFICACY OF NON-FUCOSYLATED THERAPEUTIC ANTIBODIES 1N HUMAN BLOOD." BMC CANCER 9: 58.

IMAI-NISHIYA, H., K. MOR1, ET AL. (2007). "DOUBLE KNOCKDOWN OF ALPHA1,6-FUCOSYLTRANSFERASE (FUT8) AND GDP-MANNOSE 4,6-DEHYDRATASE (GMD) IN ANTIBODY-PRODUCING CELLS: A NEW STRATEGY FOR GENERATING FULLY NON-FUCOSYLATED THERAPEUTIC ANTIBODIES WITH ENHANCED ADCC." BMC BIOTECHNOL 7: 84.

JEFFERIS, R. (2005). "GLYCOSYLATION OF RECOMBINANT ANTIBODY THERAPEUTICS." BIOTECHNOL PROG 21(1): 11-6.

JEFFERIS, R. (2007). "ANTIBODY THERAPEUTICS: ISOTYPE AND GLYCOFORM SELECTION." EXPERT OPIN BIOL THER 7(9): 1401-13.

JEFFERIS, R. (2009). "RECOMBINANT ANTIBODY THERAPEUTICS: THE IMPACT OF GLYCOSYLATION ON MECHANISMS OF ACTION." TRENDS PHARMACOL SCI 30(7): 356-62.

KANDA, Y., H. IMAI-NISHIYA, ET AL. (2007). "ESTABLISHMENT OF A GDP-MANNOSE 4,6-DEHYDRATASE (GMD) KNOCKOUT HOST CELL LINE: A NEW STRATEGY FOR GENERATING COMPLETELY NON-FUCOSYLATED RECOMBINANT THERAPEUTICS." J BIOTECHNOL 130(3): 300-10.

KANDA, Y., M. SATOH, ET AL. (2005). CELLS PRODUCING ANTIBODY COMPOSITIONS WITH INCREASED ANTIBODY DEPENDENT CELLULAR CYTOTOXIC ACTIVITY. TOKYO, KYOWA HAKKO KOGYO CO., LTD.

KANDA, Y., N. YAMANE-OHNUKI, ET AL. (2006). "COMPARISON OF CELL LINES FOR STABLE PRODUCTION OF FUCOSE-NEGATIVE ANTIBODIES WITH ENHANCED ADCC." BIOTECHNOL BIOENG 94(4): 680-8.

LAZAR, G. A., W. DANG, ET AL. (2006). "ENGINEERED ANTIBODY FC VARIANTS WITH ENHANCED EFFECTOR FUNCTION." PROC NATL ACAD SCI USA 103(11): 4005-10.

LOUIS, E., Z. EL GHOUL, ET AL. (2004). "ASSOCIATION BETWEEN POLYMORPHISM IN IGG FC RECEPTOR IIIA CODING GENE AND BIOLOGICAL RESPONSE TO INFLIXIMAB IN CROHN'S DISEASE." ALIMENT PHARMACOL THER 19(5): 511-9.

MIESCHER, S., M. O. SPYCHER, ET AL. (2004). "A SINGLE RECOMBINANT ANTI-RHD IGG PREVENTS RHD IMMUNIZATION: ASSOCIATION OF RHD-POSITIVE RED BLOOD CELL CLEARANCE RATE WITH POLYMORPHISMS IN THE FCGAMMARIIA AND FCGAMMAIIIA GENES." BLOOD 103(11): 4028-35.

MORGAN, A., N. D. JONES, ET AL. (1995). "THE N-TERMINAL END OF THE CH2 DOMAIN OF CHIMERIC HUMAN IGG1 ANTI-HLA-DR IS NECESSARY FOR C1Q, FC GAMMA RI AND FC GAMMA RIII BINDING." IMMUNOLOGY 86(2): 319-24.

MOUTEL, S. AND F. PEREZ (2008). ""ANTIBODIES—EUROPE. ENGINEERING THE NEXT GENERATION OF ANTIBODIES"." BIOTECHNOL J 3(3): 298-300.

NECHANSKY, A., M. SCHUSTER, ET AL. (2007). "COMPENSATION OF ENDOGENOUS IGG MEDIATED INHIBITION OF ANTIBODY-DEPENDENT CELLULAR CYTOTOXICITY BY GLYCO-ENGINEERING OF THERAPEUTIC ANTIBODIES." MOL IMMUNOL 44(7): 1815-7.

NEZLIN, R. AND V. GHETIE (2004). "INTERACTIONS OF IMMUNOGLOBULINS OUTSIDE THE ANTIGEN-COMBINING SITE." ADV IMMUNOL 82: 155-215.

OGANESYAN, V., M. M. DAMSCHRODER, ET AL. (2008). "STRUCTURAL CHARACTERIZATION OF A MUTATED, ADCC-ENHANCED HUMAN FC FRAGMENT." MOL IMMUNOL 45(7): 1872-82.

OHYAMA, C., P. L. SMITH, ET AL. (1998). "MOLECULAR CLONING AND EXPRESSION OF GDP-D-MANNOSE-4,6-DEHYDRATASE, A KEY ENZYME FOR FUCOSE METABOLISM DEFECTIVE IN LEC13 CELLS." J BIOL CHEM 273(23): 14582-7.

PRESTA, L. G. (2008). "MOLECULAR ENGINEERING AND DESIGN OF THERAPEUTIC ANTIBODIES." CURR OPIN IMMUNOL 20(4): 460-70.

RAJU, T. S. (2008). "TERMINAL SUGARS OF FC GLYCANS INFLUENCE ANTIBODY EFFECTOR FUNCTIONS OF IGGS." CURR OPIN IMMUNOL 20(4): 471-8.

REICHERT, J. M. AND V. E. VALGE-ARCHER (2007). "DEVELOPMENT TRENDS FOR MONOCLONAL ANTIBODY CANCER THERAPEUTICS." NAT REV DRUG DISCOV 6(5): 349-56.

RIPKA, J. AND P. STANLEY (1986). "LECTIN-RESISTANT CHO CELLS: SELECTION OF FOUR NEW PEA LECTIN-RESISTANT PHENOTYPES." SOMAT CELL MOL GENET 12(1): 51-62.

ROOPENIAN, D. C. AND S. AKILESH (2007). "FCRN: THE NEONATAL FC RECEPTOR COMES OF AGE." NAT REV IMMUNOL 7(9): 715-25.

SALFELD, J. G. (2007). "ISOTYPE SELECTION IN ANTIBODY ENGINEERING." NAT BIOTECHNOL 25(12): 1369-72.

SCHIMKE, R. T. (1988). "GENE AMPLIFICATION IN CULTURED CELLS." J BIOL CHEM 263(13): 5989-92.

SHIELDS, R. L., J. LAI, ET AL. (2002). "LACK OF FUCOSE ON HUMAN IGG1 N-LINKED OLIGOSACCHARIDE IMPROVES BINDING TO HUMAN FCGAMMA RIII AND ANTIBODY-DEPENDENT CELLULAR TOXICITY." J BIOL CHEM 277(30): 26733-40.

SHINKAWA, T., K. NAKAMURA, ET AL. (2003). "THE ABSENCE OF FUCOSE BUT NOT THE PRESENCE OF GALACTOSE OR BISECTING N-ACETYLGLUCOSAMINE OF HUMAN IGGI COMPLEX-TYPE OLIGOSACCHARIDES SHOWS THE CRITICAL ROLE OF ENHANCING ANTIBODY-DEPENDENT CELLULAR CYTOTOXICITY." J BIOL CHEM 278(5): 3466-73.

SINGER, M. J., L. D. MESNER, ET AL. (2000). "AMPLIFICATION OF THE HUMAN DIHYDROFOLATE REDUCTASE GENE VIA DOUBLE MINUTES IS INITIATED BY CHROMOSOME BREAKS." PROC NATL ACAD SCI USA 97(14): 7921-6.

SOMOZA, J. R., S. MENON, ET AL. (2000). "STRUCTURAL AND KINETIC ANALYSIS OF ESCHERICHIA COLI GDP-MANNOSE 4,6 DEHYDRATASE PROVIDES INSIGHTS INTO THE ENZYME'S CATA-

LYTIC MECHANISM AND REGULATION BY GDP-FUCOSE." STRUCTURE 8(2): 123-35.

STROHL, W. R. (2009). "OPTIMIZATION OF FC-MEDIATED EFFECTOR FUNCTIONS OF MONOCLONAL ANTIBODIES." CURR OPIN BIOTECHNOL 20(6): 685-91.

STROHL, W. R. (2009). THERAPEUTIC MONOCLONAL ANTIBODIES—PAST, PRESENT AND FUTURE. THERAPEUTIC MONOCLONAL ANTIBODIES: FROM BENCH TO CLINIC. A. Z. N. Y. J. W. SONS: 4-50.

SULLIVAN, F. X., R. KUMAR, ET AL. (1998). "MOLECULAR CLONING OF HUMAN GDP-MANNOSE 4,6-DEHYDRATASE AND RECONSTITUTION OF GDP-FUCOSE BIOSYNTHESIS IN VITRO." J BIOL CHEM 273(14): 8193-202.

TREON, S. P., M. HANSEN, ET AL. (2005). "POLYMORPHISMS IN FCGAMMARIIIA (CD16) RECEPTOR EXPRESSION ARE ASSOCIATED WITH CLINICAL RESPONSE TO RITUXIMAB IN WALDENSTROM'S MACROGLOBULINEMIA." J CLIN ONCOL 23(3): 474-81.

UMANA, P., J. JEAN-MAIRET, ET AL. (1999). "ENGINEERED GLYCOFORMS OF AN ANTINEUROBLASTOMA IGG1 WITH OPTIMIZED ANTIBODY-DEPENDENT CELLULAR CYTOTOXIC ACTIVITY." NAT BIOTECHNOL 17(2): 176-80.

VON HORSTEN, H. H., C. OGOREK, ET AL. "PRODUCTION OF NON-FUCOSYLATED ANTIBODIES BY CO-EXPRESSION OF HETEROLOGOUS GDP-6-DEOXY-D-LYXO-4-HEXULOSE REDUCTASE." GLYCOBIOLOGY 20(12): 1607-18.

WEBB, N. A., A. M. MULICHAK, ET AL. (2004). "CRYSTAL STRUCTURE OF A TETRAMERIC GDP-D-MANNOSE 4,6-DEHYDRATASE FROM A BACTERIAL GDP-D-RHAMNOSE BIOSYNTHETIC PATHWAY." PROTEIN SCI 13(2): 529-39.

WENG, W. K. AND R. LEVY (2003). "TWO IMMUNOGLOBULIN G FRAGMENT C RECEPTOR POLYMORPHISMS INDEPENDENTLY PREDICT RESPONSE TO RITUXIMAB IN PATIENTS WITH FOLLICULAR LYMPHOMA." J CLIN ONCOL 21(21): 3940-7.

YAMANE-OHNUKI, N., S. KINOSHITA, ET AL. (2004). "ESTABLISHMENT OF FUT8 KNOCKOUT CHINESE HAMSTER OVARY CELLS: AN IDEAL HOST CELL LINE FOR PRODUCING COMPLETELY DEFUCOSYLATED ANTIBODIES WITH ENHANCED ANTIBODY-DEPENDENT CELLULAR CYTOTOXICITY." BIOTECHNOL BIOENG 87(5): 614-22.

---

What is claimed is:

1. A method of selecting a Chinese hamster ovary (CHO) cell having a zero fucose level useful as a host cell for expressing a recombinant protein, the method comprising:
   (a) introducing a genetic mutation into a coding region for a GDP-mannose 4,6-dehydratase (GMD) in a CHO cell of a population of CHO cells by contacting the cells with methotrexate (MTX), thereby generating a CHO cell with a mutated GMD protein,
   (b) contacting the population of CHO cells comprising at least one CHO cell with a mutated GMD protein with a non-toxic fucose binding agent for an amount of time that allows binding of the fucose binding agent to a fucose moiety on a cell membrane of one or more cells of the population of cells, wherein the amount of time does not allow killing of the cells; and
   (c) depleting from the population of cells comprising mutated cells, a subpopulation of one or more cells which bind the fucose binding agent, thereby selecting cells useful as host cells for expressing recombinant proteins, the selected cells having zero fucose content in the absence of external fucose, wherein the expressed mutated GMD protein lacks amino acids encoded by exons 3 and 4 or lacks amino acids encoded by exons 8 and 9, and further wherein the cells exhibit a stable fucose phenotype for more than 100 population doublings.

2. The method of claim 1, wherein the CHO cells are selected from CHO-K1, CHO-S, DUXB11, CHO-1E5, CHO3F, CHO/DG44 and CHO-2.6.

3. The method of claim 1, wherein the recombinant protein is an antibody or a Fc protein.

4. The method of claim 1, wherein said fucose binding agent is attached to a detectable moiety or an affinity moiety.

5. The method of claim 1, wherein said population of CHO cells comprising mutated cells is in contact with the non-toxic fucose binding agent for an amount of time that is no longer than 60 minutes.

6. The method of claim 4, wherein when said fucose binding agent is attached to an affinity moiety, the method further comprises contacting said mutated population of cells with an additional agent, such additional agent comprising a cognate binding moiety for said affinity moiety.

7. The method of claim 4, wherein said affinity moiety comprises biotin.

8. The method of claim 6, wherein said cognate binding moiety is attached to a detectable moiety.

9. The method of claim 8, wherein said detectable moiety comprises a fluorescent moiety or a magnetic moiety.

10. The method of claim 1, wherein said depleting is effected by FACS sorting.

11. The method of claim 1, wherein said depleting is effected by magnetic separation.

12. The method of claim 1, wherein said depleting is effected by at least three rounds of sequential depleting.

13. The method of claim 1, wherein said fucose binding agent is aleuria aurantia lectin (AAL) or *Aspergillus oryzae* 1-fucose-specific lectin (AOL).

14. An isolated CHO cell comprising an expressed mutated GDP-mannose 4,6-dehydratase (GMD), wherein the cell has a zero fucose content in the absence of external fucose, and wherein the expressed mutated GMD lacks amino acids encoded by exons 3 and 4 or lacks amino acids encoded by exons 8 and 9, and further wherein the cell exhibits a stable fucose phenotype for more than 100 population doublings.

15. The isolated CHO cell of claim 14 wherein the cell is genetically modified to express a mutated GDP-mannose 4,6-dehydratase (GMD) having an amino acid sequence as set forth in SEQ ID NO: 23 or 24.

16. The isolated CHO cell of claim 14 wherein the cell is genetically modified such that an amount of fucosylation of a protein expressed therein is linearly dependent on a concentration of external fucose.

17. The isolated CHO cell of claim 14, having a 20% higher integral viable cell concentration (IVCC) than non-mutated CHO cells.

18. The isolated CHO cell of claim 14, expressing a wild-type fucosyl transferase-8 (Fut8).

19. The isolated CHO cell of claim 14, expressing a wild-type GDP-keto-6-deoxymannose 3, 5-epimerase, 4-reductase (FX).

20. The isolated CHO cell of claim 14, having a population doubling time of no more than 20 hours.

21. The isolated CHO cell of claim 14, expressing a recombinant antibody or Fc fusion protein of interest.

22. A CHO cell line comprising the isolated cell of claim 14.

23. The isolated CHO cell of claim 21, deposited under CNCM Accession Number I-4449.

24. A cell culture which comprises the isolated CHO cell of claim 14 and a cell culture medium being devoid of animal-derived contaminants.

25. The cell culture of claim 24, wherein said cell culture medium comprises fucose.

26. The cell culture of claim 24, wherein said cell culture medium is devoid of fucose.

27. A method for the production of a recombinant protein comprising transfecting the selected CHO cell of claim 1 with a polynucleotide comprising a nucleic acid sequence which encodes the recombinant protein, culturing the transfected CHO cell under conditions suitable for expression of the recombinant protein, and isolating the protein.

28. The method of claim 27, wherein the recombinant protein is an antibody or a Fc fusion protein.

29. The method of claim 27, wherein said transfecting is effected in the presence of exogenous fucose.

30. The method of claim 27, further comprising culturing the selected CHO cell in a culture medium comprising fucose following said transfecting.

31. The isolated CHO cell of claim 14, wherein the mutated GMD lacks amino acids encoded by exons 3, 4, 8 and 9.

32. The isolated CHO cell of claim 14 wherein the mutated GDP-mannose 4,6-dehydratase (GMD) has the amino acid sequence set forth in SEQ ID NO: 25 at positions 1-49, 151-257, and 330-372.

* * * * *

UNITED STATES PATENT AND TRADEMARK OFFICE
CERTIFICATE OF CORRECTION

PATENT NO. : 9,574,003 B2
APPLICATION NO. : 14/003767
DATED : February 21, 2017
INVENTOR(S) : Daniel Helman et al.

Page 1 of 1

It is certified that error appears in the above-identified patent and that said Letters Patent is hereby corrected as shown below:

On the Title Page

At item (75), Line 2, "Barshimon," should be -- Bar-shimon, --.

In the Claims

At Column 85, Line 54, "protein," should be -- protein; --.

At Column 87, Line 13, "1-fucose-specific" should be -- l-fucose-specific --.

At Column 88, Line 5, "cell" should be -- CHO cell --.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 46

<210> SEQ ID NO 1
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 1
gtctgaattc aagcttgtag cgatcgccgc caccat                        36

<210> SEQ ID NO 2
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 2
ggatccgcgg ccgctacgcc gccctcagat ctttatca                      38

<210> SEQ ID NO 3
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 3
gcttgaattc aagcttctag tacgcgtgtt taaacc                        36

<210> SEQ ID NO 4
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 4
```

```
gcggccgctg tccgcgcctt actaacactc tc                                    32

<210> SEQ ID NO 5
<211> LENGTH: 18
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 5' FAM conjugated oligonucleotide
<220> FEATURE:
<221> NAME/KEY: misc_feature
<223> OTHER INFORMATION: 3' BQ conjugated oligonucleotide

<400> SEQUENCE: 5
atggctgagt ctctccga                                                    18

<210> SEQ ID NO 6
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 6
ctggagcgct taaaacaaca aa                                               22

<210> SEQ ID NO 7
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 7
ctgatcaata gggccttctg gta                                              23

<210> SEQ ID NO 8
<211> LENGTH: 18
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 5' FAM conjugated oligonucleotide
<220> FEATURE:
<221> NAME/KEY: misc_feature
<223> OTHER INFORMATION: 3' BQ conjugated oligonucleotide

<400> SEQUENCE: 8
caaagatgca gatctgac                                                    18

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
gcttacccgg agaggaatgg                                                  20

<210> SEQ ID NO 10
<211> LENGTH: 20
<212> TYPE: DNA
```

```
<213> ORGANISM: Artificial sequence
<220> FEATURE:
<223> OTHER INFORMATION: Single strand DNA oligonucleotide

<400> SEQUENCE: 10
gaacagggct tgggtttgtg                                                20

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 5' FAM conjugated oligonucleotide
<220> FEATURE:
<221> NAME/KEY: misc_feature
<223> OTHER INFORMATION: 3' BQ conjugated oligonucleotide

<400> SEQUENCE: 11
ctttgactta gcagagtaca                                                20

<210> SEQ ID NO 12
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 12
gccctatgga gcagccaaa                                                 19

<210> SEQ ID NO 13
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 13
aatgccgttc accgcaaa                                                  18

<210> SEQ ID NO 14
<211> LENGTH: 19
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 5' FAM conjugated oligonucleotide
<220> FEATURE:
<221> NAME/KEY: misc_feature
<223> OTHER INFORMATION: 3' BQ conjugated oligonucleotide

<400> SEQUENCE: 14
cctgaatgtt gttgtcctt                                                 19

<210> SEQ ID NO 15
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 15
tccacctcct caagggaaca c                                              21
```

```
<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 16
ctcctccgtt gttccaatgt g                                      21

<210> SEQ ID NO 17
<211> LENGTH: 18
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 5' FAM conjugated oligonucleotide
<220> FEATURE:
<221> NAME/KEY: misc_feature
<223> OTHER INFORMATION: 3' BQ conjugated oligonucleotide

<400> SEQUENCE: 17
ttctatgccc tgctcaca                                          18

<210> SEQ ID NO 18
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 18
ctgctgctca aacagaccac tt                                     22

<210> SEQ ID NO 19
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 19
gtgccctcag ctccctctt                                         19

<210> SEQ ID NO 20
<211> LENGTH: 17
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 5' FAM conjugated oligonucleotide
<220> FEATURE:
<221> NAME/KEY: misc_feature
<223> OTHER INFORMATION: 3' BQ conjugated oligonucleotide

<400> SEQUENCE: 20
ttgggacgtc tcactgc                                           17

<210> SEQ ID NO 21
<211> LENGTH: 20
<212> TYPE: DNA
<213> ORGANISM: Artificial sequence
<220> FEATURE:
```

<223> OTHER INFORMATION: Single strand DNA oligonucleotide

<400> SEQUENCE: 21
ctgctccctg gcaactccta                                                    20

<210> SEQ ID NO 22
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 22
aagtgggaag cataatgagc aaa                                                23

<210> SEQ ID NO 23
<211> LENGTH: 300
<212> TYPE: PRT
<213> ORGANISM: Cricetulus griseus
<220> FEATURE:
<221> NAME/KEY: misc_feature
<223> OTHER INFORMATION: GDP-mannose 4,6-dehydratase (GMD) - Splice
      variant 1

<400> SEQUENCE: 23

```
Met Ala His Ala Pro Ala Ser Cys Pro Ser Ser Arg Asn Ser Gly Asp
1               5                   10                  15

Gly Asp Lys Gly Lys Pro Arg Lys Val Ala Leu Ile Thr Gly Ile Thr
            20                  25                  30

Gly Gln Asp Gly Ser Tyr Leu Ala Glu Phe Leu Leu Glu Lys Gly Tyr
        35                  40                  45

Glu Val His Gly Ile Val Arg Arg Ser Ser Ser Phe Asn Thr Gly Arg
    50                  55                  60

Ile Glu His Leu Tyr Lys Asn Pro Gln Ala His Ile Glu Gly Asn Met
65                  70                  75                  80

Lys Leu His Tyr Gly Asp Leu Thr Asp Ser Thr Cys Leu Val Lys Ile
                85                  90                  95

Ile Asn Glu Val Lys Pro Thr Glu Ile Tyr Asn Leu Gly Ala Gln Ser
            100                 105                 110

His Val Lys Ile Ser Phe Asp Leu Ala Glu Tyr Thr Ala Asp Val Asp
        115                 120                 125

Gly Val Gly Thr Leu Arg Leu Leu Asp Ala Ile Lys Thr Cys Gly Leu
    130                 135                 140

Ile Asn Ser Val Lys Phe Tyr Gln Ala Ser Thr Ser Glu Leu Tyr Gly
145                 150                 155                 160

Lys Val Gln Glu Ile Pro Gln Lys Glu Thr Thr Pro Phe Tyr Pro Arg
                165                 170                 175

Ser Pro Tyr Gly Ala Ala Lys Leu Tyr Ala Tyr Trp Ile Val Val Asn
            180                 185                 190

Phe Arg Glu Ala Tyr Asn Leu Phe Ala Val Asn Gly Ile Leu Phe Asn
        195                 200                 205

His Glu Ser Pro Arg Arg Gly Ala Asn Phe Val Thr Arg Lys Ile Ser
    210                 215                 220

Arg Ser Val Ala Lys Ile Tyr Leu Gly Gln Leu Glu Cys Phe Ser Leu
225                 230                 235                 240

Gly Asn Leu Asp Ala Lys Arg Asp Trp Gly His Ala Lys Asp Tyr Val
                245                 250                 255

Glu Asp Phe Leu Gln Gly Asp Cys Ser Lys Ala Gln Gln Lys Leu Asn
```

```
                260                 265                 270
Trp Lys Pro Arg Val Ala Phe Asp Glu Leu Val Arg Glu Met Val Gln
        275                 280                 285
Ala Asp Val Glu Leu Met Arg Thr Asn Pro Asn Ala
    290                 295                 300

<210> SEQ ID NO 24
<211> LENGTH: 306
<212> TYPE: PRT
<213> ORGANISM: Cricetulus griseus
<220> FEATURE:
<221> NAME/KEY: misc_feature
<223> OTHER INFORMATION: GDP-mannose 4,6-dehydratase (GMD) - Splice
      variant 2

<400> SEQUENCE: 24

Met Ala His Ala Pro Ala Ser Cys Pro Ser Arg Asn Ser Gly Asp
1               5                   10                  15

Gly Asp Lys Gly Lys Pro Arg Lys Val Ala Leu Ile Thr Gly Ile Thr
            20                  25                  30

Gly Gln Asp Gly Ser Tyr Leu Ala Glu Phe Leu Leu Glu Lys Gly Tyr
        35                  40                  45

Glu Ile Ser Phe Asp Leu Ala Glu Tyr Thr Ala Asp Val Asp Gly Val
50                  55                  60

Gly Thr Leu Arg Leu Leu Asp Ala Ile Lys Thr Cys Gly Leu Ile Asn
65                  70                  75                  80

Ser Val Lys Phe Tyr Gln Ala Ser Thr Ser Glu Leu Tyr Gly Lys Val
                85                  90                  95

Gln Glu Ile Pro Gln Lys Glu Thr Thr Pro Phe Tyr Pro Arg Ser Pro
            100                 105                 110

Tyr Gly Ala Ala Lys Leu Tyr Ala Tyr Trp Ile Val Val Asn Phe Arg
        115                 120                 125

Glu Ala Tyr Asn Leu Phe Ala Val Asn Gly Ile Leu Phe Asn His Glu
130                 135                 140

Ser Pro Arg Arg Gly Ala Asn Phe Val Thr Arg Lys Ile Ser Arg Ser
145                 150                 155                 160

Val Ala Lys Ile Tyr Leu Gly Gln Leu Glu Cys Phe Ser Leu Gly Asn
                165                 170                 175

Leu Asp Ala Lys Arg Asp Trp Gly His Ala Lys Asp Tyr Val Glu Ala
            180                 185                 190

Met Trp Leu Met Leu Gln Asn Asp Glu Pro Glu Asp Phe Val Ile Ala
        195                 200                 205

Thr Gly Glu Val His Ser Val Arg Glu Phe Val Glu Lys Ser Phe Met
210                 215                 220

His Ile Gly Lys Thr Ile Val Trp Glu Gly Lys Asn Glu Asn Glu Val
225                 230                 235                 240

Gly Arg Cys Lys Glu Thr Gly Lys Ile His Val Thr Val Asp Leu Lys
                245                 250                 255

Tyr Tyr Arg Pro Thr Glu Val Asp Phe Leu Gln Gly Asp Cys Ser Lys
            260                 265                 270

Ala Gln Gln Lys Leu Asn Trp Lys Pro Arg Val Ala Phe Asp Glu Leu
        275                 280                 285

Val Arg Glu Met Val Gln Ala Asp Val Glu Leu Met Arg Thr Asn Pro
290                 295                 300

Asn Ala
305
```

```
<210> SEQ ID NO 25
<211> LENGTH: 372
<212> TYPE: PRT
<213> ORGANISM: Cricetulus griseus
<220> FEATURE:
<221> NAME/KEY: misc_feature
<223> OTHER INFORMATION: GDP-mannose 4,6-dehydratase (GMD Full length)

<400> SEQUENCE: 25

Met Ala His Ala Pro Ala Ser Cys Pro Ser Ser Arg Asn Ser Gly Asp
1               5                   10                  15

Gly Asp Lys Gly Lys Pro Arg Lys Val Ala Leu Ile Thr Gly Ile Thr
            20                  25                  30

Gly Gln Asp Gly Ser Tyr Leu Ala Glu Phe Leu Leu Glu Lys Gly Tyr
        35                  40                  45

Glu Val His Gly Ile Val Arg Arg Ser Ser Ser Phe Asn Thr Gly Arg
    50                  55                  60

Ile Glu His Leu Tyr Lys Asn Pro Gln Ala His Ile Glu Gly Asn Met
65                  70                  75                  80

Lys Leu His Tyr Gly Asp Leu Thr Asp Ser Thr Cys Leu Val Lys Ile
                85                  90                  95

Ile Asn Glu Val Lys Pro Thr Glu Ile Tyr Asn Leu Gly Ala Gln Ser
            100                 105                 110

His Val Lys Ile Ser Phe Asp Leu Ala Glu Tyr Thr Ala Asp Val Asp
        115                 120                 125

Gly Val Gly Thr Leu Arg Leu Leu Asp Ala Ile Lys Thr Cys Gly Leu
    130                 135                 140

Ile Asn Ser Val Lys Phe Tyr Gln Ala Ser Thr Ser Glu Leu Tyr Gly
145                 150                 155                 160

Lys Val Gln Glu Ile Pro Gln Lys Glu Thr Thr Pro Phe Tyr Pro Arg
                165                 170                 175

Ser Pro Tyr Gly Ala Ala Lys Leu Tyr Ala Tyr Trp Ile Val Val Asn
            180                 185                 190

Phe Arg Glu Ala Tyr Asn Leu Phe Ala Val Asn Gly Ile Leu Phe Asn
        195                 200                 205

His Glu Ser Pro Arg Arg Gly Ala Asn Phe Val Thr Arg Lys Ile Ser
    210                 215                 220

Arg Ser Val Ala Lys Ile Tyr Leu Gly Gln Leu Glu Cys Phe Ser Leu
225                 230                 235                 240

Gly Asn Leu Asp Ala Lys Arg Asp Trp Gly His Ala Lys Asp Tyr Val
                245                 250                 255

Glu Ala Met Trp Leu Met Leu Gln Asn Asp Glu Pro Glu Asp Phe Val
            260                 265                 270

Ile Ala Thr Gly Glu Val His Ser Val Arg Glu Phe Val Glu Lys Ser
        275                 280                 285

Phe Met His Ile Gly Lys Thr Ile Val Trp Glu Gly Lys Asn Glu Asn
    290                 295                 300

Glu Val Gly Arg Cys Lys Glu Thr Gly Lys Ile His Val Thr Val Asp
305                 310                 315                 320

Leu Lys Tyr Tyr Arg Pro Thr Glu Val Asp Phe Leu Gln Gly Asp Cys
                325                 330                 335

Ser Lys Ala Gln Gln Lys Leu Asn Trp Lys Pro Arg Val Ala Phe Asp
            340                 345                 350

Glu Leu Val Arg Glu Met Val Gln Ala Asp Val Glu Leu Met Arg Thr
```

```
            355                 360                 365
Asn Pro Asn Ala
    370

<210> SEQ ID NO 26
<211> LENGTH: 903
<212> TYPE: DNA
<213> ORGANISM: Cricetulus griseus
<220> FEATURE:
<221> NAME/KEY: misc_feature
<223> OTHER INFORMATION: GDP-mannose 4,6-dehydratase (GMD) - Splice
      variant 1

<400> SEQUENCE: 26
atggctcacg ctcccgctag ctgcccgagc tccaggaact ctggggacgg cgataagggc      60
aagcccagga aggtggcgct catcacgggc atcaccggcc aggatggctc atacttggca     120
gaattcctgc tggagaaagg atacgaggtt catggaattg tacggcgatc cagttcattt     180
aatacaggtc gaattgaaca tttatataag aatccacagg ctcatattga aggaaacatg     240
aagttgcact atggtgacct caccgacagc acctgcctag taaaaatcat caatgaagtc     300
aaacctacag atctacaa tcttggtgcc cagagccatg tcaagatttc ctttgactta     360
gcagagtaca ctgcagatgt tgatggagtt ggcaccttgc ggcttctgga tgcaattaag     420
acttgtggcc ttataaattc tgtgaagttc taccaggcct caactagtga actgtatgga     480
aaagtgcaag aaatacccca aaagagacc accccttct atccaaggtc gccctatgga     540
gcagccaaac tttatgccta ttggattgta gtgaactttc gagagctta taatctcttt     600 gcggtgaacg gcattctctt caatcatgag agtcctagaa gaggagctaa ttttgttact     660
cgaaaaatta gccggtcagt agctaagatt taccttggac aactggaatg tttcagtttg     720
ggaaatctgg acgccaaacg agactggggc catgccaagg actatgtcga ggacttcctg     780
cagggagact gctccaaggc gcagcagaaa ctgaactgga agcccgcgt tgcctttgac     840 gagctggtga gggagatggt gcaagccgat gtggagctca tgagaaccaa ccccaacgcc     900
tga                                                                  903

<210> SEQ ID NO 27
<211> LENGTH: 921
<212> TYPE: DNA
<213> ORGANISM: Cricetulus griseus
<220> FEATURE:
<221> NAME/KEY: misc_feature
<223> OTHER INFORMATION: GDP-mannose 4,6-dehydratase (GMD) - Splice
      variant 2

<400> SEQUENCE: 27
atggctcacg ctcccgctag ctgcccgagc tccaggaact ctggggacgg cgataagggc      60
aagcccagga aggtggcgct catcacgggc atcaccggcc aggatggctc atacttggca     120
gaattcctgc tggagaaagg atacgagatt cctttgact tagcagagta cactgcagat     180
gttgatggag ttggcaccct tgcggcttctg gatgcaatta agacttgtgg ccttataaat     240
tctgtgaagt tctaccaggc ctcaactagt gaactgtatg gaaaagtgca agaaataccc     300
cagaaagaga ccaccccttt ctatccaagg tcgccctatg gagcagccaa actttatgcc     360
tattggattg tagtgaactt tcgagaggct tataatctct ttgcggtgaa cggcattctc     420
ttcaatcatg agagtcctag aagaggagct aattttgtta ctcgaaaaat tagccggtca     480
gtagctaaga tttaccttgg acaactggaa tgtttcagtt tgggaaatct ggacgccaaa     540
```

```
cgagactggg gccatgccaa ggactatgtc gaggctatgt ggctgatgtt acaaaatgat      600
gaaccagagg actttgtcat agctactggg gaagttcata gtgtccgtga atttgttgag      660
aaatcattca tgcacattgg aaagaccatt gtgtgggaag aaagaatga aaatgaagtg       720 ggcagatgta aagagaccgg caaaattcat gtgactgtgg atctgaaata ctaccgacca      780
actgaagtgg acttcctgca gggagactgc tccaaggcgc agcagaaact gaactggaag      840
ccccgcgttg cctttgacga gctggtgagg gagatggtgc aagccgatgt ggagctcatg      900
agaaccaacc ccaacgcctg a                                                921
```

<210> SEQ ID NO 28
<211> LENGTH: 1120
<212> TYPE: DNA
<213> ORGANISM: Cricetulus griseus
<220> FEATURE:
<221> NAME/KEY: misc_feature
<223> OTHER INFORMATION: GDP-mannose 4,6-dehydratase (GMD Full length)

<400> SEQUENCE: 28

```
atggctcacg ctcccgctag ctgcccgagc tccaggaact ctggggacgg cgataagggc       60
aagcccagga aggtggcgct catcacgggc atcaccggcc aggatggctc atacttggca      120
gaattcctgc tggagaaagg atacgaggtt catggaattg tacggcgatc cagttcattt      180
aatacaggtc gaattgaaca tttatataag aatccacagg ctcatattga aggaaacatg      240
aagttgcact atggtgacct caccgacagc acctgcctag taaaaatcat caatgaagtc      300
aaacctacag atctacaa tcttggtgcc cagagccatg tcaagatttc ctttgactta       360
gcagagtaca ctgcagatgt tgatggagtt ggcaccttgc ggcttctgga tgcaattaag      420
acttgtggcc ttataaattc tgtgaagttc taccaggcct caactagtga actgtatgga      480
aaagtgcaag aaataccca gaaagagacc accccttct atccaaggtc gccctatgga      540
gcagccaaac tttatgccta ttggattgta gtgaactttc gagaggctta taatctcttt      600
gcggtgaacg gcattctctt caatcatgag agtcctagaa gaggagctaa ttttgttact      660
cgaaaaatta gccggtcagt agctaagatt taccttggac aactggaatg tttcagtttg      720
ggaaatctgg acgccaaacg agactggggc catgccaagg actatgtcga ggctatgtgg      780
ctgatgttac aaaatgatga accagaggac tttgtcatag ctactgggga agttcatagt      840
gtccgtgaat ttgttgagaa atcattcatg cacattggaa agaccattgt gtgggaagga      900
aagaatgaaa atgaagtggg cagatgtaaa gagaccggca aaattcatgt gactgtggat      960
ctgaaatact accgaccaac tgaagtggac ttcctgcagg gagactgctc caaggcgcag     1020
cagaaactga actggaagcc ccgcgttgcc tttgacgagc tggtgaggga gatggtgcaa     1080
gccgatgtgg agctcatgag aaccaacccc aacgcctgag                          1120
```

<210> SEQ ID NO 29
<211> LENGTH: 575
<212> TYPE: PRT
<213> ORGANISM: Cricetulus griseus

<400> SEQUENCE: 29

```
Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45
```

```
Lys Leu Glu Arg Leu Lys Gln Gln Asn Glu Asp Leu Arg Arg Met Ala
     50                  55                  60

Glu Ser Leu Arg Ile Pro Glu Gly Pro Ile Asp Gln Gly Thr Ala Thr
 65                  70                  75                  80

Gly Arg Val Arg Val Leu Glu Glu Gln Leu Val Lys Ala Lys Glu Gln
                 85                  90                  95

Ile Glu Asn Tyr Lys Lys Gln Ala Arg Asn Asp Leu Gly Lys Asp His
                100                 105                 110

Glu Ile Leu Arg Arg Ile Glu Asn Gly Ala Lys Glu Leu Trp Phe
            115                 120                 125

Phe Leu Gln Ser Glu Leu Lys Lys Leu Lys Lys Leu Glu Gly Asn Glu
130                 135                 140

Leu Gln Arg His Ala Asp Glu Ile Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Glu Trp Arg Glu Lys Glu Ala Lys Asp Leu Thr Glu Leu Val Gln
                180                 185                 190

Arg Arg Ile Thr Tyr Leu Gln Asn Pro Lys Asp Cys Ser Lys Ala Arg
            195                 200                 205

Lys Leu Val Cys Asn Ile Asn Lys Gly Cys Gly Tyr Gly Cys Gln Leu
210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
                260                 265                 270

Ser Thr Gly His Trp Ser Gly Glu Val Lys Asp Lys Asn Val Gln Val
            275                 280                 285

Val Glu Leu Pro Ile Val Asp Ser Leu His Pro Arg Pro Pro Tyr Leu
290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Arg Glu Ile Glu Thr Thr Lys Lys
            340                 345                 350

Leu Gly Phe Lys His Pro Val Ile Gly Val His Val Arg Arg Thr Asp
            355                 360                 365

Lys Val Gly Thr Glu Ala Ala Phe His Pro Ile Glu Glu Tyr Met Val
370                 375                 380

His Val Glu Glu His Phe Gln Leu Leu Glu Arg Arg Met Lys Val Asp
385                 390                 395                 400

Lys Lys Arg Val Tyr Leu Ala Thr Asp Asp Pro Ser Leu Leu Lys Glu
                405                 410                 415

Ala Lys Thr Lys Tyr Ser Asn Tyr Glu Phe Ile Ser Asp Asn Ser Ile
            420                 425                 430

Ser Trp Ser Ala Gly Leu His Asn Arg Tyr Thr Glu Asn Ser Leu Arg
        435                 440                 445

Gly Val Ile Leu Asp Ile His Phe Leu Ser Gln Ala Asp Phe Leu Val
450                 455                 460
```

```
Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
            485                 490                 495

Tyr Tyr Phe Gly Gly Gln Asn Ala His Asn Gln Ile Ala Val Tyr Pro
        500                 505                 510

His Gln Pro Arg Thr Lys Glu Glu Ile Pro Met Glu Pro Gly Asp Ile
    515                 520                 525

Ile Gly Val Ala Gly Asn His Trp Asn Gly Tyr Ser Lys Gly Val Asn
530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575
```

<210> SEQ ID NO 30
<211> LENGTH: 321
<212> TYPE: PRT
<213> ORGANISM: Cricetulus griseus

<400> SEQUENCE: 30

```
Met Gly Glu Pro Gln Gly Ser Arg Arg Ile Leu Val Thr Gly Gly Ser
1               5                   10                  15

Gly Leu Val Gly Arg Ala Ile Gln Lys Val Val Ala Asp Gly Ala Gly
            20                  25                  30

Leu Pro Gly Glu Glu Trp Val Phe Val Ser Ser Lys Asp Ala Asp Leu
        35                  40                  45

Thr Asp Ala Ala Gln Thr Gln Ala Leu Phe Gln Lys Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Thr Arg Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Asn Gly Ser Ala Leu Thr Val Trp
        195                 200                 205

Gly Thr Gly Lys Pro Arg Arg Gln Phe Ile Tyr Ser Leu Asp Leu Ala
    210                 215                 220

Arg Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Lys Glu Ala Ala
                245                 250                 255

Glu Ala Val Val Glu Ala Met Asp Phe Cys Gly Glu Val Thr Phe Asp
            260                 265                 270
```

```
Ser Thr Lys Ser Asp Gly Gln Tyr Lys Lys Thr Ala Ser Asn Gly Lys
        275                 280                 285

Leu Arg Ala Tyr Leu Pro Asp Phe Arg Phe Thr Pro Phe Lys Gln Ala
    290                 295                 300

Val Lys Glu Thr Cys Ala Trp Phe Thr Asp Asn Tyr Glu Gln Ala Arg
305                 310                 315                 320

Lys

<210> SEQ ID NO 31
<211> LENGTH: 1728
<212> TYPE: DNA
<213> ORGANISM: Cricetulus griseus

<400> SEQUENCE: 31
```

| | | | | |
|---|---|---|---|---|
| atgcgggcat | ggactggttc | ctggcgttgg | attatgctca | ttcttttgc | ctggggacc | 60 |
| ttattgtttt | ataggtgg | tcatttggtt | cgagataatg | accaccctga | ccattctagc | 120 |
| agagaactct | ccaagattct | tgcaaagctg | agcgcttaa | acaacaaaa | tgaagacttg | 180 |
| aggagaatgg | ctgagtctct | ccgaatacca | gaaggccta | ttgatcaggg | gacagctaca | 240 |
| ggaagagtcc | gtgttttaga | gaacagctt | gttaaggcca | agaacagat | tgaaaattac | 300 |
| aagaaacaag | ctaggaatga | tctgggaaag | gatcatgaaa | tcttaaggag | gaggattgaa | 360 |
| aatggagcta | aagagctctg | gtttttcta | caaagtgaat | tgaagaaatt | aaagaaatta | 420 |
| gaaggaaacg | aactccaaag | acatgcagat | gaaattcttt | tggattttagg | acatcatgaa | 480 |
| aggtctatca | tgacagatct | atactacctc | agtcaaacag | atggagcagg | tgagtggcgg | 540 |
| gaaaaagaag | ccaaagatct | gacagagctg | gtccagcgga | gaataacata | tctgcagaat | 600 |
| cccaaggact | gcagcaaagc | cagaaagctg | gtatgtaata | tcaacaaagg | ctgtggctat | 660 |
| ggatgtcaac | tccatcatgt | ggtttactgc | ttcatgattg | cttatggcac | ccagcgaaca | 720 |
| ctcatcttgg | aatctcagaa | ttggcgctat | gctactggag | gatgggagac | tgtgtttaga | 780 |
| cctgtaagtg | agacatgcac | agacaggtct | ggcctctcca | ctggacactg | tcaggtgaa | 840 |
| gtgaaggaca | aaaatgttca | agtggtcgag | ctccccattg | tagacagcct | ccatcctcgt | 900 |
| cctccttact | acccttggc | tgtaccagaa | gaccttgcag | atcgactcct | gagagtccat | 960 |
| ggtgatcctg | cagtgtggtg | ggtatcccag | tttgtcaaat | acttgatccg | tccacaacct | 1020 |
| tggctggaaa | gggaaataga | gaaaccacc | aagaagcttg | gcttcaaaca | tccagttatt | 1080 |
| ggagtccatg | tcagacgcac | tgacaaagtg | ggaacagaag | cagccttcca | tcccattgag | 1140 |
| gaatacatgg | tacacgttga | agaacattt | cagcttctcg | aacgcagaat | gaaagtggat | 1200 |
| aaaaaaagag | tgtatctggc | cactgatgac | ccttctttgt | taaggaggc | aaagacaaag | 1260 |
| tactccaatt | atgaatttat | tagtgataac | tctatttctt | ggtcagctgg | actacacaac | 1320 |
| cgatacacag | aaaattcact | tcggggcgtg | atcctggata | tacattctct | ctcccaggct | 1380 |
| gacttccttg | tgtgtacttt | ttcatcccag | gtctgtaggg | ttgcttatga | aatcatgcaa | 1440 |
| acactgcatc | ctgatgcctc | tgcaaacttc | cattctttag | atgacatcta | ctattttgga | 1500 |
| ggccaaaatg | cccacaacca | gattgcagtt | tatcctcacc | aacctcgaac | taaagaggaa | 1560 |
| atccccatgg | aacctggaga | tatcattggt | gtggctggaa | accattggaa | tggttactct | 1620 |
| aaaggtgtca | acagaaaact | aggaaaaaca | ggcctgtacc | cttcctacaa | agtccgagag | 1680 |
| aagatagaaa | cagtcaaata | ccctacatat | cctgaagctg | aaaaatag | | 1728 |

```
<210> SEQ ID NO 32
<211> LENGTH: 966
<212> TYPE: DNA
<213> ORGANISM: Cricetulus griseus

<400> SEQUENCE: 32
atgggtgagc cccagggatc caggaggatc ctagtgacag ggggctctgg actggtgggc      60
agagctatcc agaaggtggt cgcagatggc gctggcttac ccggagagga atgggtgttt     120
gtctcctcca agatgcaga tctgacggat gcagcacaaa cccaagccct gttccagaag     180
gtacagccca cccatgtcat ccatcttgct gcaatggtag gaggcctttt ccggaatatc     240
aaatacaact tggatttctg gaggaagaat gtgcacatca atgacaacgt cctgcactca     300
gctttcgagg tgggcactcg caaggtggtc tcctgcctgt ccacctgtat cttccctgac     360
aagaccacct atcctattga tgaaacaatg atccacaatg gtccacccca cagcagcaat     420
tttgggtact cgtatgccaa gaggatgatt gacgtgcaga cagggccta cttccagcag     480 catggctgca ccttcactgc tgtcatccct accaatgtct ttggacctca tgacaacttc     540
aacattgaag atggccatgt gctgcctggc ctcatccata aggtgcatct ggccaagagt     600
aatggttcag ccttgactgt ttgggggtaca gggaaaccac ggaggcagtt catctactca     660
ctggacctag cccggctctt catctgggtc ctgcgggagt acaatgaagt tgagcccatc     720
atcctctcag tgggcgagga agatgaagtc tccattaagg aggcagctga ggctgtagtg     780
gaggccatgg acttctgtgg ggaagtcact tttgattcaa caaagtcaga tgggcagtat     840
aagaagacag ccagcaatgg caagcttcgg gcctacttgc ctgatttccg tttcacaccc     900
ttcaagcagg ctgtgaagga gacctgtgcc tggttcaccg acaactatga gcaggcccgg     960
aagtga                                                                966

<210> SEQ ID NO 33
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 33
ataatgcggg catggactgg ttc                                              23

<210> SEQ ID NO 34
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 34
atactatttt tcagcttcag gatatg                                           26

<210> SEQ ID NO 35
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 35
ataatgggtg agccccaggg atc                                              23

<210> SEQ ID NO 36
```

-continued

```
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 36
atatctagac aagggacagc agg                                               23

<210> SEQ ID NO 37
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 37
ataatggctc acgctcccgc tagctg                                            26

<210> SEQ ID NO 38
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 38
atatcaggcg ttggggttgg tt                                                22

<210> SEQ ID NO 39
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 39
ataatggcgt ctctgcgcga agc                                               23

<210> SEQ ID NO 40
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 40
atattaagat ttctccgaat cag                                               23

<210> SEQ ID NO 41
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 41
gtctgaattc aagcttgtag cgatcgccgc caccat                                 36

<210> SEQ ID NO 42
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 42
```

```
ggatccgcgg ccgctacgcc gccctcagat ctttatca                              38

<210> SEQ ID NO 43
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 43
gcttgaattc aagcttctag tacgcgtgtt taaacc                                36

<210> SEQ ID NO 44
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 44
gcggccgctg tccgcgcctt actaacactc tc                                    32

<210> SEQ ID NO 45
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 45
gtccgatatc atttaaatcg ccaccatggc tcacgctccc gctag                      45

<210> SEQ ID NO 46
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 46
atccctcgag ttatcaggcg ttggggttgg ttc                                   33
```